(12) United States Patent
Joshi et al.

(10) Patent No.: US 11,643,443 B2
(45) Date of Patent: May 9, 2023

(54) ELECTRICALLY CONDUCTIVE PROTEIN NANOFIBERS AND BIOFILMS

(71) Applicant: President and Fellows of Harvard College, Cambridge, MA (US)

(72) Inventors: Neel Satish Joshi, Somerville, MA (US); Noémie-Manuelle Dorval Courchesne, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 488 days.

(21) Appl. No.: 15/777,070

(22) PCT Filed: Nov. 18, 2016

(86) PCT No.: PCT/US2016/062743
§ 371 (c)(1),
(2) Date: May 17, 2018

(87) PCT Pub. No.: WO2017/087786
PCT Pub. Date: May 26, 2017

(65) Prior Publication Data
US 2018/0334483 A1    Nov. 22, 2018

Related U.S. Application Data

(60) Provisional application No. 62/257,441, filed on Nov. 19, 2015, provisional application No. 62/338,715, filed on May 19, 2016.

(51) Int. Cl.
| | | |
|---|---|---|
| C12N 15/74 | (2006.01) |
| C07K 14/245 | (2006.01) |
| C07K 14/47 | (2006.01) |
| C07K 14/395 | (2006.01) |
| C07K 14/195 | (2006.01) |
| C12N 9/08 | (2006.01) |
| C12N 9/36 | (2006.01) |

(52) U.S. Cl.
CPC ......... *C07K 14/245* (2013.01); *C07K 14/195* (2013.01); *C07K 14/395* (2013.01); *C07K 14/47* (2013.01); *C07K 14/4711* (2013.01); *C07K 14/4717* (2013.01); *C12N 9/0065* (2013.01); *C12N 9/2462* (2013.01); *C12Y 111/01007* (2013.01); *C12Y 302/01017* (2013.01); *C07K 2319/00* (2013.01); *C07K 2319/20* (2013.01); *C07K 2319/21* (2013.01); *C07K 2319/23* (2013.01); *C07K 2319/735* (2013.01)

(58) Field of Classification Search
None
See application file for complete search history.

(56) References Cited

U.S. PATENT DOCUMENTS

2014/0336357 A1* 11/2014 Reguera ............... C07K 14/195
                                                                    530/324
2018/0111968 A1*  4/2018 Lu ........................ B82Y 40/00

FOREIGN PATENT DOCUMENTS

WO        2014/176311 A1     10/2014
WO        WO-2014176311 A1 * 10/2014 ............. C07K 14/21

OTHER PUBLICATIONS

Dorval et al. Abstract Citation on line Mar. 30, 2016. (Year: 2016).*
International Search Report for Application No. PCT/US2016/062743, dated Apr. 25, 2017. 5 pages.
International Preliminary Report on Patentability for Application No. PCT/US2016/062743, dated May 31, 2018. 11 pages.

* cited by examiner

*Primary Examiner* — Jana A Hines
*Assistant Examiner* — Khatol S Shahnan Shah
(74) *Attorney, Agent, or Firm* — Foley Hoag LLP

(57) ABSTRACT

Methods of making engineered protein-based materials, nanofibers, and biofilms from bacterial amyloid-based structures that are capable of mediating long-range electron transport are provided.

17 Claims, 41 Drawing Sheets

Specification includes a Sequence Listing.

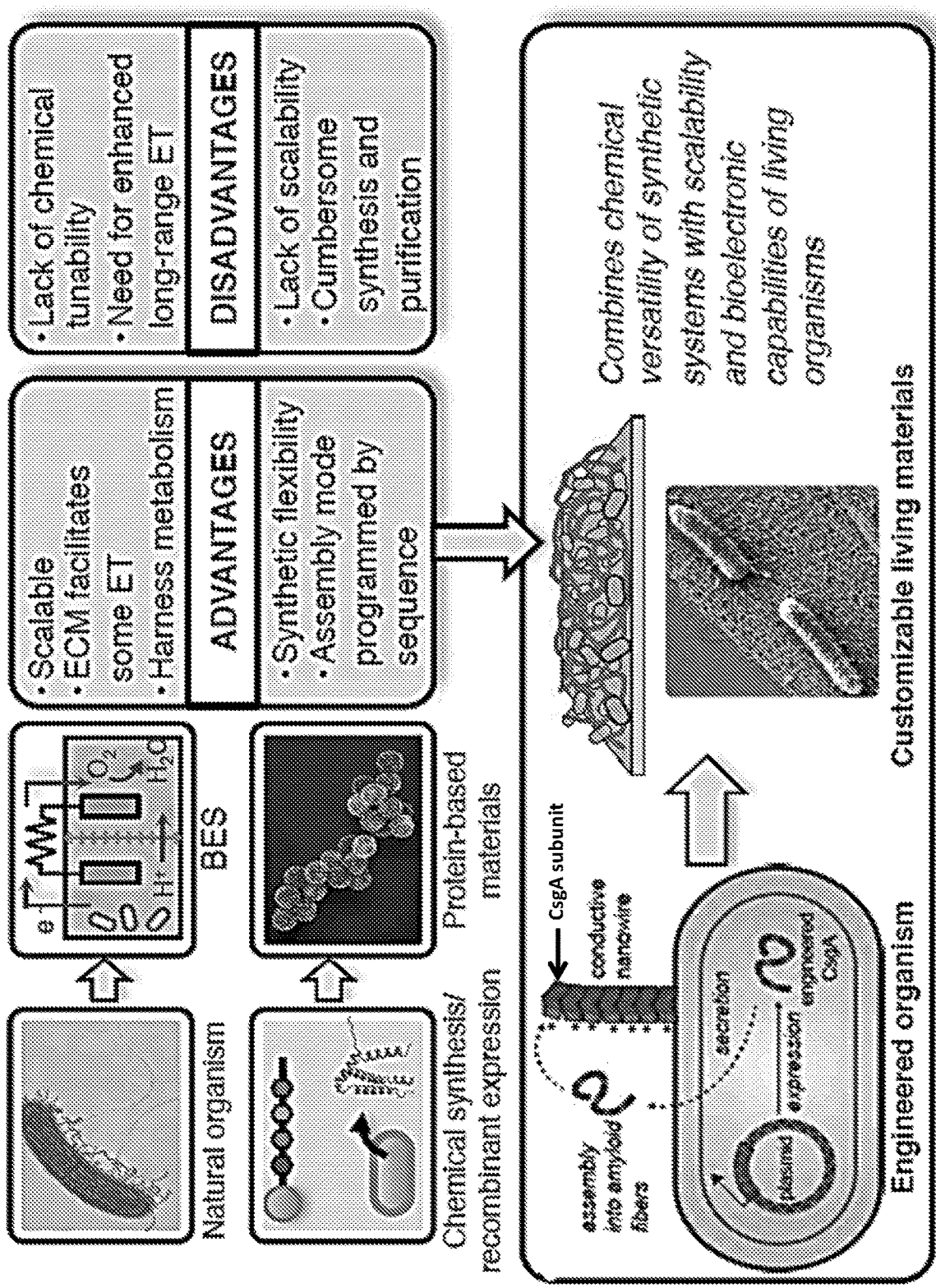

Fig. 4B

Wild-type CsgA with His-tag at the N-terminus nucleic acid sequence:

ATGAAAACTTTTAAAGTAGCAGCAATTGCAGCAATCGTATTCTCCGGTAGCGCTCTGGCAGGTGTTGTTCCTCAGTACGGCGGGCGGTA
ACCACGGTGGTGGCGGTAATAATAGCGGCCCAAATTCTGAGCTGAACATTTACCAGTACGGTGGCGGTAACTCTGCACTTGCTCTGCAAAC
TGATGCCCGTAACTCTGACTTACCCAGCAGTAATGTTGCAGATGTTGGTCAGGGCTCAGATGACAGCTCAATCGAT
CTGACCCAACGTGGCTTCGGTAACAGCGCTACTCTTGATCAGTGGAACGGCAAAATTCTGAAATGACGTTAAACAGTTCGGTGGTGCA
ACGGTGCTGCAGTTGACCAGACTGCATCTAACTCCTCCGTCAACGTGACTCAGTTGGCTTTGGTAACAACGCGACCGCTCATCAGTACGG
CTCTGGTGGCTCTGGTGGCTCTGGCGGCAGCGGGCATCACCACCACCATCATTAA (SEQ ID NO: 1)

Wild-type CsgA with His-tag at the N-terminus amino acid sequence:

MKLLKVAAIAAIVFSGSALAGVVPQYGGGGNHGGGGNNSGPNSELNIYQYGGGNSALALQTDARNSDLTITQHGGGNGADVGQGSDDSSID
LTQRGFGNSATLDQWNGKNSEMTVKQFGGGNGAAVDQTASNSSVNVTQVGFGNNATAHQYGSGGSGGSGGSGHHHHHH* (SEQ ID NO: 2)

☐ Sec peptide (excluded for residue numbering the residues)    ☐ Linker
▨ N22 peptide                                                    ▨ His-tag
▨ Five engineered pseudo-repeats of CsgA                        * Stop Plastocyanin "blue copper protein"

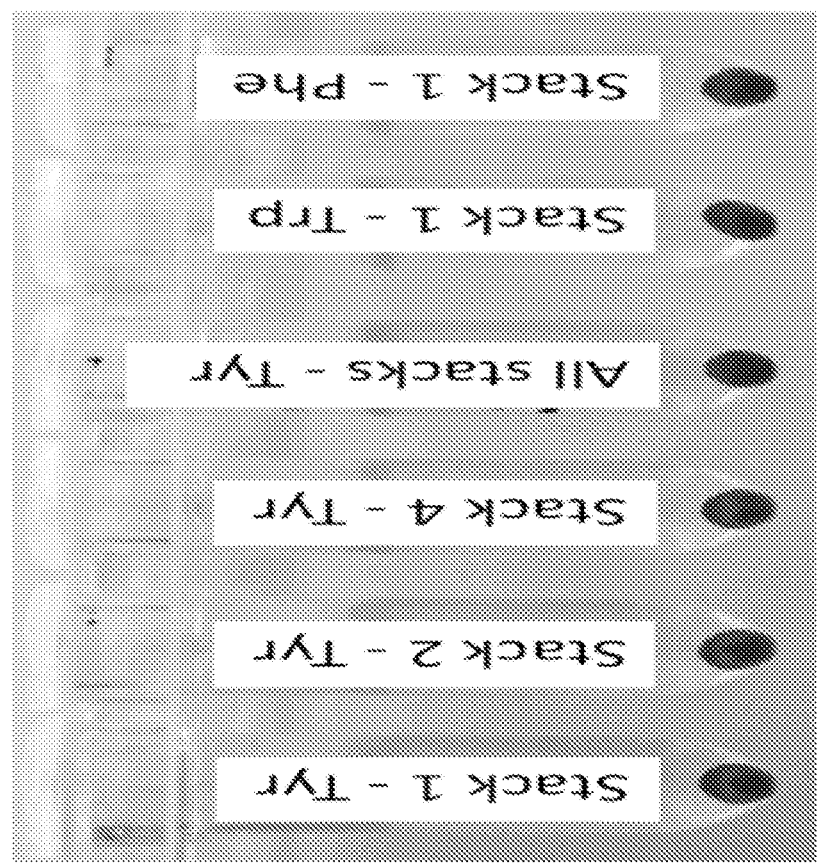
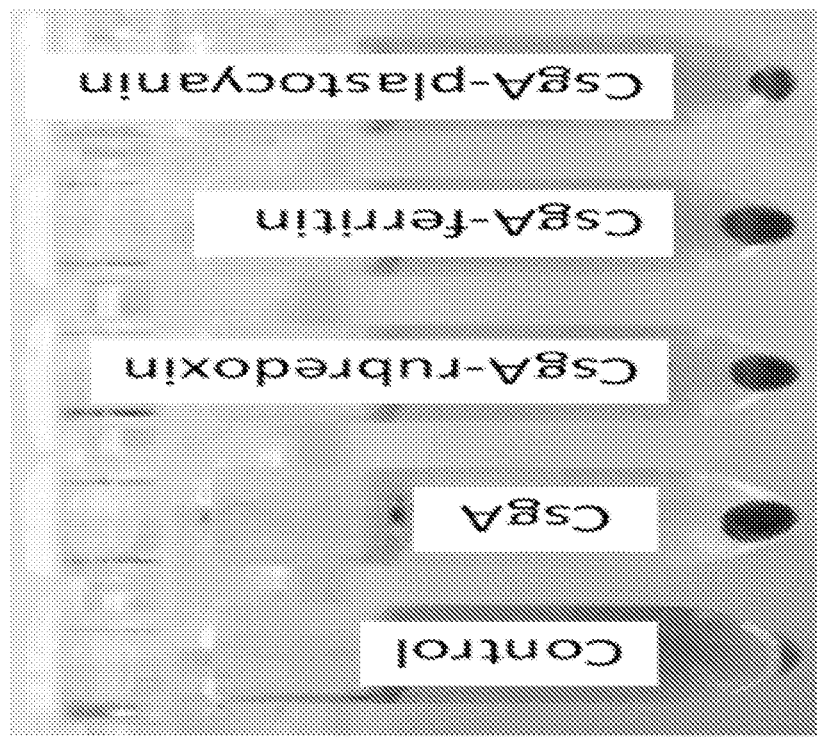
Fig. 6A

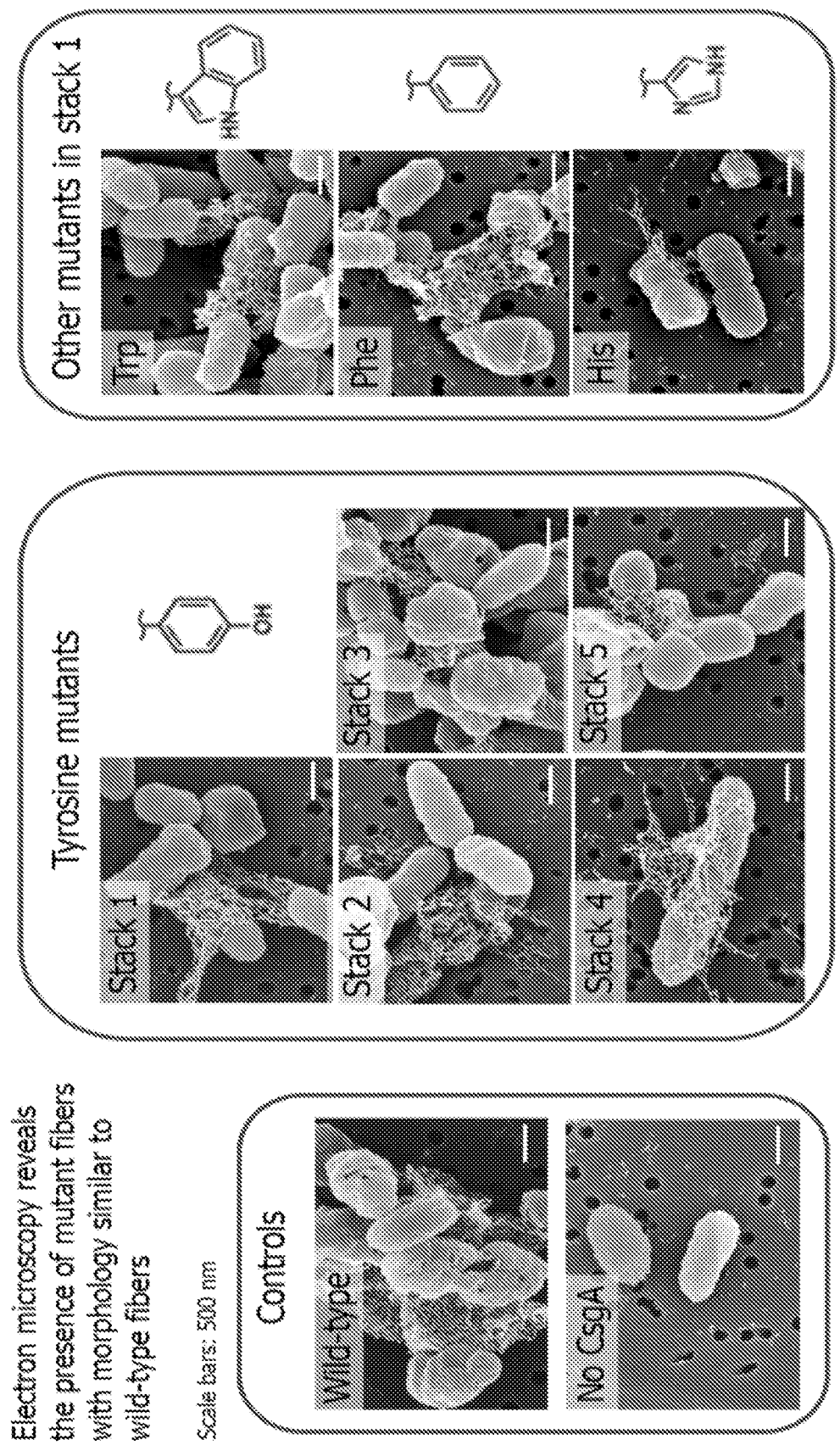

Fig. 13
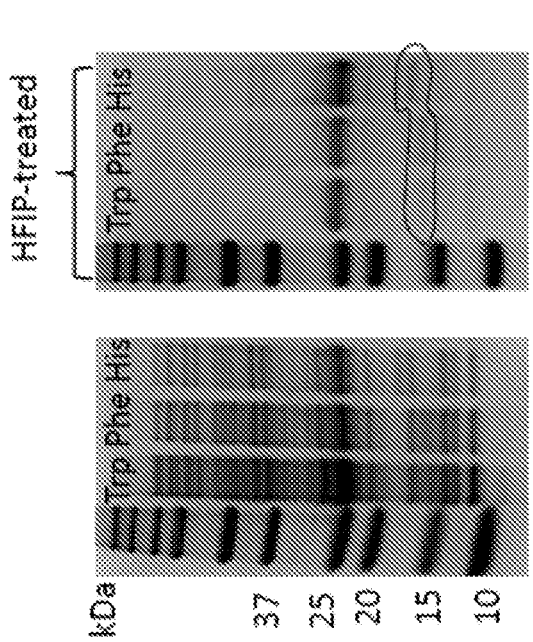
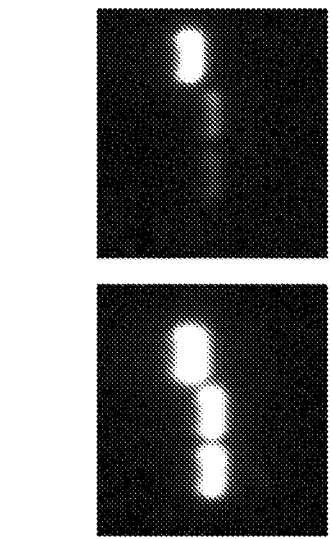
Stack 1 – Trp, Phe, His mutants
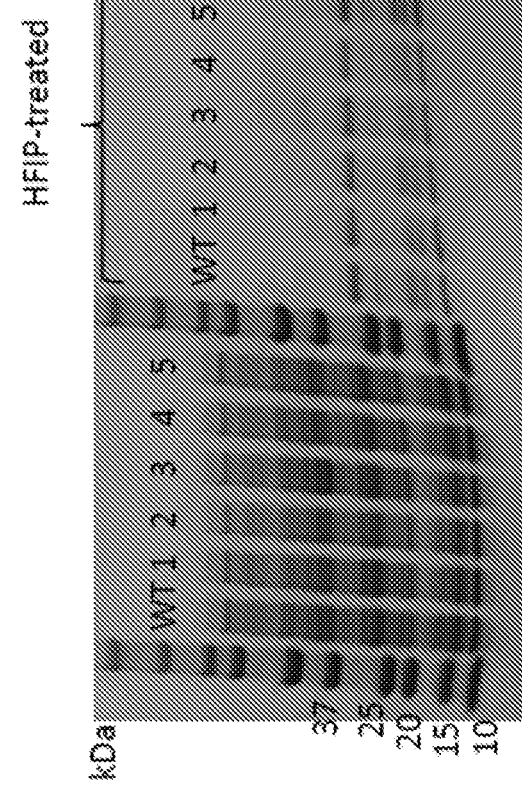
Stack 1 through 5 – Tyr mutants
SDS-PAGE
Anti-His Western

Assembly of conductive curli nanofiber films via filtration

Fig. 14B
Measuring electrical properties of curli nanofiber films
Silver interdigitated electrodes are directly drawn onto dried curli films deposited on filter membranes
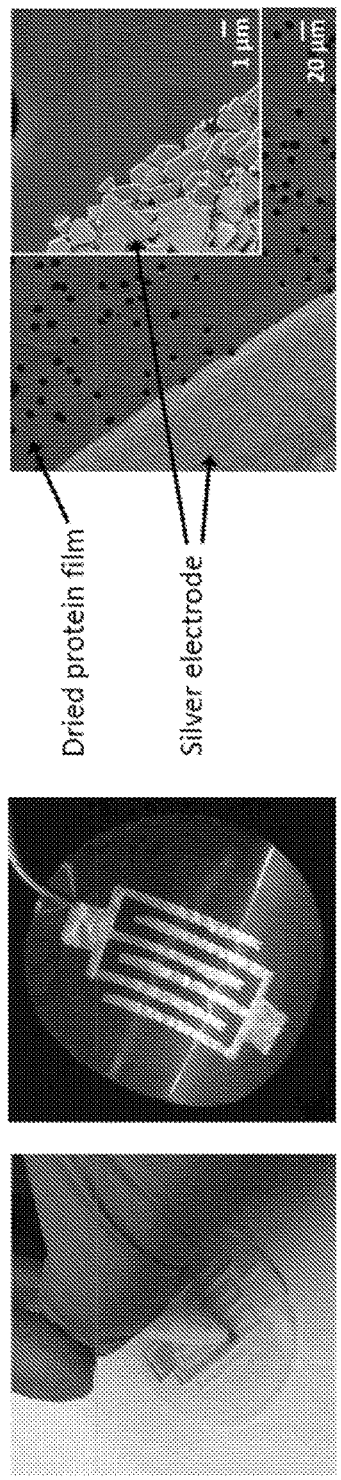
Resistance and current-voltage curves are measured to determine which protein films are conductive
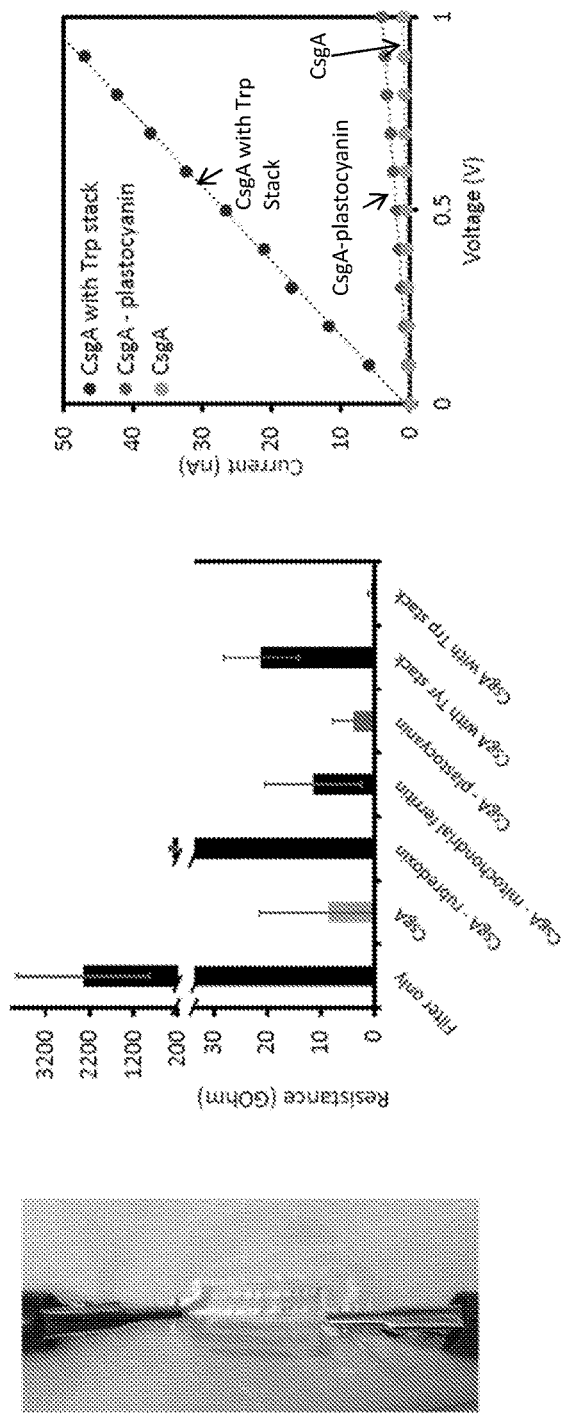

Fig. 16A
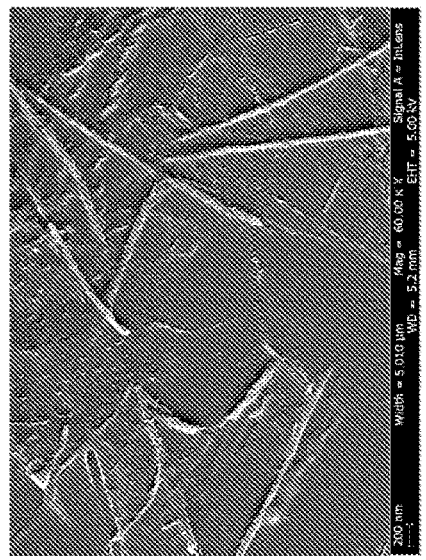
Rubredoxin
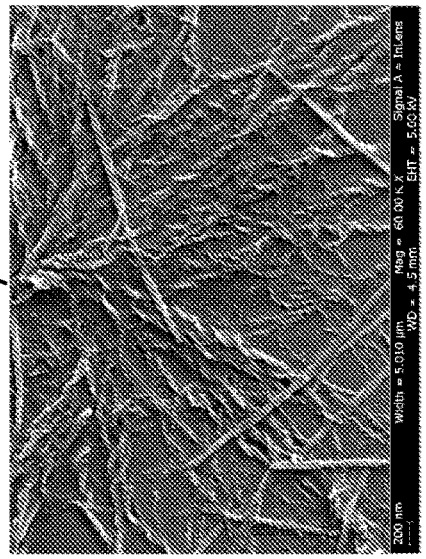
Plastocyanin
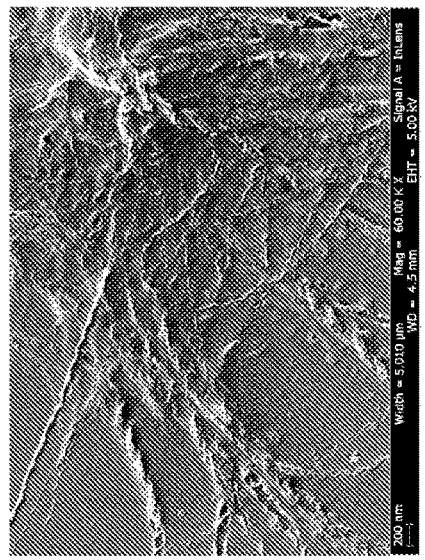
Metalloprotein fusions
Ferritin domain

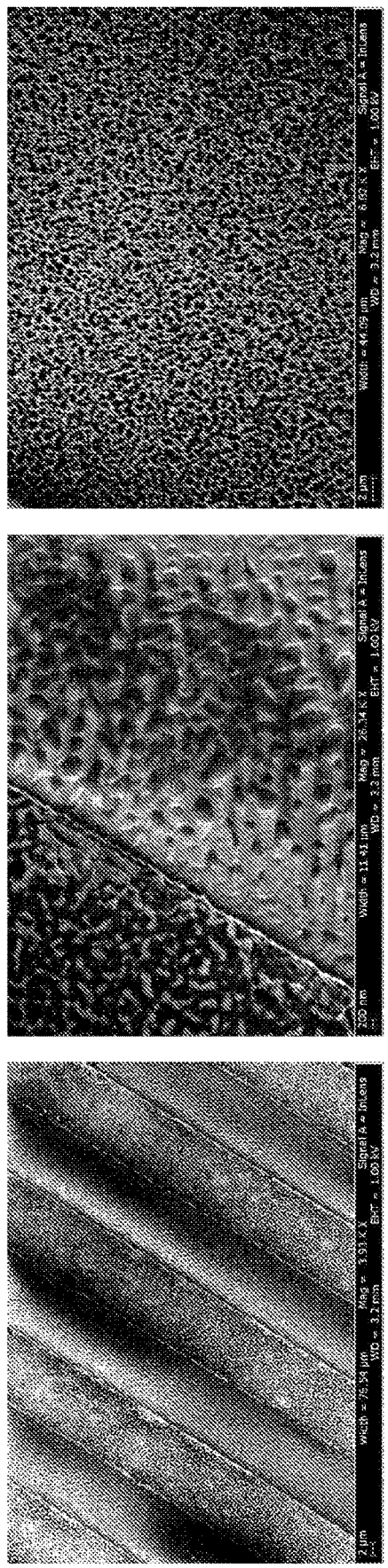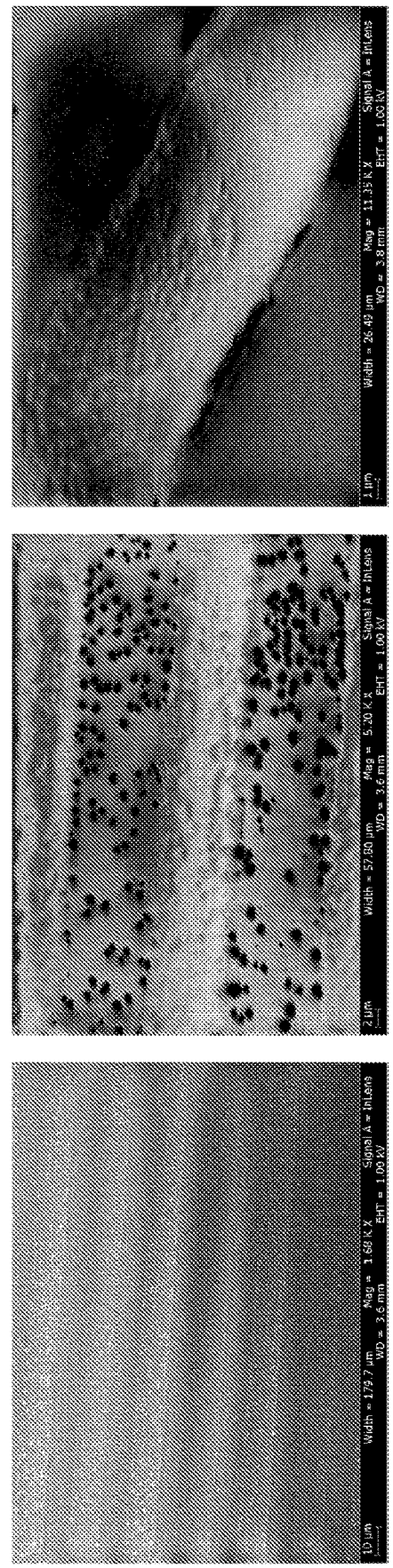
Fig. 20A
Fig. 20B

SEQUENCE LISTING

<160> NUMBER OF SEQ ID NOS: 90

<210> SEQ ID NO 1
<211> LENGTH: 510
<212> TYPE: DNA
<213> ORGANISM: Artificial Sequence
<220> FEATURE:
<223> OTHER INFORMATION: Synthetic: Wild-type CsgA with His-tag at the
      N-terminus nucleic acid sequence

<400> SEQUENCE: 1
atgaaacttt taaaagtagc agcaattgca gcaatcgtat tctccggtag cgctctggca      60
ggtgttgttc ctcagtacgg cggcggcggt aaccacggtg gtggcggtaa taatagcggc     120

-continued

```
ccaaattctg agctgaacat ttaccagtac ggtggcggta actctgcact tgctctgcaa    180
actgatgccc gtaactctga cttgactatt acccagcatg gcggcggtaa tggtgcagat    240
gttggtcagg gctcagatga cagctcaatc gatctgaccc aacgtggctt cggtaacagc    300
gctactcttg atcagtggaa cggcaaaaat tctgaaatga cggttaaaca gttcggtggt    360
ggcaacggtg ctgcagttga ccagactgca tctaactcct ccgtcaacgt gactcaggtt    420
ggctttggta acaacgcgac cgctcatcag tacggtctg gtggctctgg tggctctggc    480
ggcagcgggc atcaccacca ccatcattaa                                     510
```

<210> SEQ ID NO 2
<211> LENGTH: 169
<212> TYPE: PRT
<213> ORGANISM: Artificial Sequence
<220> FEATURE:
<223> OTHER INFORMATION: Synthetic: Wild-type CsgA with His-tag at the
      N-terminus amino acid sequence

<400> SEQUENCE: 2

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr Gly Ser Gly Gly Ser Gly Gly Ser Gly
145                 150                 155                 160

Gly Ser Gly His His His His His His
                165
```

<210> SEQ ID NO 3
<211> LENGTH: 338
<212> TYPE: DNA
<213> ORGANISM: Artificial Sequence
<220> FEATURE:
<223> OTHER INFORMATION: Synthetic: Stack 1 - Tyr

<400> SEQUENCE: 3

```
acggtggtgg cggtaataat agcggcccaa attcttatct gaacatttac cagtacggtg    60
gcggtaactc tgcacttgct ctgcaaactg atgcccgtaa ctcttacttg actattaccc    120
agcatggcgg cggtaatggt gcagatgttg gtcagggctc agatgacagc tatatcgatc    180
tgacccaacg tggcttcggt aacagcgcta ctcttgatca gtggaacggc aaaaattctt    240
atatgacggt taaacagttc ggtggtggca acggtgctgc agttgaccag actgcatcta    300
actcctacgt caacgtgact caggttggct ttggtaac                            338
```

<210> SEQ ID NO 4
<211> LENGTH: 333
<212> TYPE: DNA
<213> ORGANISM: Artificial Sequence
<220> FEATURE:
<223> OTHER INFORMATION: Synthetic: Stack 2 - Tyr

<400> SEQUENCE: 4

```
ggtaataata gcggcccaaa ttctgagctg tacatttacc agtacggtgg cggtaactct    60
gcacttgctc tgcaaactga tgcccgtaac tctgacttgt atattaccca gcatggcggc   120
ggtaatggtg cagatgttgg tcagggctca gatgacagct caatctatct gacccaacgt   180
ggcttcggta acagcgctac tcttgatcag tggaacggca aaaattctga aatgtatgtt   240
aaacagttcg gtggtggcaa cggtgctgca gttgaccaga ctgcatctaa ctcctccgtc   300
tacgtgactc aggttggctt tggtaacaac gcg                                333
```

<210> SEQ ID NO 5
<211> LENGTH: 264
<212> TYPE: DNA
<213> ORGANISM: Artificial Sequence
<220> FEATURE:
<223> OTHER INFORMATION: Synthetic: Stack 3 - Tyr

<400> SEQUENCE: 5

```
actgatgccc gtaactctga cttgactatt taccagcatg gcggcggtaa tggtgcagat    60
gttggtcagg gctcagatga cagctcaatc gatctgtacc aacgtggctt cggtaacagc   120
gctactcttg atcagtggaa cggcaaaaat tctgaaatga cggtttatca gttcggtggt   180
ggcaacggtg ctgcagttga ccagactgca tctaactcct ccgtcaacgt gatcaggtt    240 ggctttggta caacgcgac cgct                                           264
```

<210> SEQ ID NO 6
<211> LENGTH: 330
<212> TYPE: DNA
<213> ORGANISM: Artificial Sequence
<220> FEATURE:
<223> OTHER INFORMATION: Synthetic: Stack 4 - Tyr

<400> SEQUENCE: 6

```
taccagtacg gtggcggtaa ctctgcactt tatctgcaaa ctgatgcccg taactctgac    60
ttgactatta cccagcatgg cggcggtaat ggtgcatatg ttggtcaggg ctcagatgac   120
agctcaatcg atctgaccca acgtggcttc ggtaacagcg cttatcttga tcagtggaac   180
ggcaaaaatt ctgaaatgac ggttaaacag ttcggtggtg caacggtgc ttatgttgac    240 cagactgcat ctaactcctc cgtcaacgtg actcaggttg ctttggtaa caacgcgtat   300 gctcatcagt acggctctgg tggctctggt                                    330
```

<210> SEQ ID NO 7
<211> LENGTH: 264
<212> TYPE: DNA
<213> ORGANISM: Artificial Sequence
<220> FEATURE:
<223> OTHER INFORMATION: Synthetic: Stack 5 - Tyr

<400> SEQUENCE: 7

```
tacggtggcg gtaactctgc acttgctctg tatactgatg cccgtaactc tgacttgact    60
attacccagc atggcggcgg taatggtgca gatgtttatc agggctcaga tgacagctca   120
```

```
atcgatctga cccaacgtgg cttcggtaac agcgctactc tttatcagtg gaacggcaaa    180
aattctgaaa tgacggttaa acagttcggt ggtggcaacg gtgctgcagt ttaccagact    240
gcatctaact cctccgtcaa cgtg                                           264
```

<210> SEQ ID NO 8
<211> LENGTH: 338
<212> TYPE: DNA
<213> ORGANISM: Artificial Sequence
<220> FEATURE:
<223> OTHER INFORMATION: Synthetic: Stack 1  Trp

<400> SEQUENCE: 8

```
acggtggtgg cggtaataat agcggcccaa attcttggct gaacatttac cagtacggtg     60
gcggtaactc tgcacttgct ctgcaaactg atgcccgtaa ctcttggttg actattaccc    120
agcatggcgg cggtaatggt gcagatgttg gtcagggctc agatgacagc tggatcgatc    180
tgacccaacg tggcttcggt aacagcgcta ctcttgatca gtggaacggc aaaaattctt    240
ggatgacggt taaacagttc ggtggtggca acggtgctgc agttgaccag actgcatcta    300
actcctgggt caacgtgact caggttggct ttggtaac                            338
```

<210> SEQ ID NO 9
<211> LENGTH: 338
<212> TYPE: DNA
<213> ORGANISM: Artificial Sequence
<220> FEATURE:
<223> OTHER INFORMATION: Synthetic: Stack 1  Phe

<400> SEQUENCE: 9

```
acggtggtgg cggtaataat agcggcccaa attcttttct gaacatttac cagtacggtg     60
gcggtaactc tgcacttgct ctgcaaactg atgcccgtaa ctctttcttg actattaccc    120
agcatggcgg cggtaatggt gcagatgttg gtcagggctc agatgacagc tttatcgatc    180
tgacccaacg tggcttcggt aacagcgcta ctcttgatca gtggaacggc aaaaattctt    240
ttatgacggt taaacagttc ggtggtggca acggtgctgc agttgaccag actgcatcta    300
actccttcgt caacgtgact caggttggct ttggtaac                            338
```

<210> SEQ ID NO 10
<211> LENGTH: 338
<212> TYPE: DNA
<213> ORGANISM: Artificial Sequence
<220> FEATURE:
<223> OTHER INFORMATION: Synthetic: Stack 1  His

<400> SEQUENCE: 10

```
acggtggtgg cggtaataat agcggcccaa attctcatct gaacatttac cagtacggtg     60
gcggtaactc tgcacttgct ctgcaaactg atgcccgtaa ctctcacttg actattaccc    120
agcatggcgg cggtaatggt gcagatgttg gtcagggctc agatgacagc catatcgatc    180
tgacccaacg tggcttcggt aacagcgcta ctcttgatca gtggaacggc aaaaattctc    240
atatgacggt taaacagttc ggtggtggca acggtgctgc agttgaccag actgcatcta    300
actcccacgt caacgtgact caggttggct ttggtaac                            338
```

<210> SEQ ID NO 11
<211> LENGTH: 377
<212> TYPE: DNA
<213> ORGANISM: Artificial Sequence
<220> FEATURE:
<223> OTHER INFORMATION: Synthetic: Stack 1,2,3,4 and 5 - Tyr

<400> SEQUENCE: 11

```
acggtggtgg cggtaataat agcggcccaa attcttatct gtatatttac cagtacggtg    60
gcggtaactc tgcactttat ctgtatactg atgcccgtaa ctcttacttg tatatttatc   120
agcatggcgg cggtaatggt gcatatgttt atcagggctc agatgacagc tatatctatc   180
tgtatcaacg tggcttcggt aacagcgctt atctttatca gtggaacggc aaaaattctt   240
atatgtatgt ttatcagttc ggtggtggca acggtgctta tgtttatcag actgcatcta   300
actcctacgt ctatgtgtat caggttggct ttggtaacaa cgcgtatgct catcagtacg   360
gctctggtgg ctctggt                                                  377
```

<210> SEQ ID NO 12
<211> LENGTH: 338
<212> TYPE: DNA
<213> ORGANISM: Artificial Sequence
<220> FEATURE:
<223> OTHER INFORMATION: Synthetic: Stack 1 NSAA

<400> SEQUENCE: 12

```
acggtggtgg cggtaataat agcggcccaa attcttagct gaacatttac cagtacggtg    60
gcggtaactc tgcacttgct ctgcaaactg atgcccgtaa ctcttagttg actattaccc   120
agcatggcgg cggtaatggt gcagatgttg gtcagggctc agatgacagc tagatcgatc   180
tgacccaacg tggcttcggt aacagcgcta ctcttgatca gtggaacggc aaaaattctt   240
agatgacggt taaacagttc ggtggtggca acggtgctgc agttgaccag actgcatcta   300
actcctaggt caacgtgact caggttggct ttggtaac                           338
```

<210> SEQ ID NO 13
<211> LENGTH: 169
<212> TYPE: PRT
<213> ORGANISM: Artificial Sequence
<220> FEATURE:
<223> OTHER INFORMATION: Synthetic: Stack 1 Tyr

<400> SEQUENCE: 13

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Tyr Leu Asn Ile Tyr
            35                  40                  45

Gln Tyr Gly Gly Gly Asn Ser Ala Leu Ala Leu Gln Thr Asp Ala Arg
    50                  55                  60

Asn Ser Tyr Leu Thr Ile Thr Gln His Gly Gly Gly Asn Gly Ala Asp
65                  70                  75                  80

Val Gly Gln Gly Ser Asp Asp Ser Tyr Ile Asp Leu Thr Gln Arg Gly
                85                  90                  95

Phe Gly Asn Ser Ala Thr Leu Asp Gln Trp Asn Gly Lys Asn Ser Tyr
            100                 105                 110

Met Thr Val Lys Gln Phe Gly Gly Gly Asn Gly Ala Ala Val Asp Gln
        115                 120                 125

Thr Ala Ser Asn Ser Tyr Val Asn Val Thr Gln Val Gly Phe Gly Asn
    130                 135                 140

Asn Ala Thr Ala His Gln Tyr Gly Ser Gly Gly Ser Gly Gly Ser Gly
145                 150                 155                 160
```

Gly Ser Gly His His His His His
              165

<210> SEQ ID NO 14
<211> LENGTH: 169
<212> TYPE: PRT
<213> ORGANISM: Artificial Sequence
<220> FEATURE:
<223> OTHER INFORMATION: Synthetic: Stack 2  Tyr

<400> SEQUENCE: 14

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Glu Leu Tyr Ile Tyr
            35                  40                  45

Gln Tyr Gly Gly Gly Asn Ser Ala Leu Ala Leu Gln Thr Asp Ala Arg
    50                  55                  60

Asn Ser Asp Leu Tyr Ile Thr Gln His Gly Gly Gly Asn Gly Ala Asp
65                  70                  75                  80

Val Gly Gln Gly Ser Asp Asp Ser Ser Ile Tyr Leu Thr Gln Arg Gly
                85                  90                  95

Phe Gly Asn Ser Ala Thr Leu Asp Gln Trp Asn Gly Lys Asn Ser Glu
            100                 105                 110

Met Tyr Val Lys Gln Phe Gly Gly Gly Asn Gly Ala Ala Val Asp Gln
    115                 120                 125

Thr Ala Ser Asn Ser Ser Val Tyr Val Thr Gln Val Gly Phe Gly Asn
130                 135                 140

Asn Ala Thr Ala His Gln Tyr Gly Ser Gly Gly Ser Gly Gly Ser Gly
145                 150                 155                 160

Gly Ser Gly His His His His His
              165

<210> SEQ ID NO 15
<211> LENGTH: 169
<212> TYPE: PRT
<213> ORGANISM: Artificial Sequence
<220> FEATURE:
<223> OTHER INFORMATION: Synthetic: Stack 3  Tyr

<400> SEQUENCE: 15

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
    50                  55                  60

Asn Ser Asp Leu Thr Ile Tyr Gln His Gly Gly Gly Asn Gly Ala Asp
65                  70                  75                  80

Val Gly Gln Gly Ser Asp Asp Ser Ser Ile Asp Leu Tyr Gln Arg Gly
                85                  90                  95

Phe Gly Asn Ser Ala Thr Leu Asp Gln Trp Asn Gly Lys Asn Ser Glu
            100                 105                 110

Met Thr Val Tyr Gln Phe Gly Gly Gly Asn Gly Ala Ala Val Asp Gln
    115                 120                 125

```
Thr Ala Ser Asn Ser Ser Val Asn Val Tyr Gln Val Gly Phe Gly Asn
            130                 135                 140

Asn Ala Thr Ala His Gln Tyr Gly Ser Gly Gly Ser Gly Gly Ser Gly
145                 150                 155                 160

Gly Ser Gly His His His His His His
                165
```

<210> SEQ ID NO 16
<211> LENGTH: 169
<212> TYPE: PRT
<213> ORGANISM: Artificial Sequence
<220> FEATURE:
<223> OTHER INFORMATION: Synthetic: Stack 4  Tyr

<400> SEQUENCE: 16

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Tyr Leu Gln Thr Asp Ala Arg
50                  55                  60

Asn Ser Asp Leu Thr Ile Thr Gln His Gly Gly Gly Asn Gly Ala Tyr
65                  70                  75                  80

Val Gly Gln Gly Ser Asp Asp Ser Ser Ile Asp Leu Thr Gln Arg Gly
                85                  90                  95

Phe Gly Asn Ser Ala Tyr Leu Asp Gln Trp Asn Gly Lys Asn Ser Glu
            100                 105                 110

Met Thr Val Lys Gln Phe Gly Gly Gly Asn Gly Ala Tyr Val Asp Gln
            115                 120                 125

Thr Ala Ser Asn Ser Ser Val Asn Val Thr Gln Val Gly Phe Gly Asn
            130                 135                 140

Asn Ala Tyr Ala His Gln Tyr Gly Ser Gly Gly Ser Gly Gly Ser Gly
145                 150                 155                 160

Gly Ser Gly His His His His His His
                165
```

<210> SEQ ID NO 17
<211> LENGTH: 169
<212> TYPE: PRT
<213> ORGANISM: Artificial Sequence
<220> FEATURE:
<223> OTHER INFORMATION: Synthetic: Stack 5  Tyr

<400> SEQUENCE: 17

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Tyr Thr Asp Ala Arg
50                  55                  60

Asn Ser Asp Leu Thr Ile Thr Gln His Gly Gly Gly Asn Gly Ala Asp
65                  70                  75                  80

Val Tyr Gln Gly Ser Asp Asp Ser Ser Ile Asp Leu Thr Gln Arg Gly
```

```
            85                  90                  95
Phe Gly Asn Ser Ala Thr Leu Tyr Gln Trp Asn Gly Lys Asn Ser Glu
            100                 105                 110

Met Thr Val Lys Gln Phe Gly Gly Asn Gly Ala Ala Val Tyr Gln
        115                 120                 125

Thr Ala Ser Asn Ser Ser Val Asn Val Thr Gln Val Gly Phe Gly Asn
        130                 135                 140

Asn Ala Thr Ala His Gln Tyr Gly Ser Gly Gly Ser Gly Gly Ser Gly
145                 150                 155                 160

Gly Ser Gly His His His His His His
                165

<210> SEQ ID NO 18
<211> LENGTH: 169
<212> TYPE: PRT
<213> ORGANISM: Artificial Sequence
<220> FEATURE:
<223> OTHER INFORMATION: Synthetic: Stack 1  Trp

<400> SEQUENCE: 18

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Trp Leu Asn Ile Tyr
        35                  40                  45

Gln Tyr Gly Gly Gly Asn Ser Ala Leu Ala Leu Gln Thr Asp Ala Arg
50                  55                  60

Asn Ser Trp Leu Thr Ile Thr Gln His Gly Gly Gly Asn Gly Ala Asp
65                  70                  75                  80

Val Gly Gln Gly Ser Asp Asp Ser Trp Ile Asp Leu Thr Gln Arg Gly
                85                  90                  95

Phe Gly Asn Ser Ala Thr Leu Asp Gln Trp Asn Gly Lys Asn Ser Trp
            100                 105                 110

Met Thr Val Lys Gln Phe Gly Gly Asn Gly Ala Ala Val Asp Gln
        115                 120                 125

Thr Ala Ser Asn Ser Trp Val Asn Val Thr Gln Val Gly Phe Gly Asn
        130                 135                 140

Asn Ala Thr Ala His Gln Tyr Gly Ser Gly Gly Ser Gly Gly Ser Gly
145                 150                 155                 160

Gly Ser Gly His His His His His His
                165

<210> SEQ ID NO 19
<211> LENGTH: 169
<212> TYPE: PRT
<213> ORGANISM: Artificial Sequence
<220> FEATURE:
<223> OTHER INFORMATION: Synthetic: Stack 1  Phe

<400> SEQUENCE: 19

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Phe Leu Asn Ile Tyr
        35                  40                  45
```

```
Gln Tyr Gly Gly Gly Asn Ser Ala Leu Ala Leu Gln Thr Asp Ala Arg
    50                  55                  60

Asn Ser Phe Leu Thr Ile Thr Gln His Gly Gly Gly Asn Gly Ala Asp
 65                  70                  75                  80

Val Gly Gln Gly Ser Asp Asp Ser Phe Ile Asp Leu Thr Gln Arg Gly
                 85                  90                  95

Phe Gly Asn Ser Ala Thr Leu Asp Gln Trp Asn Gly Lys Asn Ser Phe
             100                 105                 110

Met Thr Val Lys Gln Phe Gly Gly Gly Asn Gly Ala Ala Val Asp Gln
         115                 120                 125

Thr Ala Ser Asn Ser Phe Val Asn Val Thr Gln Val Gly Phe Gly Asn
     130                 135                 140

Asn Ala Thr Ala His Gln Tyr Gly Ser Gly Gly Ser Gly Gly Ser Gly
145                 150                 155                 160

Gly Ser Gly His His His His His His
                165
```

<210> SEQ ID NO 20
<211> LENGTH: 169
<212> TYPE: PRT
<213> ORGANISM: Artificial Sequence
<220> FEATURE:
<223> OTHER INFORMATION: Synthetic: Stack 1  His

<400> SEQUENCE: 20

```
Met Lys Leu Leu Lys Val Ala Ala Ile Ala Ala Ile Val Phe Ser Gly
  1               5                  10                  15

Ser Ala Leu Ala Gly Val Val Pro Gln Tyr Gly Gly Gly Asn His
             20                  25                  30

Gly Gly Gly Gly Asn Asn Ser Gly Pro Asn Ser His Leu Asn Ile Tyr
         35                  40                  45

Gln Tyr Gly Gly Gly Asn Ser Ala Leu Ala Leu Gln Thr Asp Ala Arg
    50                  55                  60

Asn Ser His Leu Thr Ile Thr Gln His Gly Gly Gly Asn Gly Ala Asp
 65                  70                  75                  80

Val Gly Gln Gly Ser Asp Asp Ser His Ile Asp Leu Thr Gln Arg Gly
                 85                  90                  95

Phe Gly Asn Ser Ala Thr Leu Asp Gln Trp Asn Gly Lys Asn Ser His
             100                 105                 110

Met Thr Val Lys Gln Phe Gly Gly Gly Asn Gly Ala Ala Val Asp Gln
         115                 120                 125

Thr Ala Ser Asn Ser His Val Asn Val Thr Gln Val Gly Phe Gly Asn
     130                 135                 140

Asn Ala Thr Ala His Gln Tyr Gly Ser Gly Gly Ser Gly Gly Ser Gly
145                 150                 155                 160

Gly Ser Gly His His His His His His
                165
```

<210> SEQ ID NO 21
<211> LENGTH: 169
<212> TYPE: PRT
<213> ORGANISM: Artificial Sequence
<220> FEATURE:
<223> OTHER INFORMATION: Synthetic: Stack 1,2,3,4 and 5  Tyr

<400> SEQUENCE: 21

```
Met Lys Leu Leu Lys Val Ala Ala Ile Ala Ala Ile Val Phe Ser Gly
  1               5                  10                  15
```

Ser Ala Leu Ala Gly Val Val Pro Gln Tyr Gly Gly Gly Asn His
            20                  25                  30

Gly Gly Gly Gly Asn Asn Ser Gly Pro Asn Ser Tyr Leu Tyr Ile Tyr
        35                  40                  45

Gln Tyr Gly Gly Gly Asn Ser Ala Leu Tyr Leu Tyr Thr Asp Ala Arg
50                  55                  60

Asn Ser Tyr Leu Tyr Ile Tyr Gln His Gly Gly Gly Asn Gly Ala Tyr
65                  70                  75                  80

Val Tyr Gln Gly Ser Asp Asp Ser Tyr Ile Tyr Leu Tyr Gln Arg Gly
                85                  90                  95

Phe Gly Asn Ser Ala Tyr Leu Tyr Gln Trp Asn Gly Lys Asn Ser Tyr
            100                 105                 110

Met Tyr Val Tyr Gln Phe Gly Gly Asn Gly Ala Tyr Val Tyr Gln
            115                 120                 125

Thr Ala Ser Asn Ser Tyr Val Tyr Val Tyr Gln Val Gly Phe Gly Asn
130                 135                 140

Asn Ala Tyr Ala His Gln Tyr Gly Ser Gly Gly Ser Gly Gly Ser Gly
145                 150                 155                 160

Gly Ser Gly His His His His His His
            165

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44
<211> LENGTH: 151
<212> TYPE: PRT
<213> ORGANISM: Escherichia coli str. K-12 substr. MG1655
<220> FEATURE:
<221> NAME/KEY: misc_feature
<223> OTHER INFORMATION: CsgA polypeptide

<400> SEQUENCE: 44

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr
145                 150
```

<210> SEQ ID NO 45
<211> LENGTH: 5
<212> TYPE: PRT
<213> ORGANISM: Artificial Sequence
<220> FEATURE:
<223> OTHER INFORMATION: Synthetic: Stack 1

<400> SEQUENCE: 45

Glu Asp Ser Glu Ser

```
<210> SEQ ID NO 46
<211> LENGTH: 5
<212> TYPE: PRT
<213> ORGANISM: Artificial Sequence
<220> FEATURE:
<223> OTHER INFORMATION: Synthetic: Stack 2

<400> SEQUENCE: 46

Asn Thr Asp Thr Asn
1               5

<210> SEQ ID NO 47
<211> LENGTH: 4
<212> TYPE: PRT
<213> ORGANISM: Artificial Sequence
<220> FEATURE:
<223> OTHER INFORMATION: Synthetic: Stack 3

<400> SEQUENCE: 47

Thr Thr Lys Thr
1

<210> SEQ ID NO 48
<211> LENGTH: 5
<212> TYPE: PRT
<213> ORGANISM: Artificial Sequence
<220> FEATURE:
<223> OTHER INFORMATION: Synthetic: Stack 4

<400> SEQUENCE: 48

Ala Asp Thr Ala Thr
1               5

<210> SEQ ID NO 49
<211> LENGTH: 4
<212> TYPE: PRT
<213> ORGANISM: Artificial Sequence
<220> FEATURE:
<223> OTHER INFORMATION: Synthetic: Stack 5

<400> SEQUENCE: 49

Gln Gly Asp Asp
1

<210> SEQ ID NO 50
<211> LENGTH: 23
<212> TYPE: PRT
<213> ORGANISM: Artificial Sequence
<220> FEATURE:
<223> OTHER INFORMATION: Synthetic: Pseudo-repeat sequence

<400> SEQUENCE: 50

Ser Glu Leu Asn Ile Tyr Gln Tyr Gly Gly Gly Asn Ser Ala Leu Ala
1               5                   10                  15

Leu Gln Thr Asp Ala Arg Asn
            20

<210> SEQ ID NO 51
<211> LENGTH: 22
<212> TYPE: PRT
<213> ORGANISM: Artificial Sequence
<220> FEATURE:
<223> OTHER INFORMATION: Synthetic: Pseudo-repeat sequence

<400> SEQUENCE: 51
```

-continued

```
Ser Asp Leu Thr Ile Thr Gln His Gly Gly Gly Asn Gly Ala Asp Val
1               5                   10                  15

Gly Gln Gly Ser Asp Asp
            20

<210> SEQ ID NO 52
<211> LENGTH: 23
<212> TYPE: PRT
<213> ORGANISM: Artificial Sequence
<220> FEATURE:
<223> OTHER INFORMATION: Synthetic: Pseudo-repeat sequence

<400> SEQUENCE: 52

Ser Ser Ile Asp Leu Thr Gln Arg Gly Phe Gly Asn Ser Ala Thr Leu
1               5                   10                  15

Asp Gln Trp Asn Gly Lys Asn
            20

<210> SEQ ID NO 53
<211> LENGTH: 22
<212> TYPE: PRT
<213> ORGANISM: Artificial Sequence
<220> FEATURE:
<223> OTHER INFORMATION: Synthetic: Pseudo-repeat sequence

<400> SEQUENCE: 53

Ser Glu Met Thr Val Lys Gln Phe Gly Gly Gly Asn Gly Ala Ala Val
1               5                   10                  15

Asp Gln Thr Ala Ser Asn
            20

<210> SEQ ID NO 54
<211> LENGTH: 19
<212> TYPE: PRT
<213> ORGANISM: Artificial Sequence
<220> FEATURE:
<223> OTHER INFORMATION: Synthetic: Pseudo-repeat sequence

<400> SEQUENCE: 54

Ser Ser Val Asn Val Thr Gln Val Gly Phe Gly Asn Asn Ala Thr Ala
1               5                   10                  15

His Gln Tyr

<210> SEQ ID NO 55
<211> LENGTH: 119
<212> TYPE: PRT
<213> ORGANISM: Prochlorococcus marinus subsp. marinus str. CCMP1375
<220> FEATURE:
<221> NAME/KEY: misc_feature
<223> OTHER INFORMATION: Plastocyanin, PetE

<400> SEQUENCE: 55

Met Ile Ser Ser Leu Arg Ser Ala Leu Ser Ala Cys Phe Ala Leu Leu
1               5                   10                  15

Leu Val Leu Ala Phe Gly Val Ala Ser Ala Gln Ala Lys Thr Val Glu
                20                  25                  30

Val Lys Leu Gly Thr Asp Ala Gly Met Leu Ala Phe Glu Pro Ser Ser
            35                  40                  45

Val Thr Ile Ser Thr Gly Asp Ser Val Lys Phe Val Asn Asn Lys Leu
        50                  55                  60

Ala Pro His Asn Ala Val Phe Glu Gly His Glu Leu Ser His Pro
65                  70                  75                  80
```

Asp Leu Ala Phe Ala Pro Gly Glu Ser Trp Gln Glu Thr Phe Thr Glu
                85                  90                  95

Ala Gly Thr Tyr Asp Tyr Tyr Cys Glu Pro His Arg Gly Ala Gly Met
            100                 105                 110

Val Gly Lys Val Val Val Asn
        115

<210> SEQ ID NO 56
<211> LENGTH: 235
<212> TYPE: PRT
<213> ORGANISM: Cricetulus griseus
<220> FEATURE:
<221> NAME/KEY: misc_feature
<223> OTHER INFORMATION: Ferritin, mitochondrial (Chinese hamster)

<400> SEQUENCE: 56

Met Leu Ser Gly Phe Trp Phe Phe Ser Lys His Ile Gly Pro Ala Leu
1               5                   10                  15

Met Ser Leu Pro Arg Val Leu His Arg Cys Thr Val Pro Gln Cys Leu
            20                  25                  30

Ala Ser Arg Tyr Pro Leu Leu Pro Ala Ser Pro Arg Arg Leu Leu Ala
        35                  40                  45

Ser Val Ala Ser Ser Gln Gly Ser Asp Gly Thr Ala Arg Val Arg His
    50                  55                  60

Asn Phe His Pro Asp Ser Glu Ala Ala Ile Asn His Gln Ile Asn Met
65                  70                  75                  80

Glu Leu Tyr Ala Ser Tyr Val Tyr Leu Ser Met Ala Tyr Tyr Phe Ser
                85                  90                  95

Arg Asp Asp Val Ala Leu Tyr Asn Phe Ser Lys Ser Phe Leu Arg Gln
            100                 105                 110

Ser Leu Glu Glu Arg Glu His Ala Glu Lys Leu Met Lys Leu Gln Asn
        115                 120                 125

Gln Arg Gly Gly Arg Ile Cys Leu Gln Asp Ile Lys Lys Pro Glu Gln
    130                 135                 140

Asp Asp Trp Glu Ser Gly Leu Arg Ala Met Glu Cys Ala Leu Leu Leu
145                 150                 155                 160

Glu Lys Ser Val Asn Gln Ser Leu Leu Asp Leu His Thr Leu Ala Ser
                165                 170                 175

Glu Lys Gly Asp Pro His Leu Cys Asp Phe Leu Glu Thr His Tyr Leu
            180                 185                 190

Asn Glu Gln Val Lys Ser Ile Lys Glu Leu Gly Asp His Val His Asn
        195                 200                 205

Leu Val Thr Met Gly Ala Pro Ala Val Gly Leu Ala Glu Tyr Leu Phe
    210                 215                 220

Asp Lys His Thr Leu Gly Ser Glu Ser Lys His
225                 230                 235

<210> SEQ ID NO 57
<211> LENGTH: 54
<212> TYPE: PRT
<213> ORGANISM: Pyrococcus furiosus
<220> FEATURE:
<221> NAME/KEY: misc_feature
<223> OTHER INFORMATION: Rubredoxin [Pyrococcus furiosus DSM 3638]

<400> SEQUENCE: 57

Met Ala Lys Trp Val Cys Lys Ile Cys Gly Tyr Ile Tyr Asp Glu Asp
1               5                   10                  15

Ala Gly Asp Pro Asp Asn Gly Ile Ser Pro Gly Thr Lys Phe Glu Glu
            20                  25                  30

Leu Pro Asp Asp Trp Val Cys Pro Ile Cys Gly Ala Pro Lys Ser Glu
        35                  40                  45

Phe Glu Lys Leu Glu Asp
    50

<210> SEQ ID NO 58
<211> LENGTH: 7
<212> TYPE: PRT
<213> ORGANISM: Artificial Sequence
<220> FEATURE:
<223> OTHER INFORMATION: Synthetic: Microperoxidase-8 (MP-8)

<400> SEQUENCE: 58

Ala Gln Cys His Thr Val Glu
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic: Microperoxidase-9 (MP-9)

<400> SEQUENCE: 59

Ala Gln Cys His Thr Val Glu Lys
1               5

<210> SEQ ID NO 60
<211> LENGTH: 10
<212> TYPE: PRT
<213> ORGANISM: Artificial Sequence
<220> FEATURE:
<223> OTHER INFORMATION: Synthetic: Microperoxidase-11 (MP-11)

<400> SEQUENCE: 60

Gln Lys Cys Ala Gln Cys His Thr Val Glu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic: glycine-serine flexible linker

<400> SEQUENCE: 61

Gly Ser Gly Gly Ser Gly Gly Ser Gly Gly Ser Gly
1               5                   10

<210> SEQ ID NO 62
<211> LENGTH: 333
<212> TYPE: DNA
<213> ORGANISM: Artificial Sequence
<220> FEATURE:
<223> OTHER INFORMATION: Synthetic: Stack 2 - Trp

<400> SEQUENCE: 62
ggtaataata gcggcccaaa ttctgagctg tggatttacc agtacggtgg cggtaactct      60
gcacttgctc tgcaaactga tgcccgtaac tctgacttgt ggattaccca gcatggcggc     120
ggtaatggtg cagatgttgg tcagggctca gatgacagct caatctggct gacccaacgt     180
ggcttcggta acagcgctac tcttgatcag tggaacggca aaaattctga aatgtgggtt     240

-continued

```
aaacagttcg gtggtggcaa cggtgctgca gttgaccaga ctgcatctaa ctcctccgtc    300
tgggtgactc aggttggctt tggtaacaac gcg                                 333

<210> SEQ ID NO 63
<211> LENGTH: 264
<212> TYPE: DNA
<213> ORGANISM: Artificial Sequence
<220> FEATURE:
<223> OTHER INFORMATION: Synthetic: Stack 3 - Trp

<400> SEQUENCE: 63
actgatgccc gtaactctga cttgactatt tggcagcatg gcggcggtaa tggtgcagat     60
gttggtcagg gctcagatga cagctcaatc gatctgtggc aacgtggctt cggtaacagc    120
gctactcttg atcagtggaa cggcaaaaat tctgaaatga cggtttggca gttcggtggt    180
ggcaacggtg ctgcagttga ccagactgca tctaactcct ccgtcaacgt gtggcaggtt    240
ggctttggta acaacgcgac cgct                                           264

<210> SEQ ID NO 64
<211> LENGTH: 330
<212> TYPE: DNA
<213> ORGANISM: Artificial Sequence
<220> FEATURE:
<223> OTHER INFORMATION: Synthetic: Stack 4 - Trp

<400> SEQUENCE: 64
taccagtacg gtggcggtaa ctctgcactt tggctgcaaa ctgatgcccg taactctgac     60
ttgactatta cccagcatgg cggcggtaat ggtgcatggg ttggtcaggg ctcagatgac    120
agctcaatcg atctgaccca cgtggcttc ggtaacagcg cttggcttga tcagtggaac    180
ggcaaaaatt ctgaaatgac ggttaaacag ttcggtggtg gcaacggtgc ttgggttgac    240
cagactgcat ctaactcctc cgtcaacgtg actcaggttg ctttggtaa caacgcgtgg    300 gctcatcagt acggctctgg tggctctggt                                     330

<210> SEQ ID NO 65
<211> LENGTH: 264
<212> TYPE: DNA
<213> ORGANISM: Artificial Sequence
<220> FEATURE:
<223> OTHER INFORMATION: Synthetic: Stack 5 - Trp

<400> SEQUENCE: 65
tacggtggcg gtaactctgc acttgctctg tggactgatg cccgtaactc tgacttgact     60
attacccagc atggcggcgg taatggtgca gatgtttggc agggctcaga tgacagctca    120
atcgatctga cccaacgtgg cttcggtaac agcgctactc tttggcagtg aacggcaaa    180 aattctgaaa tgacggttaa acagttcggt ggtggcaacg gtgctgcagt tggcagact    240 gcatctaact cctccgtcaa cgtg                                           264

<210> SEQ ID NO 66
<211> LENGTH: 243
<212> TYPE: DNA
<213> ORGANISM: Artificial Sequence
<220> FEATURE:
<223> OTHER INFORMATION: Synthetic: Microperoxidase-8 fusion

<400> SEQUENCE: 66
gtaacaacgc gaccgctcat cagtacggtg gatctggtag cagcggctct ggtggttctg     60
```

```
ggggcggaag tggctcctct gggagcgggg ggtcggtgg tggctcgggt tcatctggta      120
gtggcggttc gggttgcgcg cagtgccata ccgtggaagg ctctggtggc tctggtggct     180
ctggcggcag cgggcatcac caccaccatc attaatacat catttgtatt acagaaacag     240
ggc                                                                   243

<210> SEQ ID NO 67
<211> LENGTH: 245
<212> TYPE: DNA
<213> ORGANISM: Artificial Sequence
<220> FEATURE:
<223> OTHER INFORMATION: Synthetic: Microperoxidase-9 fusion

<400> SEQUENCE: 67
taacaacgcg accgctcatc agtacggtgg atctggtagc agcggctctg gtggttctgg      60
gggcggaagt ggctcctctg ggagcggggg gtcgggtggt ggctcgggtt catctggtag     120
tggcggttcg ggttgcgcgc agtgccatac cgtggaaaaa ggctctggtg gctctggtgg     180
ctctggcggc agcgggcatc accaccacca tcattaatac atcatttgta ttacagaaac     240
agggc                                                                 245

<210> SEQ ID NO 68
<211> LENGTH: 240
<212> TYPE: DNA
<213> ORGANISM: Artificial Sequence
<220> FEATURE:
<223> OTHER INFORMATION: Synthetic: Microperoxidase-11 fusion

<400> SEQUENCE: 68
acaacgcgac cgctcatcag tacggtggat ctggtagcag cggctctggt ggttctgggg      60
gcggaagtgg ctcctctggg agcgggggt cgggtggtgg ctcgggttca tctggtagtg     120
gcggttcggg tgtgcagaaa tgcgcgcagt gccataccgt ggaaggctct ggtggctctg     180
gtggctctgg cggcagcggg catcaccacc accatcatta atacatcatt tgtattacag     240

<210> SEQ ID NO 69
<211> LENGTH: 573
<212> TYPE: DNA
<213> ORGANISM: Artificial Sequence
<220> FEATURE:
<223> OTHER INFORMATION: Synthetic: Plastocyanin fusion

<400> SEQUENCE: 69
acaacgcgac cgctcatcag tacggtggat ctggtagcag cggctctggt ggttctgggg      60
gcggaagtgg ctcctctggg agcggggggt cgggtggtgg ctcgggttca tctggtagtg     120
gcggttcggg tatgatttcc tcgcttcgct cagcgctatc tgcatgtttt gcattgcttt     180
tggtgcttgc ctttggagtt gcatccgcac aagctaaaac agttgaagta aaactaggaa     240
ctgatgctgg aatgcttgca ttcgaaccca gctctgtaac cataagtact ggcgactctg     300
tgaagtttgt caacaacaaa cttgctcctc acaatgcagt ttttgaaggt catgaagaat     360
taagtcatcc tgaccttgct tttgctcctg gcgaaagctg gcaagaaact tttacagaag     420
caggtacata tgactattac tgcgagcctc atagaggagc agggatggtc gggaaagtag     480
ttgttaacgg ctctggtggc tctggtggct ctggcggcag cgggcatcac caccaccatc     540
attaatacat catttgtatt acagaaacag ggc                                  573

<210> SEQ ID NO 70
<211> LENGTH: 908
```

<210> SEQ ID NO 70
<211> LENGTH: 908
<212> TYPE: DNA
<213> ORGANISM: Artificial Sequence
<220> FEATURE:
<223> OTHER INFORMATION: Synthetic: Mitochondrial ferritin fusion

<400> SEQUENCE: 70

```
aacgcgaccg ctcatcagta cggtggatct ggtagcagcg gctctggtgg ttctggggc      60
ggaagtggct cctctgggag cgggggggtcg ggtggtggct cgggttcatc tggtagtggc   120
ggttcgggta tgctgtctgg tttctggttc ttctccaagc acatcggccc tgcattgatg   180
tccttgcccc gtgtgctaca caggtgcact gtcccacagt gtttggcctc aggtatcct    240
ttactacccg cctcccctcg acgtctgctg gcctcggtgg cctcctccca gggctctgat   300
ggaactgcca gggtgcgcca caactttcac ccagactctg aggcagccat caaccaccaa   360
atcaacatgg agctttacgc atcctacgtg tacctgtcca tggcctacta cttctccagg   420
gatgatgtgg ccttgtacaa cttctccaag tctttccttc gccagtcgct ggaggagagg   480
gagcatgcag agaagctaat gaagctgcag aaccaacgcg gaggccggat ctgcctccag   540
gatatcaaga agccagagca agatgactgg gagagcggac tgcgggccat ggaatgtgct   600
ctgctcctgg aaaagagtgt aaaccagtcg ctgctggacc tgcatactct ggcctcagaa   660
aaaggagatc tccatttgtg cgactttctg gaaacacact acctgaatga gcaggtgaag   720
tctatcaaag aattaggtga ccacgtgcac aacttagtca ccatggggggc tccagctgtt   780
ggcctagcgg agtacctttt tgacaagcac acccttggaa gtgagagcaa gcacggctct   840
ggtggctctg gtggctctgg cggcagcggg catcaccacc accatcatta atacatcatt   900
tgtattac                                                             908
```

<210> SEQ ID NO 71
<211> LENGTH: 376
<212> TYPE: DNA
<213> ORGANISM: Artificial Sequence
<220> FEATURE:
<223> OTHER INFORMATION: Synthetic: Rubredoxin fusion

<400> SEQUENCE: 71

```
aacgcgaccg ctcatcagta cggtggatct ggtagcagcg gctctggtgg ttctggggc      60
ggaagtggct cctctgggag cgggggggtcg ggtggtggct cgggttcatc tggtagtggc   120
ggttcgggta tggcaaagtg ggtttgtaag atatgcggat acatatatga tgaagatgca   180
ggagatccag acaatggtat ttctcctgga actaagtttg aggagctacc agatgattgg   240
gtttgcccca tttgtggggc tccaaaaagt gaatttgaaa agttagaaga tggctctggt   300
ggctctggtg gctctggcgg cagcgggcat caccaccacc atcattaata catcatttgt   360
attacagaaa cagggc                                                    376
```

<210> SEQ ID NO 72
<211> LENGTH: 169
<212> TYPE: PRT
<213> ORGANISM: Artificial Sequence
<220> FEATURE:
<223> OTHER INFORMATION: Synthetic: Stack 2 Trp

<400> SEQUENCE: 72

```
Met Lys Leu Leu Lys Val Ala Ala Ile Ala Ala Ile Val Phe Ser Gly
1               5                   10                  15
Ser Ala Leu Ala Gly Val Val Pro Gln Tyr Gly Gly Gly Gly Asn His
            20                  25                  30
```

Gly Gly Gly Gly Asn Asn Ser Gly Pro Asn Ser Glu Leu Trp Ile Tyr
            35                  40                  45

Gln Tyr Gly Gly Gly Asn Ser Ala Leu Ala Leu Gln Thr Asp Ala Arg
 50                  55                  60

Asn Ser Asp Leu Trp Ile Thr Gln His Gly Gly Gly Asn Gly Ala Asp
 65                  70                  75                  80

Val Gly Gln Gly Ser Asp Asp Ser Ser Ile Trp Leu Thr Gln Arg Gly
                 85                  90                  95

Phe Gly Asn Ser Ala Thr Leu Asp Gln Trp Asn Gly Lys Asn Ser Glu
                100                 105                 110

Met Trp Val Lys Gln Phe Gly Gly Asn Gly Ala Ala Val Asp Gln
            115                 120                 125

Thr Ala Ser Asn Ser Ser Val Trp Val Thr Gln Val Gly Phe Gly Asn
            130                 135                 140

Asn Ala Thr Ala His Gln Tyr Gly Ser Gly Gly Ser Gly Gly Ser Gly
145                 150                 155                 160

Gly Ser Gly His His His His His His
            165

<210> SEQ ID NO 73
<211> LENGTH: 169
<212> TYPE: PRT
<213> ORGANISM: Artificial Sequence
<220> FEATURE:
<223> OTHER INFORMATION: Synthetic: Stack 3  Trp

<400> SEQUENCE: 73

Met Lys Leu Leu Lys Val Ala Ala Ile Ala Ala Ile Val Phe Ser Gly
 1               5                  10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
 50                  55                  60

Asn Ser Asp Leu Thr Ile Trp Gln His Gly Gly Gly Asn Gly Ala Asp
 65                  70                  75                  80

Val Gly Gln Gly Ser Asp Asp Ser Ser Ile Asp Leu Trp Gln Arg Gly
                 85                  90                  95

Phe Gly Asn Ser Ala Thr Leu Asp Gln Trp Asn Gly Lys Asn Ser Glu
                100                 105                 110

Met Thr Val Trp Gln Phe Gly Gly Gly Asn Gly Ala Ala Val Asp Gln
            115                 120                 125

Thr Ala Ser Asn Ser Ser Val Asn Val Trp Gln Val Gly Phe Gly Asn
            130                 135                 140

Asn Ala Thr Ala His Gln Tyr Gly Ser Gly Gly Ser Gly Gly Ser Gly
145                 150                 155                 160

Gly Ser Gly His His His His His His
            165

<210> SEQ ID NO 74
<211> LENGTH: 169
<212> TYPE: PRT
<213> ORGANISM: Artificial Sequence
<220> FEATURE:
<223> OTHER INFORMATION: Synthetic: Stack 4  Trp

<400> SEQUENCE: 74

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
                20              25                  30

Gly Gly Gly Gly Asn Asn Ser Gly Pro Asn Ser Glu Leu Asn Ile Tyr
            35              40                  45

Gln Tyr Gly Gly Asn Ser Ala Leu Trp Leu Gln Thr Asp Ala Arg
    50              55                  60

Asn Ser Asp Leu Thr Ile Thr Gln His Gly Gly Asn Gly Ala Trp
65              70              75                  80

Val Gly Gln Gly Ser Asp Asp Ser Ser Ile Asp Leu Thr Gln Arg Gly
                85                  90                  95

Phe Gly Asn Ser Ala Trp Leu Asp Gln Trp Asn Gly Lys Asn Ser Glu
            100                 105                 110

Met Thr Val Lys Gln Phe Gly Gly Asn Gly Ala Trp Val Asp Gln
                115                 120                 125

Thr Ala Ser Asn Ser Ser Val Asn Val Thr Gln Val Gly Phe Gly Asn
    130                 135                 140

Asn Ala Trp Ala His Gln Tyr Gly Ser Gly Gly Ser Gly Gly Ser Gly
145                 150                 155                 160

Gly Ser Gly His His His His His His
                165
```

<210> SEQ ID NO 75
<211> LENGTH: 169
<212> TYPE: PRT
<213> ORGANISM: Artificial Sequence
<220> FEATURE:
<223> OTHER INFORMATION: Synthetic: Stack 5 - Trp

<400> SEQUENCE: 75

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
                20              25                  30

Gly Gly Gly Gly Asn Asn Ser Gly Pro Asn Ser Glu Leu Asn Ile Tyr
            35              40                  45

Gln Tyr Gly Gly Asn Ser Ala Leu Ala Leu Trp Thr Asp Ala Arg
    50              55                  60

Asn Ser Asp Leu Thr Ile Thr Gln His Gly Gly Gly Asn Gly Ala Asp
65              70              75                  80

Val Trp Gln Gly Ser Asp Asp Ser Ser Ile Asp Leu Thr Gln Arg Gly
                85                  90                  95

Phe Gly Asn Ser Ala Thr Leu Trp Gln Trp Asn Gly Lys Asn Ser Glu
            100                 105                 110

Met Thr Val Lys Gln Phe Gly Gly Gly Asn Gly Ala Ala Val Trp Gln
                115                 120                 125

Thr Ala Ser Asn Ser Ser Val Asn Val Thr Gln Val Gly Phe Gly Asn
    130                 135                 140

Asn Ala Thr Ala His Gln Tyr Gly Ser Gly Gly Ser Gly Gly Ser Gly
145                 150                 155                 160

Gly Ser Gly His His His His His His
                165
```

<210> SEQ ID NO 76

<211> LENGTH: 213
<212> TYPE: PRT
<213> ORGANISM: Artificial Sequence
<220> FEATURE:
<223> OTHER INFORMATION: Synthetic: Microperoxidase-8 fusion

<400> SEQUENCE: 76

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr Gly Gly Ser Gly Ser Ser Gly Ser Gly
145                 150                 155                 160

Gly Ser Gly Gly Gly Ser Gly Ser Gly Ser Gly Ser Gly Ser Gly Gly
                165                 170                 175

Gly Ser Gly Ser Ser Gly Ser Gly Gly Ser Gly Cys Ala Gln Cys His
            180                 185                 190

Thr Val Glu Gly Ser Gly Gly Ser Gly Gly Ser Gly Gly Ser Gly His
        195                 200                 205

His His His His
    210

<210> SEQ ID NO 77
<211> LENGTH: 214
<212> TYPE: PRT
<213> ORGANISM: Artificial Sequence
<220> FEATURE:
<223> OTHER INFORMATION: Synthetic: Microperoxidase-9 fusion

<400> SEQUENCE: 77

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu

```
                    100                 105                 110
Met Thr Val Lys Gln Phe Gly Gly Gly Asn Gly Ala Ala Val Asp Gln
            115                 120                 125

Thr Ala Ser Asn Ser Ser Val Asn Val Thr Gln Val Gly Phe Gly Asn
            130                 135             140

Asn Ala Thr Ala His Gln Tyr Gly Gly Ser Gly Ser Ser Gly Ser Gly
145                 150                 155                 160

Gly Ser Gly Gly Gly Ser Gly Ser Ser Gly Ser Gly Gly Ser Gly Gly
                165                 170                 175

Gly Ser Gly Ser Ser Gly Ser Gly Gly Ser Gly Cys Ala Gln Cys His
            180                 185                 190

Thr Val Glu Lys Gly Ser Gly Gly Ser Gly Gly Ser Gly Gly Ser Gly
            195                 200                 205

His His His His His His
        210
```

<210> SEQ ID NO 78
<211> LENGTH: 216
<212> TYPE: PRT
<213> ORGANISM: Artificial Sequence
<220> FEATURE:
<223> OTHER INFORMATION: Synthetic: Microperoxidase-11 fusion

<400> SEQUENCE: 78

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr Gly Gly Ser Gly Ser Ser Gly Ser Gly
145                 150                 155                 160

Gly Ser Gly Gly Gly Ser Gly Ser Ser Gly Ser Gly Gly Ser Gly Gly
                165                 170                 175

Gly Ser Gly Ser Ser Gly Ser Gly Gly Ser Gly Val Gln Lys Cys Ala
            180                 185                 190

Gln Cys His Thr Val Glu Gly Ser Gly Gly Ser Gly Gly Ser Gly Gly
        195                 200                 205

Ser Gly His His His His His His
    210                 215
```

<210> SEQ ID NO 79
<211> LENGTH: 324
<212> TYPE: PRT

<213> ORGANISM: Artificial Sequence
<220> FEATURE:
<223> OTHER INFORMATION: Synthetic: Plastocyanin fusion

<400> SEQUENCE: 79

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Asn Gly Ala Asp
65              70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Asn Gly Ala Ala Val Asp Gln
            115                 120                 125

Thr Ala Ser Asn Ser Ser Val Asn Val Thr Gln Val Gly Phe Gly Asn
    130                 135                 140

Asn Ala Thr Ala His Gln Tyr Gly Gly Ser Gly Ser Ser Gly Ser Gly
145                 150                 155                 160

Gly Ser Gly Gly Gly Ser Gly Ser Ser Gly Ser Gly Gly Ser Gly Gly
                165                 170                 175

Gly Ser Gly Ser Ser Gly Ser Gly Gly Ser Gly Met Ile Ser Ser Leu
            180                 185                 190

Arg Ser Ala Leu Ser Ala Cys Phe Ala Leu Leu Val Leu Ala Phe
    195                 200                 205

Gly Val Ala Ser Ala Gln Ala Lys Thr Val Glu Val Lys Leu Gly Thr
    210                 215                 220

Asp Ala Gly Met Leu Ala Phe Glu Pro Ser Ser Val Thr Ile Ser Thr
225                 230                 235                 240

Gly Asp Ser Val Lys Phe Val Asn Asn Lys Leu Ala Pro His Asn Ala
                245                 250                 255

Val Phe Glu Gly His Glu Glu Leu Ser His Pro Asp Leu Ala Phe Ala
            260                 265                 270

Pro Gly Glu Ser Trp Gln Glu Thr Phe Thr Glu Ala Gly Thr Tyr Asp
            275                 280                 285

Tyr Tyr Cys Glu Pro His Arg Gly Ala Gly Met Val Gly Lys Val Val
    290                 295                 300

Val Asn Gly Ser Gly Gly Ser Gly Gly Ser Gly His His
305                 310                 315                 320

His His His His
```

<210> SEQ ID NO 80
<211> LENGTH: 440
<212> TYPE: PRT
<213> ORGANISM: Artificial Sequence
<220> FEATURE:
<223> OTHER INFORMATION: Synthetic: Mitochondrial ferritin fusion

<400> SEQUENCE: 80

Met Lys Leu Leu Lys Val Ala Ala Ile Ala Ala Ile Val Phe Ser Gly

-continued

```
1               5                   10                  15
Ser Ala Leu Ala Gly Val Val Pro Gln Tyr Gly Gly Gly Asn His
                20                  25                  30
Gly Gly Gly Gly Asn Asn Ser Gly Pro Asn Ser Glu Leu Asn Ile Tyr
                35                  40                  45
Gln Tyr Gly Gly Gly Asn Ser Ala Leu Ala Leu Gln Thr Asp Ala Arg
         50                  55                  60
Asn Ser Asp Leu Thr Ile Thr Gln His Gly Gly Asn Gly Ala Asp
 65                  70                  75                  80
Val Gly Gln Gly Ser Asp Asp Ser Ser Ile Asp Leu Thr Gln Arg Gly
                 85                  90                  95
Phe Gly Asn Ser Ala Thr Leu Asp Gln Trp Asn Gly Lys Asn Ser Glu
                100                 105                 110
Met Thr Val Lys Gln Phe Gly Gly Asn Gly Ala Ala Val Asp Gln
                115                 120                 125
Thr Ala Ser Asn Ser Ser Val Asn Val Thr Gln Val Gly Phe Gly Asn
        130                 135                 140
Asn Ala Thr Ala His Gln Tyr Gly Gly Ser Gly Ser Ser Gly Ser Gly
145                 150                 155                 160
Gly Ser Gly Gly Gly Ser Gly Ser Ser Gly Ser Gly Gly Ser Gly Gly
                165                 170                 175
Gly Ser Gly Ser Ser Gly Ser Gly Gly Ser Gly Met Leu Ser Gly Phe
                180                 185                 190
Trp Phe Phe Ser Lys His Ile Gly Pro Ala Leu Met Ser Leu Pro Arg
                195                 200                 205
Val Leu His Arg Cys Thr Val Pro Gln Cys Leu Ala Ser Arg Tyr Pro
                210                 215                 220
Leu Leu Pro Ala Ser Pro Arg Arg Leu Leu Ala Ser Val Ala Ser Ser
225                 230                 235                 240
Gln Gly Ser Asp Gly Thr Ala Arg Val Arg His Asn Phe His Pro Asp
                245                 250                 255
Ser Glu Ala Ala Ile Asn His Gln Ile Asn Met Glu Leu Tyr Ala Ser
                260                 265                 270
Tyr Val Tyr Leu Ser Met Ala Tyr Tyr Phe Ser Arg Asp Asp Val Ala
            275                 280                 285
Leu Tyr Asn Phe Ser Lys Ser Phe Leu Arg Gln Ser Leu Glu Glu Arg
            290                 295                 300
Glu His Ala Glu Lys Leu Met Lys Leu Gln Asn Gln Arg Gly Gly Arg
305                 310                 315                 320
Ile Cys Leu Gln Asp Ile Lys Lys Pro Glu Gln Asp Asp Trp Glu Ser
                325                 330                 335
Gly Leu Arg Ala Met Glu Cys Ala Leu Leu Glu Lys Ser Val Asn
                340                 345                 350
Gln Ser Leu Leu Asp Leu His Thr Leu Ala Ser Glu Lys Gly Asp Pro
            355                 360                 365
His Leu Cys Asp Phe Leu Glu Thr His Tyr Leu Asn Glu Gln Val Lys
        370                 375                 380
Ser Ile Lys Glu Leu Gly Asp His Val His Asn Leu Val Thr Met Gly
385                 390                 395                 400
Ala Pro Ala Val Gly Leu Ala Glu Tyr Leu Phe Asp Lys His Thr Leu
                405                 410                 415
Gly Ser Glu Ser Lys His Gly Ser Gly Gly Ser Gly Gly Ser Gly Gly
                420                 425                 430
```

Ser Gly His His His His His His
        435                 440

<210> SEQ ID NO 81
<211> LENGTH: 259
<212> TYPE: PRT
<213> ORGANISM: Artificial Sequence
<220> FEATURE:
<223> OTHER INFORMATION: Synthetic: Rubredoxin fusion

<400> SEQUENCE: 81

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr Gly Gly Ser Gly Ser Gly Ser Gly
145                 150                 155                 160

Gly Ser Gly Gly Ser Gly Ser Ser Gly Ser Gly Gly Ser Gly Gly
                165                 170                 175

Gly Ser Gly Ser Ser Gly Ser Gly Gly Ser Gly Met Ala Lys Trp Val
            180                 185                 190

Cys Lys Ile Cys Gly Tyr Ile Tyr Asp Glu Asp Ala Gly Asp Pro Asp
        195                 200                 205

Asn Gly Ile Ser Pro Gly Thr Lys Phe Glu Glu Leu Pro Asp Asp Trp
    210                 215                 220

Val Cys Pro Ile Cys Gly Ala Pro Lys Ser Glu Phe Glu Lys Leu Glu
225                 230                 235                 240

Asp Gly Ser Gly Gly Ser Gly Gly Ser Gly His His His
                245                 250                 255

His His His

<210> SEQ ID NO 82
<211> LENGTH: 34
<212> TYPE: DNA
<213> ORGANISM: Artificial Sequence
<220> FEATURE:
<223> OTHER INFORMATION: Synthetic: Fwd primer

<400> SEQUENCE: 82
gtgactcagg ttggctttgg taacaacgcg accg      34

<210> SEQ ID NO 83
<211> LENGTH: 30

```
<212> TYPE: DNA
<213> ORGANISM: Artificial Sequence
<220> FEATURE:
<223> OTHER INFORMATION: Synthetic: Rev primer

<400> SEQUENCE: 83
gaatttgggc cgctattatt accgccacca                                      30

<210> SEQ ID NO 84
<211> LENGTH: 36
<212> TYPE: DNA
<213> ORGANISM: Artificial Sequence
<220> FEATURE:
<223> OTHER INFORMATION: Synthetic: Fwd primer

<400> SEQUENCE: 84
caggttggct ttggtaacaa cgcgaccgct catcag                               36

<210> SEQ ID NO 85
<211> LENGTH: 30
<212> TYPE: DNA
<213> ORGANISM: Artificial Sequence
<220> FEATURE:
<223> OTHER INFORMATION: Synthetic: Rev primer

<400> SEQUENCE: 85
tagtcaagtc agagttacgg gcatcagttt                                      30

<210> SEQ ID NO 86
<211> LENGTH: 30
<212> TYPE: DNA
<213> ORGANISM: Artificial Sequence
<220> FEATURE:
<223> OTHER INFORMATION: Synthetic: Fwd primer

<400> SEQUENCE: 86
cagtacggct ctggtggctc tggtggctct                                      30

<210> SEQ ID NO 87
<211> LENGTH: 28
<212> TYPE: DNA
<213> ORGANISM: Artificial Sequence
<220> FEATURE:
<223> OTHER INFORMATION: Synthetic: Rev primer

<400> SEQUENCE: 87
aagtgcagag ttaccgccac cgtactgg                                        28

<210> SEQ ID NO 88
<211> LENGTH: 30
<212> TYPE: DNA
<213> ORGANISM: Artificial Sequence
<220> FEATURE:
<223> OTHER INFORMATION: Synthetic: Fwd primer

<400> SEQUENCE: 88
gactgcatct aactcctccg tcaacgtgac                                      30

<210> SEQ ID NO 89
<211> LENGTH: 36
<212> TYPE: DNA
<213> ORGANISM: Artificial Sequence
<220> FEATURE:
<223> OTHER INFORMATION: Synthetic: Fwd primer

<400> SEQUENCE: 89
```

```
caggttggct ttggtaacaa cgcgaccgct catcag                                36

<210> SEQ ID NO 90
<211> LENGTH: 18
<212> TYPE: PRT
<213> ORGANISM: Artificial Sequence
<220> FEATURE:
<223> OTHER INFORMATION: Synthetic: Ser-X5-Gln-X4-Asn-X5-Gln motif
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid

<400> SEQUENCE: 90

Ser Xaa Xaa Xaa Xaa Xaa Gln Xaa Xaa Xaa Xaa Asn Xaa Xaa Xaa Xaa
1               5                   10                  15

Xaa Gln
```

ELECTRICALLY CONDUCTIVE PROTEIN NANOFIBERS AND BIOFILMS

RELATED APPLICATIONS

This application is a 35 U.S.C. § 371 national stage filing of International Application No. PCT/US2016/062743, filed on Nov. 18, 2016, which claims priority to U.S. Provisional Application No. 62/257,441, filed on Nov. 19, 2015, and U.S. Provisional Application No. 62/338,715, filed May 19, 2016, the entire contents of each of which are expressly incorporated herein by reference.

STATEMENT OF GOVERNMENT INTERESTS

This invention was made with Government support under W911NF-13-1-0242 awarded by the U.S. Army Research Office and under 1410751 awarded by the National Science Foundation. The Government has certain rights in this invention.

SEQUENCE LISTING

The instant application contains a Sequence Listing which has been submitted electronically in ASCII format and is hereby incorporated by reference in its entirety. Said ASCII copy, created on Nov. 17, 2016, is named 117823-13220_SeqLst.TXT and is 64 kilobytes in size.

FIELD

The technology described herein relates to engineered protein-based materials, nanofibers, and biofilms from bacterial amyloid structures known as curli fibers that are capable of mediating long-range electron transport.

BACKGROUND

Protein-based materials capable of mediating long-range electron transport have been investigated for their use in a wide range of modern optoelectronic technologies, including biosensors, light harvesting systems, microbial fuel cells, electrobiosynthetic devices, and other electronic devices. See Pant, D. et al. Bioelectrochemical systems (BES) for sustainable energy production and product recovery from organic wastes and industrial wastewaters. *RSC Adv.* 2, 1248-63 (2012). These materials can be classified into two categories with complementary advantages—naturally occurring systems and engineered biomolecular systems. Naturally occurring systems, like the conductive biofilms of *Geobacter sulfurreducens* and *Shewanella oneidensis* are useful for their ability to convert energy stored in chemical bonds into electrical energy (i.e., microbial fuel cells) and vice versa (i.e., electrobiosynthesis). Pant, D. et al. Bioelectrochemical systems (BES) for sustainable energy production and product recovery from organic wastes and industrial wastewaters. *RSC Adv.* 2, 1248-1263 (2012); Erable, B., Duteanu, N. M., Ghangrekar, M. M., Dumas, C. & Scott, K. Application of electroactive biofilms. *Biofouling* 26, 57-71 (2010); Michener, J. K., Thodey, K., Liang, J. C. & Smolke, C. D. Applications of genetically-encoded biosensors for the construction and control of biosynthetic pathways. *Metabolic Engineering* 14, 212-222 (2012). In order to mediate electron transfer to and from electrodes, these organisms have evolved highly specialized extracellular appendages containing periodically spaced chemical groups that facilitate electron transport. Vargas, M. et al. Aromatic Amino Acids Required for Pili Conductivity and Long-Range Extracellular Electron Transport in *Geobacter sulfurreducens*. *mBio* 4, e00105-13-e00105-13 (2013); Pirbadian, S. et al. *Shewanella oneidensis* MR-1 nanowires are outer membrane and periplasmic extensions of the extracellular electron transport components. *Proceedings of the National Academy of Sciences* 111, 12883-12888 (2014). However, despite their considerable advantages, these naturally occurring systems can be difficult to improve upon using rational design due to inherent difficulties in genetically engineering the host organisms, a lack of structural information regarding their conductive extracellular appendages, and their confinement to the use of naturally occurring amino acids as functional groups.

SUMMARY

In one aspect, provided herein is a method of producing a genetically modified bacterium comprising genetically altering a bacterium to include a nucleic acid sequence encoding a mutant amyloid polypeptide having a series of aligned aromatic groups, wherein the nucleic acid sequence is under the control of a promoter to express the mutant amyloid polypeptide.

In another aspect, provided herein is a method of producing a genetically modified bacterium comprising genetically altering a bacterium to include a nucleic acid sequence encoding a fusion protein comprising an amyloid polypeptide fused to a redox active domain, wherein the nucleic acid sequence is under the control of a promoter to express the fusion protein.

In one embodiment, the the amyloid polypeptide is selected from the group consisting of CsgA, CspA, a beta-lactoglobulin, a lysozyme, Sup35, and an amyloid-beta peptide. In one embodiment, the amyloid polypeptide is CsgA.

In one embodiment, the redox active domain is selected from the group consisting of: a metalloprotein, a redox enzyme, a binding domain, and a stimuli-responsive peptide. In one embodiment, the redox active domain is selected from the group consisting of: plastocyanin, an oxygen-carrier protein, a microperoxidase, a cytochrome, a copper-binding protein, an iron-binding protein, a gold-binding domain, a metalloenzyme, rubredoxin, and a fragment thereof. In one embodiment, the redox active domain comprises plastocyanin or a fragment thereof. In one embodiment, the redox active domain comprises rubredoxin or a fragment thereof.

In one embodiment, the bacterium is *E. coli*. In one embodiment, the bacterium is non-pathogenic.

In one embodiment, the aromatic group is present on a standard amino acid or a nonstandard amino acid. In one embodiment, the aromatic group is present on a standard amino acid selected from the group consisting of phenylalanine, tryptophan, tyrosine and histidine. In one embodiment, the aromatic group is present on a nonstandard amino acid selected from the group consisting of 2-thienylalanine, 3-thienylalanine, acetylphenylalanine and azidophenylalanine.

In one embodiment, the mutant amyloid polypeptide further comprises a redox active domain.

In one embodiment, the methods described herein further provide genetically altering the bacterium to include second nucleic acid sequence encoding a fusion protein comprising an amyloid polypeptide fused to a redox active domain. In one embodiment, the amyloid polypeptide is selected from the group consisting of CsgA, CspA, a beta-lactoglobulin, a lysozyme, Sup35, and an amyloid-beta peptide. In one embodiment, the redox active domain is selected from the group consisting of: a metalloprotein, a redox enzyme, a binding domain, and a stimuli-responsive peptide. In one embodiment, the redox active domain is selected from the group consisting of: plastocyanin, an oxygen-carrier protein, a microperoxidase, a cytochrome, a copper-binding protein, an iron-binding protein, a gold-binding domain, a metalloenzyme, rubredoxin, and a fragment thereof. In one embodiment, the redox active domain comprises plastocyanin or a fragment thereof. In one embodiment, the redox active domain comprises rubredoxin or a fragment thereof.

In another aspect, provided herein is a method of making an electrically conductive biofilm comprising proliferating a genetically-altered bacterium comprising a nucleic acid sequence encoding a mutant amyloid polypeptide having a series of aligned aromatic groups, to produce a population of genetically-altered bacteria expressing the nucleic acid sequence, and allowing the bacteria to form a biofilm comprising an amyloid-based structure formed from a plurality of mutant amyloid polypeptides, wherein the amyloid-based structure comprises a series of aligned aromatic groups forming electrically conductive pi-pi stacking along the length of the amyloid-based structure. In one embodiment, the amyloid-based structure comprises a curli fiber.

In yet another aspect, provided herein is a method of making an electrically conductive biofilm comprising proliferating a genetically-altered bacterium comprising a nucleic acid sequence encoding a fusion protein, wherein the fusion protein comprises an amyloid polypeptide fused to a redox active domain, to produce a population of genetically-altered bacteria expressing the nucleic acid sequence, and allowing the bacteria to form a biofilm comprising an amyloid-based structure formed from a plurality of fusion proteins, wherein the amyloid-based structure comprises a network of metal centers that mediate electron hopping between the metal centers. In one embodiment, the amyloid-based structure comprises a curli fiber.

In one embodiment, the amyloid polypeptide is selected from the group consisting of CsgA, CspA, a beta-lactoglobulin, a lysozyme, Sup35, and an amyloid-beta peptide. In one embodiment, the amyloid polypeptide is CsgA.

In one embodiment, the redox active domain is selected from the group consisting of a metalloprotein, a redox enzyme, a binding domain, and a stimuli-responsive peptide. In one embodiment, the redox active domain is selected from the group consisting of plastocyanin, an oxygen-carrier protein, a microperoxidase, a cytochrome, a copper-binding protein, an iron-binding protein, a gold-binding domain, a metalloenzyme, rubredoxin, and a fragment thereof. In one embodiment, the redox active domain comprises plastocyanin or a fragment thereof. In one embodiment, the redox active domain comprises rubredoxin or a fragment thereof.

In one embodiment, the bacterium is *E. coli*. In one embodiment, the bacterium is non-pathogenic.

In one embodiment, the aromatic group is present on a standard amino acid or a nonstandard amino acid. In one embodiment, the aromatic group is present on a standard amino acid selected from the group consisting of phenylalanine, tryptophan, tyrosine and histidine. In one embodiment, the aromatic group is present on a nonstandard amino acid selected from the group consisting of 2-thienylalanine, 3-thienylalanine, acetylphenylalanine and azidophenylalanine.

In one embodiment, the genetically modified bacterium further comprises a second nucleic acid sequence encoding a fusion protein comprising an amyloid polypeptide fused to a redox active domain.

In one embodiment, the aligned aromatic groups form a pi-pi stack aligned in a geometric configuration selected from the group consisting of sandwich-type pi-stacks, t-shaped pi-stacks, parallel-displaced pi-stacks.

In one aspect, provided herein is a method of making an electrically conductive amyloid-based structure from a genetically-modified bacterium comprising proliferating a genetically-altered bacterium, wherein the genetically-altered bacterium comprises a nucleic acid sequence encoding a mutant amyloid polypeptide having a series of aligned aromatic groups, to produce a population of genetically-altered bacteria expressing the nucleic acid sequence, and allowing the population of genetically-altered bacteria to produce an amyloid-based structure formed from a plurality of the mutant amyloid polypeptides, wherein the amyloid-based structure comprises a series of aligned aromatic groups forming electrically conductive pi-pi stacking along the length of the amyloid-based structures. In one embodiment, the amyloid-based structure comprises a curli fiber.

In another aspect, provided herein is a method of making an electrically conductive amyloid-based structure from a genetically-modified bacterium comprising proliferating a genetically-altered bacterium comprising a nucleic acid sequence encoding a fusion protein comprising an amyloid polypeptide fused to a redox active domain, to produce a population of genetically-altered bacteria expressing the nucleic acid sequence, allowing the population of genetically-altered bacteria to produce an amyloid-based structure formed from a plurality of the fusion proteins, wherein the amyloid-based structure comprises a network of metal centers that mediate electron hopping between the metal centers. In one embodiment, the amyloid-based structure comprises a curli fiber.

In one embodiment, the amyloid polypeptide is selected from the group consisting of CsgA, CspA, a beta-lactoglobulin, a lysozyme, Sup35, and an amyloid-beta peptide. In one embodiment, the amyloid polypeptide is CsgA.

In one embodiment, the redox active domain is selected from the group consisting of a metalloprotein, a redox enzyme, a binding domain, and a stimuli-responsive peptide. In one embodiment, the redox active domain is selected from the group consisting of plastocyanin, an oxygen-carrier protein, a microperoxidase, a cytochrome, a copper-binding protein, an iron-binding protein, a gold-binding domain, a metalloenzyme, rubredoxin, and a fragment thereof. In one embodiment, the redox active domain comprises plastocyanin or a fragment thereof. In one embodiment, the redox active domain comprises rubredoxin or a fragment thereof.

In one embodiment, the bacterium is *E. coli*. In one embodiment, the bacterium is non-pathogenic.

In one embodiment, the aromatic group is present on a standard amino acid or a nonstandard amino acid. In one embodiment, the aromatic group is present on a standard amino acid selected from the group consisting of phenylalanine, tryptophan, tyrosine and histidine. In one embodiment, the aromatic group is present on a nonstandard amino acid selected from the group consisting of 2-thienylalanine, 3-thienylalanine, acetylphenylalanine and azidophenylalanine.

In one embodiment, the genetically-modified bacterium further comprises a second nucleic acid sequence encoding a fusion protein comprising an amyloid polypeptide fused to a redox active domain.

In one aspect, provided herein is a genetically-modified bacterium comprising a nucleic acid sequence encoding a mutant amyloid protein having a series of aligned aromatic groups, wherein the nucleic acid sequence is under the control of a promoter to express the mutant amyloid protein.

In another aspect, provided herein is a genetically-modified bacterium comprising a nucleic acid sequence encoding a fusion protein comprising an amyloid polypeptide fused to a redox active domain, wherein the nucleic acid sequence is under the control of a promoter to express the fusion protein.

In yet another aspect, provided herein is a non-naturally occurring mutant amyloid polypeptide having a series of aligned aromatic groups.

In one embodiment, the amyloid polypeptide is selected from the group consisting of CsgA, CspA, a beta-lactoglobulin, a lysozyme, Sup35, and an amyloid-beta peptide. In one embodiment, the amyloid polypeptide is CsgA.

In one embodiment, the aromatic group is present on a standard amino acid or a nonstandard amino acid. In one embodiment, the aromatic group is present on a standard amino acid selected from the group consisting of phenylalanine, tryptophan, tyrosine and histidine. In one embodiment, the aromatic group is present on a nonstandard amino acid selected from the group consisting of 2-thienylalanine, 3-thienylalanine, acetylphenylalanine and azidophenylalanine.

In one embodiment, the mutant amyloid polypeptide further comprises a redox active domain. In one embodiment, the redox active domain is selected from the group consisting of a metalloprotein, a redox enzyme, a binding domain, and a stimuli-responsive peptide. In one embodiment, the redox active domain is selected from the group consisting of plastocyanin, an oxygen-carrier protein, a microperoxidase, a cytochrome, a copper-binding protein, an iron-binding protein, a gold-binding domain, a metalloenzyme, rubredoxin, and a fragment thereof. In one embodiment, the redox active domain comprises plastocyanin or a fragment thereof. In one embodiment, the redox active domain comprises rubredoxin or a fragment thereof.

In another aspect, provided herein is a fusion protein comprising an amyloid polypeptide fused to a redox active domain. In one embodiment, the amyloid polypeptide is selected from the group consisting of CsgA, CspA, a beta-lactoglobulin, a lysozyme, Sup35, and an amyloid-beta peptide. In one embodiment, the amyloid polypeptide is CsgA.

In one embodiment, the redox active domain is selected from the group consisting of a metalloprotein, a redox enzyme, a binding domain, and a stimuli-responsive peptide. In one embodiment, the redox active domain is selected from the group consisting of plastocyanin, an oxygen-carrier protein, a microperoxidase, a cytochrome, a copper-binding protein, an iron-binding protein, a gold-binding domain, a metalloenzyme, rubredoxin, and a fragment thereof. In one embodiment, the redox active domain comprises plastocyanin or a fragment thereof. In one embodiment, the redox active domain comprises rubredoxin or a fragment thereof.

In one embodiment, the amyloid polypeptide comprises a series of aligned aromatic groups. In one embodiment, the aromatic group is present on a standard amino acid or a nonstandard amino acid.

In one embodiment, the aromatic group is present on a standard amino acid selected from the group consisting of phenylalanine, tryptophan, tyrosine and histidine. In one embodiment, the aromatic group is present on a nonstandard amino acid selected from the group consisting of 2-thienylalanine, 3-thienylalanine, acetylphenylalanine and azidophenylalanine.

In one aspect, provided herein is a non-naturally occurring amyloid-based structure formed from a plurality of non-naturally occurring mutant amyloid polypeptides having a series of aligned aromatic groups, wherein the amyloid-based structure has a series of aligned aromatic groups forming electrically conductive pi-pi stacking along the length of the amyloid-based structure. In one embodiment, the amyloid-based structure comprises a curli fiber.

In another aspect, provided herein is a non-naturally occurring amyloid-based structure formed from a plurality of fusion proteins comprising an amyloid polypeptide fused to a redox active domain, wherein the amyloid-based structure comprises a network of metal centers that mediate electron hopping between the metal centers. In one embodiment, the amyloid-based structure comprises a curli fiber.

In yet another aspect, provided herein is a biofilm comprising a non-naturally occurring amyloid-based structure described herein. In one embodiment, the amyloid-based structure comprises a curli fiber.

In one aspect, provided herein is a nucleic acid sequence encoding a mutant amyloid polypeptide described herein.

In another aspect, provided herein is a nucleic acid sequence encoding a fusion protein described herein.

In one aspect, provided herein is a nucleic acid sequence encoding a non-naturally occurring mutant amyloid polypeptide having a series of aligned aromatic groups.

In one embodiment, the amyloid polypeptide is selected from the group consisting of CsgA, CspA, a beta-lactoglobulin, a lysozyme, Sup35, and an amyloid-beta peptide.

In one embodiment, the aromatic group is present on a standard amino acid or a nonstandard amino acid. In one embodiment, the aromatic group is present on a standard amino acid selected from the group consisting of phenylalanine, tryptophan, tyrosine and histidine. In one embodiment, the aromatic group is present on a nonstandard amino acid selected from the group consisting of 2-thienylalanine, 3-thienylalanine, acetylphenylalanine and azidophenylalanine.

In one embodiment, the amyloid polypeptide further comprising a redox active domain. In one embodiment, the redox active domain is selected from the group consisting of a metalloprotein, a redox enzyme, a binding domain, and a stimuli-responsive peptide. In one embodiment, the redox active domain is selected from the group consisting of plastocyanin, an oxygen-carrier protein, a microperoxidase, a cytochrome, a copper-binding protein, an iron-binding protein, a gold-binding domain, a metalloenzyme, rubredoxin, and a fragment thereof. In one embodiment, the redox active domain comprises plastocyanin or a fragment thereof. In one embodiment, the redox active domain comprises rubredoxin or a fragment thereof.

In another aspect, provided herein is a nucleic acid sequence encoding a fusion protein comprising an amyloid polypeptide fused to a redox active domain.

In one embodiment, the amyloid polypeptide is selected from the group consisting of CsgA, CspA, a beta-lactoglobulin, a lysozyme, Sup35, and an amyloid-beta peptide.

In one embodiment, the redox active domain is selected from the group consisting of a metalloprotein, a redox enzyme, a binding domain, and a stimuli-responsive peptide. In one embodiment, the redox active domain is selected from the group consisting of plastocyanin, an oxygen-carrier protein, a microperoxidase, a cytochrome, a copper-binding protein, an iron-binding protein, a gold-binding domain, a metalloenzyme, rubredoxin, and a fragment thereof. In one embodiment, the redox active domain comprises plastocyanin or a fragment thereof. In one embodiment, the redox active domain comprises rubredoxin or a fragment thereof.

In one embodiment, the amyloid polypeptide comprises a series of aligned aromatic groups. In one embodiment, the aromatic group is present on a standard amino acid or a nonstandard amino acid. In one embodiment, the aromatic group is present on a standard amino acid selected from the group consisting of phenylalanine, tryptophan, tyrosine and histidine. In one embodiment, the aromatic group is present on a nonstandard amino acid selected from the group consisting of 2-thienylalanine, 3-thienylalanine, acetylphenylalanine and azidophenylalanine.

In one aspect, provided herein is a vector comprising a nucleic acid sequence described herein. In one embodiment, the nucleic acid sequence is operably-linked to an inducible promoter. In one embodiment, the nucleic acid is operably-linked to a constitutive promoter.

In another aspect, provided herein is a bacterium comprising a nucleic acid sequence, or a vector comprising a nucleic acid sequence described herein.

In yet another aspect, provided herein is a biofilm comprising a bacterium expressing a nucleic acid sequence encoding a non-naturally occurring mutant amyloid polypeptide having a series of aligned aromatic groups.

In another aspect, provided herein is a biofilm comprising a bacterium expressing a nucleic acid sequence encoding a fusion protein comprising an amyloid polypeptide fused to a redox active domain.

Embodiments of the present disclosure are directed to engineered or genetically-altered microorganisms, such as E. coli, that produce amyloid-based structures that include moieties suited to electron transport through pi-stacking induced electron delocalization, such as amino acid sides having aromatic side chains. In one aspect, the genetically-altered microorganism is engineered to produce an amyloid fiber characterized by electron transfer along the amyloid fiber. According to one aspect, E. coli is engineered to produce curli protein nanofibers characterized by electron transfer along the curli protein nanofibers. In order to generate electron transfer, amyloid fibers (e.g., curli fibers) with π-π stacking are created. According to one aspect, amino acid residues in an amyloid polypeptide (e.g., CsgA) are identified and mutated to amino acids having aromatic side chains without altering the basic amyloid structure of the curli fiber. Any amyloid protein may be used as described herein. Exemplary amyloid proteins include, but are not limited to CsgA, CspA, beta-lactoglobulin, lysozyme, Sup35, or an amyloid-beta peptide. In some embodiments, the amyloid protein is a protein capable of forming beta-helical amyloid assemblies. For example, in some embodiments, the amino acid residues identified for mutation are aligned along the five repeats of the beta-helix structure of CsgA. The conjugated side-chains of aligned aromatic residues, or their non-natural or nonstandard amino acid derivatives interact to form π-stacks and induce electron delocalization.

Useful amino acids may be standard amino acids or nonstandard amino acids, canonical amino acids or non-canonical amino acids. Exemplary nonstandard amino acids include but are not limited to a histidine or phenylalanine derivative, e.g., 2-thienylalanine, 3-thienylalanine acetylphenylalanine, azidophenylalanine, or an amino acid comprising a side chain comprising a monomer of a polymer such as poly(3-hexylthiophene-2,5-diyl) (P3HT) or polyaniline. In some embodiments, the histidine or phenylalanine derivative comprises a side chain similar to histidine or phenylalanine (respectively) but with improved electron delocalization or electron transfer properties.

According to a certain aspect, the microorganism produces protein fibers using a biosynthetic pathway with the protein fibers having aromatic amino acids along the fiber length and oriented to provide pi-pi stacking for electron transport. As such, the protein fibers are electrically conductive. According to one aspect, the protein fibers are curli fibers produced by bacteria. According to aspects of the present disclosure, self-assembling amyloid-based curli fibers, which often grow to be >10 μm in length, provide long-range electron transport between bacterial cells and with abiotic electrode surfaces. Aspects of the present disclosure may utilize materials and methods described in Barnhart, M. M. & Chapman, M. R. Curli Biogenesis and Function. *Annu. Rev. Microbiol.* 60, 131-147 (2006) hereby incorporated by reference in its entirety.

Embodiments of the present disclosure are directed to engineered or genetically altered microorganisms, such as *E. coli*, that produce amyloid-based structures that have attached thereto peptide domains including metal centers that facilitate transmission of electrons from one metal center to the next. In some embodiments, the amyloid-based structure is formed by fusion proteins comprising an amyloid polypeptide (e.g., CsgA) and a redox active domain. In some embodiments, the amyloid-based structure is a curli fiber, formed for example by CsgA fused to one or more peptide domains including metal centers. In some embodiments, the amyloid-based structure comprises a plurality of fusion proteins comprising an amyloid polypeptide and a redox active domain. In some embodiments, the redox active domain comprises a metal center. In some embodiments, the redox active domain does not comprise a metal-binding peptide. In some embodiments, the amyloid-based structure comprises a series of aligned metal centers which allow electrons to move from one metal center to another, thereby making the amyloid curli fiber electrically conductive. In some embodiments, the amyloid based fiber is a curli fiber formed by fusion proteins comprising a CsgA polypeptide and a redox active domain. In some embodiments, when the CsgA units are combined into a curli fiber, the one or more peptide domains including metal centers are aligned in a manner, given the structure of the curli fiber, to allow electrons to move from one metal center to the next, thereby making the curli fiber electrically conductive. According to one aspect, conductive peptides form a close-packed network allowing for electron hopping from one subunit to the next. Electron hopping or movement from one subunit to the next occurs between protein domains with metal coordination centers such as ferritin, cytochromes or heme-like proteins. According to one aspect, the protein domains with metal coordination centers are plastocyanin or rubredoxin.

In one aspect, provided herein are amyloid based structures formed by a plurality of mutant amyloid polypeptides having a series of aligned aromatic groups. According to one aspect, the basic unit of a curli fiber, for example CsgA, includes one or more aromatic groups, for example aromatic amino acids and when the CsgA units are combined into a curli fiber. In some embodiments, the one or more aromatic groups are aligned in a manner, given the structure of the amyloid-based structure (e.g., a curli fiber), to create pi-pi stacking for electron transport. Aromatic rings form a π-π (pi-pi) stacking network along the amyloid-based structures (e.g., curli fibers), which induces interchain electron delocalization. In such stacked aromatic systems, charges are spread (or delocalized) across p-orbitals of the rings, and across side chains. According to one aspect, an exogenous nucleic acid encoding the fiber subunit (e.g., a mutant amyloid polypeptide) bearing the one or more aromatic amino acids, e.g., a CsgA subunit for a curli fiber, is introduced into the bacteria for expression. According to one aspect, the endogenous nucleic acid encoding for the fiber subunit, e.g., the curli fiber subunit CsgA, may be removed from the bacterium. According to one aspect, the endogenous nucleic acid encoding for the fiber subunit, e.g., the curli fiber subunit CsgA, may be genetically altered or modified or mutated to comprise one or more aromatic amino acids. In this context, the amyloid polypeptide (e.g., CsgA) may be referred to as a mutant amyloid polypeptide a modified amyloid polypeptide or an altered amyloid polypeptide (e.g., mutant CsgA or modified CsgA or altered CsgA). According to one aspect, a series of aligned residues in an amyloid polypeptide (e.g., CsgA) are identified and mutated to aromatic amino acids within the helix structure of the amyloid polypeptide (e.g., the five pseudo-repeats of the CsgA helix structure). The aromatic residues interact and form π-stacks leading to electron delocalization and optical phenomena. According to one aspect, biofilms comprising the mutant amyloid polypeptide or amyloid-based structures comprising the mutant amyloid polypeptide (e.g., CsgA-based curli fibers) are included. According to one aspect, the mutant amyloid polypeptide or amyloid-based structures comprising the mutant amyloid polypeptide (e.g., mutant CsgA-based curli fibers) are isolated from bacteria. According to one aspect, the amyloid-based structures (e.g., mutant CsgA-based curli fibers) are screened for electrical conductivity using, for example, colorimetric detection of redox activity, conductive AFM (current (ORCA), electrostatic (EFM) or Kelvin-probe (KPFM)) or a current-voltage response of a biofilm comprising amyloid-based structures comprising the mutant amyloid polypeptides (e.g., mutant CsgA-based curli fibers) in an electrode array. According to one aspect, the amyloid-based structures comprising a mutant amyloid polypeptide (e.g., mutant CsgA-based curli fibers) may also include moieties providing charged, amphiphilic or hydrophobic properties. According to one aspect, the amyloid-based structures (e.g., mutant CsgA-based curli fibers) may also include natural or non-natural amino acids having moieties suitable for covalent bonding, e.g., a chemical moiety suitable for a click chemistry reaction with a non-natural amino acid.

In one aspect, provided herein is a mutant amyloid polypeptide comprising one or more aligned aromatic groups, wherein said amyloid polypeptides form amyloid-based structures having modified hydrophilicity or hydrophobicity, as compared to an amyloid-based structure formed by wild-type amyloid polypeptide. In some embodiments, the mutant amyloid polypeptide comprises several amino acid replacements, whereby aromatic amino acids are incorporated into the protein such that upon folding a side of the protein comprises aromatic amino acids. In some embodiments, one side of the protein comprises aligned aromatic amino acids and the other side of the protein is unchanged. In some embodiments, the mutant amyloid polypeptide forms an amyloid-based structure with modified fluorescent ability (e.g., increased fluorescent ability) as compared to an amyloid-based structure formed of wild-type amyloid polypeptide. In some embodiments, the mutant amyloid polypeptide forms an amyloid-based structure with modified charge (e.g., positive charge or negative charge) as compared to an amyloid-based structure formed of wild-type amyloid polypeptide. In some embodiments, the mutant amyloid polypeptide forms an amyloid-based structure with modified fluorescent ability (e.g., increased fluorescent ability) as compared to an amyloid-based structure formed of wild-type amyloid polypeptide. In some embodiments, the mutant amyloid polypeptide forms an amyloid-based structure with modified electric conductivity ability (e.g., increased conductivity ability) as compared to an amyloid-based structure formed of wild-type amyloid polypeptide.

According to one aspect, mutant CsgA modified to include one or more aromatic groups, wherein the mutant CsgA modifies the hydrophilicity/hydrophobicity of a curli fiber comprising the mutant CsgA, are provided. According to one aspect, mutant CsgA is provided where a full side of the protein is mutated to aromatic residues (for example stacks 4 and 5 together, or stacks 1, 2 and 3 together) while the other side of the protein is unchanged. This produces amphiphilic fibers compared to wild type curli fibers.

According to one aspect, mutant CsgA modified to include one or more aromatic groups, wherein the mutant CsgA modifies the fluorescent ability of a curli fiber comprising the mutant CsgA, are provided. According to one aspect, mutant CsgA is provided which produce curli fibers having increased fluorescence as compared to the fluorescence of wild type curli fibers that do not comprise mutant CsgA.

According to one aspect, mutant CsgA modified to include charged groups, wherein the mutant CsgA modifies or creates a negative or positive charge in a curli fiber comprising the mutant CsgA as compared to the charge of a curli fiber that does not comprise the mutant CsgA are provided.

According to one aspect, an amyloid polypeptide (e.g., CsgA) comprising a mutation to include one or more non-standard amino acids are provided, whereby upon incorporation of the mutant amyloid polypeptide (e.g., mutant CsgA) into an amyloid based structure (e.g., a curli fiber), the nonstandard amino acids provide properties to the curli fibers that are different from the properties of amyloid-based structures formed by wild-type amyloid polypeptides (e.g., wild-type curli fibers). For example, in some embodiments, curli fibers comprising CsgA mutated to contain azidophenylalanine and acetylphenylalanine may be used to perform bio-orthogonal covalent chemistry (e.g., click chemistry reactions using azidophenylalanine, and reactions between the ketone group of acetylphenylalanine and alkoxyamine derivatives).

According to one aspect, a bacterium as described herein can proliferate and express the nucleic acid encoding the mutant amyloid polypeptide (e.g., mutant CsgA) to a produce amyloid-based structure (e.g., curli fibers) having aromatic amino acids along the length of the amyloid-based structure (e.g., curli fiber) and oriented in a manner to provide pi-pi stacking for electron transport along the length of the fiber. In one aspect, the amyloid-based structures comprising a mutant amyloid polypeptide or a fusion protein described herein form an electrically conductive biofilm. According to one aspect, the mutant amyloid polypeptide or fusion protein described herein may be attached, connected or fused to an electrical conductivity enhancing protein to further enhance the electrical conductivity of the amyloid-based structure beyond the pi-pi stacking of the aromatic groups along the length of the amyloid-based structure. According to one aspect, the curli fiber may form an electrically conductive biofilm. According to one aspect, the mutant CsgA may be attached, connected or fused to an electrical conductivity enhancing protein to further enhance the electrical conductivity of the curli fiber beyond the pi-pi stacking of the aromatic groups along the length of the curli fiber.

Embodiments of the present disclosure are directed to methods of genetically modifying a bacterium to include a nucleic acid that encodes a mutant amyloid polypeptide (e.g., a mutant CsgA protein) including one or more aromatic amino acids not present in wild type CsgA for expression within the bacterium. In some embodiments, provided herein are methods of genetically modifying a bacterium to include a nucleic acid encoding a fusion protein comprising an amyloid polypeptide and a redox active domain. Such genetic modification may be accomplished by mutation of an endogenous nucleic acid sequence encoding the wild-type amyloid polypeptide (e.g., wild-type CsgA) or introduction of an exogenous nucleic acid encoding a mutant amyloid polypeptide or a fusion protein described herein (e.g., a mutant CsgA) using methods known to those of skill in the art.

Aspects of the present disclosure may utilize materials and methods described in: Cherny, I. & Gazit, E. Amyloids: Not Only Pathological Agents but Also Ordered Nanomaterials. *Angew Chem Int Edit* 47, 4062-4069 (2008); Culver, J. N. et al. Plant virus directed fabrication of nanoscale materials and devices. Virology 479-480, 200-212 (2015); Fischlechner, M. & Donath, E. Viruses as Building Blocks for Materials and Devices. *Angew Chem Int Edit* 46, 3184-3193 (2007); Ulijn, R. V. & Woolfson, D. N. Peptide and protein based materials in 2010: from design and structure to function and application. *Chem. Soc. Rev.* 39, 3349 (2010); Rodríguez-Ropero, F., Zanuy, D., Assfeld, X. & Alemán, C. Modeling an Electronic Conductor Based on Natural Peptide Sequences. *Biomacromolecules* 10, 2338-2343 (2009); Hamley, I. W. et al. Self-Assembly of a Designed Amyloid Peptide Containing the Functional Thienylalanine Unit. *J. Phys. Chem. B* 114, 10674-10683 (2010), each of which are hereby incorporated by reference in their entirety, as synthetic biomolecular systems, such as amyloids, viruses, and those derived from other self-assembling protein scaffolds, offer embodiments of nanoscale spacing of chemical functional groups, including those particularly suited for electron transport and not represented in the naturally occurring amino acids.

According to the present disclosure, such systems can be modified with one or more molecules in order to enhance their electron transport properties. Aspects of the present disclosure may utilize Vargas, M. et al. Aromatic Amino Acids Required for Pili Conductivity and Long-Range Extracellular Electron Transport in *Geobacter sulfurreducens*. *mBio* 4, e00105-13-e00105-13 (2013); Malvankar, N. S., Tuominen, M. T. & Lovley, D. R. Comment on 'On electrical conductivity of microbial nanowires and biofilms' by S. M. Strycharz-Glaven, R. M. Snider, A. Guiseppi-Elie and L. M. Tender, Energy Environ. Sci., 2011, 4, 4366. *Energy Environ. Sci.* 5, 6247 (2012); Strycharz-Glaven, S. M. & Tender, L. M. Reply to the 'Comment on "On electrical conductivity of microbial nanowires and biofilms"' by N. S. Malvankar, M. T. Tuominen and D. R. Lovley, Energy Environ. Sci., 2012, 5, DOI: 10.1039/c2ee02613a. *Energy Environ. Sci.* 5, 6250 (2012); Strycharz-Glaven, S. M., Snider, R. M., Guiseppi-Elie, A. & Tender, L. M. On the electrical conductivity of microbial nanowires and biofilms. *Energy Environ. Sci.* 4, 4366 (2011) describing embodiments of "metallic-like" conductivity that arises from pi-stacked aromatic groups. According to one exemplary aspect, the conductive fibers and biofilms disclosed herein may be combined with other bacteria to produce hybrid biofilms with enhanced long-range conductivity so as to provide efficient bioelectrosynthetic systems and microbial fuel cells. Other applications of conductive curli fibers include biosensors, fabrication of conductive electrodes and materials (e.g., free-standing electrodes, solution-processable electrodes, biocompatible electrodes, etc.), and fabrication of composites with other nanomaterials.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIGS. 1A-1B depict a biosynthetic conductive nanowire concept overview. FIG. 1A is a comparison between the electrically conductive systems produced by natural organisms, and chemical synthesis or recombinant expression. FIG. 1B schematically depicts variants of the major curli subunit (CsgA) containing periodically spaced aromatic amino acid residues (indicated with "*"). During biofilm formation, these variants will be secreted and assembled into functional curli fibers containing the aromatic side chains aligned to yield a network of conductive nanowires.

FIG. 2A depicts ΔcsgA strain of *E. coli* transformed with a plasmid encoding for CsgA appended to a heterologous peptide domain. These domains are displayed throughout the biofilm and imbue it with non-natural functions. FIG. 2B depicts images of curli fibers displaying a silver binding peptide that can template the growth of silver nanoparticles (middle, right), whereas the wild-type curli network cannot (left). FIG. 2C depicts images of curli fibers displaying a steel binding peptide (right) that enable biofilm adhesion to a steel coupon, whereas cells producing wild-type curli (middle) or no curli (left) do not adhere. FIG. 2D schematically depicts curli fibers displaying a conjugation domain that can site selectively immobilize proteins or arbitrary size, including enzymes.

FIG. 3A is a schematic of a CsgA protein sequence. Alignment shows pseudo-repeat sequences with sites of proposed mutations (Series 1, 2). All five residues will be mutated simultaneously to one of the following aromatic amino acids: tyrosine, tryptophan, histidine, or 3-thienylalanine (through non-standard amino acid incorporation). FIG. 3B depicts a homology model of CsgA protein depicting a histidine mutant from Series 2. Adjacent CsgA monomers in an assembled curli fiber are depicted. Histidine residues are also depicted. The average distance between neighboring histidine residues is 5.1 Å.

FIGS. 4A and 4B depict CsgA with a His-tag in the pET1d plasmid and the corresponding nucleic acid and amino acid sequences. FIG. 4A is a schematic representation of CsgA with his-tag in the pET21d plasmid. FIG. 4B is a schematic representation and corresponding nucleic acid and amino acid sequences of wild-type CsgA with a C-terminal His-tag. The depicted open reading frame also includes a SEC signal peptide, an N22 peptide, and a linker serine-glycine linker sequence (SEQ ID NOs: 1 and 2).

FIGS. 6A-6B shows Congo Red binding to CsgA mutants and fusions.

FIG. 7 shows electron microscopy of curli fibers produced by mutant and control bacteria.

FIG. 13 shows the residual impurities after purification of mutant and control curli fibers.

FIGS. 14A and 14B depicts the purification of curli nanofiber thin films, and measurement of thin film electrical properties.

FIG. 15A depicts wild-type curli fibers dropcast on plasma-treated silicon wafers at decreasing concentrations (from left to right) of 1.5, 0.75, 0.15 and 0.015 mg/mL, from 1:1 HFIP:TFA mixtures. Prior to dropcasting, fibers were sonicated for 1 hr in HFIP and TFA. Samples were imaged using scanning electron microscopy (SEM). FIG. 15B depicts high magnification scanning electron microscopy (SEM) images showing single fibers for diluted samples.

FIGS. 16A and 16B depict (SEM) images of dropcast films formed using dilute solutions of curli fibers comprising CsgA fused to either ferritin domain, plastocyanin or rubredoxin (FIG. 16A) or curli fibers comprising mutant CsgA (FIG. 16B) can be dissolved/disassembled in HFIP/TFA and reassembled on a substrate. SEM images of dispersed mutant and fusion curli fibers, after dissolution/disassembly in 1:1 HFIP:TFA, and reassembly by dropcasting and solvent evaporation on a silicon substrate are shown.

FIG. 19A depicts the top surface morphology of the film. FIG. 19B depicts the scratch in the film at the film-electrode interface showing the fibrous cross-section and the good contact between the fibers and the gold electrode.

FIGS. 20A and 20B depict SEM images of dropcast films formed using curli fibers comprising CsgA fused to plastocyanin on commercial Micrux interdigitated electrodes. Samples were not coated with Pt/Pd prior to imaging. FIG. 20A. depicts CsgA-plastocyanin fibers dropcast at a dilute 0.1 mg/mL concentration on interdigitated electrodes. SEM images show fibrous surface morphology. FIG. 20B depicts CsgA-plastocyanin fibers dropcast at 10 mg/mL on interdigitated electrodes. Full coverage of the electrode is observed. Fibers form a thick film.

FIG. 21A depicts the current-voltage curves for curli fibers comprising CsgA fused to plastocyanin ("plastocyanin"), hexafluoro-2-propanol: trifluoroacetic acid solvent control ("HFIP:TFA"); curli fibers comprising wild-type CsgA ("WT"); milk control ("Milk"); or bovine serum albumin control ("BSA"); or non-coated electrodes ("Blank"). FIG. 21B depicts current-voltage curves for control proteins: curli fibers comprising wild-type CsgA ("WT"); milk control ("Milk"); or bovine serum albumin control ("BSA").

FIG. 22A depicts a current-voltage curve of a scan from −2 V to +2 V. FIG. 22B. depicts a current-voltage curve of a scan from −20 V to +20 V. FIG. 22C depicts a current-voltage curve of a scan from 0 to 20 V, and back from 20 V to 0 V showing little hysteresis between the forward and reverse scans.

DETAILED DESCRIPTION

Figure 2A:
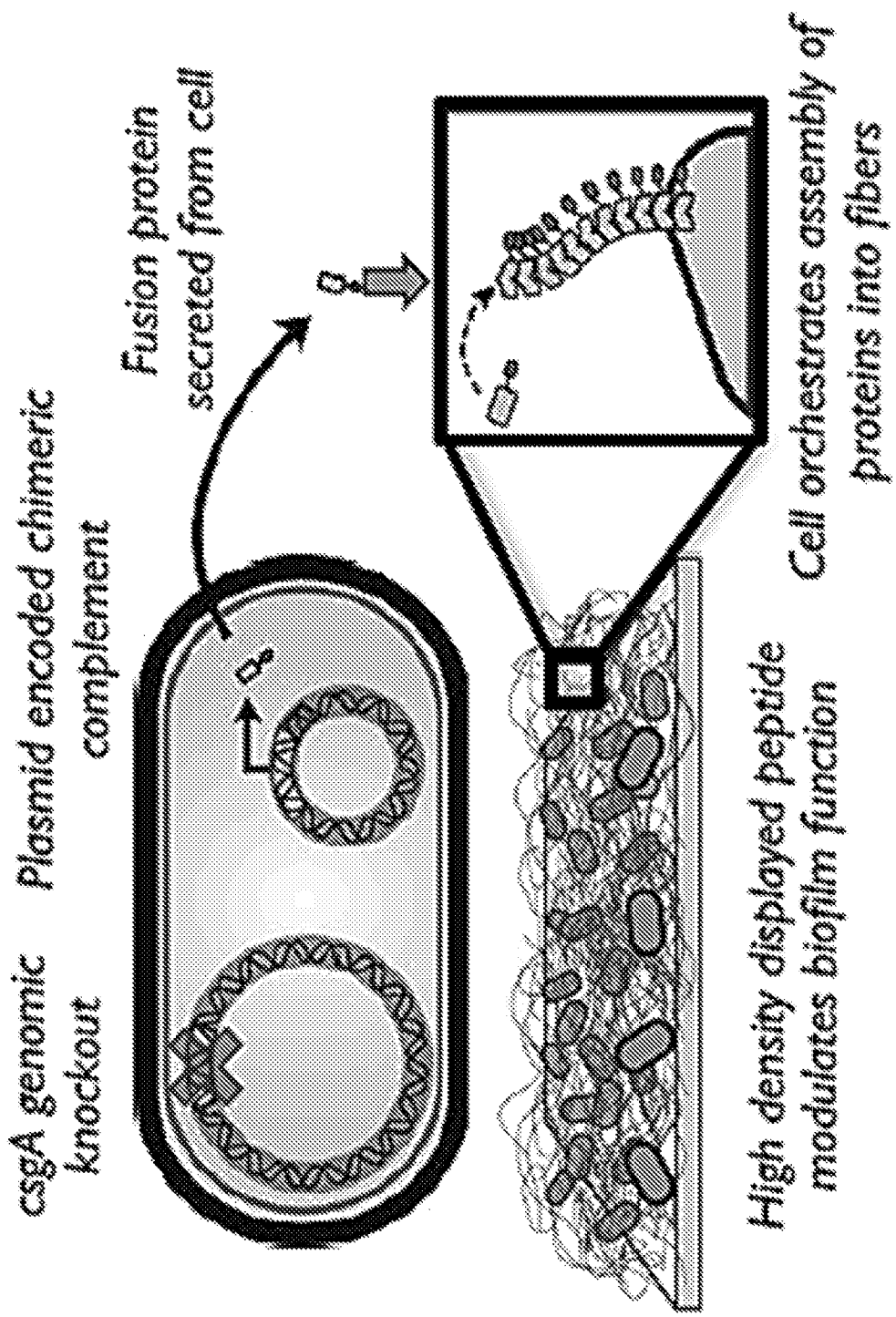
FIGS. 2A-2D depict the Biofilm Integrated Nanofiber Display (BIND) as a method for analyzing curli fibers including mutant CsgA having one or more aromatic amino acids or aromatic group side claims.

Aspects of the present disclosure are directed to the use of a bacterium capable of producing an amyloid-based structure (e.g., a bacterium with a curli fiber-producing capability) to produce amyloid-based structures (e.g., curli fibers) having mutant amyloid units (e.g., a fusion protein or mutant amyloid polypeptide described herein including mutant CsgA units) which comprise one or more aromatic groups or aromatic side chains or aromatic amino acids. The aromatic groups are aligned along the length of the amyloid-based structure (e.g., curli fiber) to allow for electrical conductance or for electron transporting via pi-pi stacking.

According to one aspect, methods of the present invention use the curli fiber production systems of a bacterium, such as E. coli. Curli fibers are the primary proteinaceous structural component of E. coli biofilms. They are highly robust functional amyloid nanofibers with a diameter of ~4-7 nm that exist as extended tangled networks encapsulating the cells. Curli fibers are formed from the extracellular self-assembly of CsgA, a small secreted 13-kDa protein. Chapman, M. R. et al. Role of Escherichia coli curli operons in directing amyloid fiber formation. Science 295, 851-855 (2002). A homologous outer-membrane protein, CsgB, nucleates CsgA assembly and also anchors the nanofibers to the bacterial surface. Detached curli fibers can also exist as non-cell associated structural components of the ECM. The curli genes exist as two divergently transcribed operons (csgBAC and csgDEFG), whose seven products mediate the structure (CsgA), nucleation (CsgB), processing (CsgE, F), secretion (CsgC, G), and direct transcriptional regulation (CsgD) of curli nanofibers. This curli secretion system is considered a distinct secretion system of its own in gram-negative bacterium and is named the Type-VIII secretion system (T8SS). See Desvaux et al., Trends Microbiol. 17, 139-45 (2009) hereby incorporated by reference in its entirety. According to one aspect, other useful bacteria with suitable secretions systems known to those of skill in the art may be used to produce the electrically conductive curli fibers of the present disclosure.

As used herein, "CsgA" refers to the major structural subunit of curli. The sequences of CsgA and its homologs are known in a number of species, e.g. the sequence of E. coli CsgA is known (encoded by csgA (NCBI Gene ID NO: 949055); SEQ ID NO: 44 (polypeptide)).

CsgA polypeptide (NCBI Ref Seq: NP_415560)
(SEQ ID NO: 44)
mkllkvaaiaaivfsgsalagvvpqygggnhggggnnsgpnselniyqy gggnsalalqtdarnsdltitqhgggngadvgqgsddssidltqrgfgns atldqwngknsemtvkqfgggngaavdqtasnssvnvtqvgfgnnatahq y In some embodiments, "CsgA" refers to E. coli CsgA. In some embodiments, "CsgA" refers to a polypeptide having at least 80% homology to SEQ ID NO: 44 (e.g., 80% or greater homology, 90% or greater homology, or 95% or greater homology), e.g. naturally occurring mutations or variants of CsgA, homologs of CsgA, or engineered mutations or variants of CsgA. In some embodiments, CsgA refers to a polypeptide comprising an amino acid sequence having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 44.

According to one aspect, self-assembling protein domains referred to herein as amyloid polypeptides, such as CsgA, are used to generate amyloid-based structures (e.g., curli fibers) including a plurality of aromatic groups arranged in pi-pi stacking to promote electrical conductivity of the amyloid-based structure (e.g., curli fiber) or electron transport along the amyloid-based structure (e.g., curli fiber). π-stacks can occur when conjugated molecules are a few angstroms apart (e.g., between 4 to 7 angstroms apart). For example, the spacing between the beta sheets of CsgA is in the range of 4.6 angstroms, which allows for proper spacing between the aromatic side chains to form a π-stack (see, e.g., Duelholm et al. (2011) Biochemistry 50(39): 8281-90. Various types of π-stack geometric configurations are formed using the mutant amyloid polypeptides described herein (e.g., mutant CsgA polypeptides) described herein. In some embodiments, mutation of an amyloid polypeptide (e.g., CsgA) with at least one amino acid having an aromatic residue results in sandwich-type π-stacks (also known as parallel rings). In some embodiments, mutation of an amyloid polypeptide (e.g., CsgA) with at least one amino acid having an aromatic residue results in t-shaped π-stacks (also known as perpendicular rings). In some embodiments, mutation of an amyloid polypeptide (e.g., CsgA) with at least one amino acid having an aromatic residue results in parallel-displaced π-stacks (also known as offset rings). π-stacks can be formed using any combination of amino acid residues having an aromatic side chain. In some embodiments, the π-stack is formed using amino acid residues of the same type. In some embodiments, the π-stack is formed using amino acid residues of different types (e.g., 2, 3, 4, 5, 6, 7, 8, 9 types of amino acid residues (e.g., natural or non-natural amino acid residues)). In some embodiments, the amyloid-based structures (e.g., curli fibers) can be deposited on pre-fabricated substrates (e.g., interdigitated electrodes) to facilitate electrical conductivity measurements. In some embodiments, the amyloid-based structures (e.g., curli fibers) are dissolved and disassembled in a solvent and dropcast onto a pre-fabricated substrate. In some embodiments, electrodes can be drawn directly onto filter membranes onto which the amyloid-based structures (e.g., curli fibers) have been directly purified, as described herein.

According to one aspect, bacteria are modified to include a nucleic acid encoding a mutant amyloid polypeptide (e.g., a mutant CsgA) having one or more aromatic groups or aromatic side chains or aromatic amino acids. The nucleic acid encoding a mutant amyloid polypeptide (e.g., a mutant CsgA) may be exogenous and introduced into the bacterium using methods known to those of skill in the art. The nucleic acid encoding a mutant amyloid polypeptide (e.g., a mutant CsgA) may result from mutation of the endogenous nucleic acid encoding an amyloid polypeptide (e.g., CsgA) using methods known to those of skill in the art. According to one aspect, the modified bacteria secrete the mutant amyloid polypeptide (e.g., mutant CsgA) which results in the production of an amyloid-based structure (e.g. a curli fiber), and optionally the production of a biofilm comprising the mutant amyloid polypeptide (e.g., mutant CsgA) being the subunit of the curli fiber. According to one aspect, the electrically conductive amyloid-based structures (e.g., curli fibers) are produced by engineered or non-naturally occurring bacteria. According to one aspect, methods are provided for engineering a bacteria to produce the electrically conductive extracellular amyloid fibers. After secretion, the mutant amyloid polypeptide (e.g., mutant CsgA) is nucleated to form an amyloid at the cell surface, and then continues to polymerize into long fibers that eventually encapsulate the cells and provide the biofilm with structural support, with the amyloid-based structure (e.g., curli fiber) and the resulting biofilm being electrically conductive.

Aspects of the present disclosure are directed to a method of producing a genetically-modified bacterium including genetically altering a bacterium to include a nucleic acid sequence encoding a mutant amyloid polypeptide (e.g., a CsgA protein) having a series of aligned aromatic groups, wherein the nucleic acid sequence is under the control of a promoter to express the mutant amyloid polypeptide (e.g., CsgA protein). According to one aspect, the bacterium is *E. coli*. In one embodiment, the bacterium is non-pathogenic. In one embodiment, the bacterium is pathogenic. In one embodiment, the bacterium is an attenuated bacterium.

According to one aspect, the aromatic group is present on a standard amino acid or a nonstandard amino acid. According to one aspect, the aromatic group is present on a standard amino acid selected from the group consisting of phenylalanine, tryptophan, tyrosine and histidine. According to one aspect, the aromatic group is present on a nonstandard amino acid selected from the group consisting of 2-thienylalanine, 3-thienylalanine, acetylphenylalanine or azidophenylalanine. According to one aspect, the nucleic acid sequence further encodes a redox active domain (e.g., one or more of a metalloprotein, redox enzyme, binding domain or stimuli-responsive peptide) fused to the mutant amyloid polypeptide (e.g., a mutant CsgA protein). According to one aspect, the nucleic acid sequence further encodes one or more of plastocyanin, an oxygen-carrier protein (e.g., hemoglobin, myoglobin, hemerythrin, and hemocyanin), a microperoxidase, a cytochrome, a copper-binding protein (e.g., azurin), an iron-binding protein (e.g., ferritin, lactoferrin, and transferrin), a metal-binding domain (e.g., a gold-binding domain), a metalloenzyme, or rubredoxin, or fragments thereof, fused to the mutant amyloid polypeptide (e.g., a CsgA protein).

In other aspects, provided herein are methods of producing a genetically-modified bacterium whereby the bacterium is genetically altered to include a nucleic acid sequence encoding fusion protein, wherein the fusion protein comprises a redox active domain (e.g., one or more of a metalloprotein, redox enzyme, binding domain or stimuli-responsive peptide) fused to an amyloid polypeptide (e.g., a wild type or mutant CsgA protein (e.g., a mutant CsgA protein described herein)). Exemplary redox active domains are described herein.

Aspects of the present disclosure are directed to a method of making an electrically conductive biofilm comprising proliferating a genetically-altered bacterial cell comprising a nucleic acid sequence encoding a mutant amyloid polypeptide (e.g., a mutant CsgA protein) having a series of aligned aromatic groups to produce a population of genetically-altered bacterial cells expressing the nucleic acid sequence and forming a biofilm from curli fibers formed from a plurality of the mutant amyloid polypeptides (e.g., mutant CsgA proteins), wherein the curli fibers have a series of aligned aromatic groups forming electrically conductive pi-pi stacking along the length of the curli fibers. In one embodiment, the bacterium is *E. coli*. In one embodiment, the bacterium is non-pathogenic. In one embodiment, the bacterium is pathogenic. According to one aspect, the aromatic group is present on a standard amino acid or a nonstandard amino acid. According to one aspect, the aromatic group is present on a standard amino acid selected from the group consisting of phenylalanine, tryptophan, tyrosine and histidine. According to one aspect, the aromatic group is present on a nonstandard amino acid selected from the group consisting of 2-thienylalanine, 3-thienylalanine, acetylphenylalanine or azidophenylalanine. According to one aspect, the nucleic acid sequence further encodes a redox active domain (e.g., one or more of a metalloprotein, redox enzyme, binding domain or stimuli-responsive peptide) fused to the mutant amyloid protein (e.g., the mutant CsgA protein). According to one aspect, the nucleic acid sequence further encodes one or more of plastocyanin, an oxygen-carrier protein (e.g., hemoglobin, myoglobin, hemerythrin, and hemocyanin), a microperoxidase, a cytochrome, a copper-binding protein (e.g., azurin), an iron-binding protein (e.g., ferritin, lactoferrin, and transferrin), a metal-binding domain (e.g., a gold-binding domain), a metalloenzyme, or rubredoxin, or fragments thereof, fused to the mutant amyloid polypeptide (e.g., a mutant CsgA protein described herein).

Aspects of the present disclosure are directed to a method of making electrically conductive amyloid-based structures (e.g., curli fibers) from a genetically-modified bacterium including providing the genetically modified bacterium in culture media conditions, wherein the genetically-modified bacterium includes a nucleic acid sequence encoding a mutant amyloid polypeptide (e.g., a mutant CsgA protein) having a series of aligned aromatic groups, wherein the nucleic acid sequence is under the control of a promoter to express the mutant amyloid polypeptide (e.g., a mutant CsgA protein), expressing the nucleic acid sequence to produce the mutant amyloid polypeptide (e.g., the mutant CsgA protein), and forming an amyloid-based structure (e.g., a curli fiber) from a plurality of the mutant amyloid polypeptides, wherein the amyloid-based structures (e.g., curli fibers) have a series of aligned aromatic groups forming electrically-conductive pi-pi stacking along the length of the amyloid-based structures (e.g., curli fibers). According to one aspect, the bacterium is *E. coli*. According to one aspect, the bacterium is non-pathogenic. According to one aspect, the aromatic group is present on a standard amino acid or a nonstandard amino acid. According to one aspect, the aromatic group is present on a standard amino acid selected from the group consisting of phenylalanine, tryptophan, tyrosine and histidine. According to one aspect, the aromatic group is present on a nonstandard amino acid selected from the group consisting of 2-thienylalanine, 3-thienylalanine, acetylphenylalanine or azidophenylalanine. According to one aspect, the nucleic acid sequence further encodes a redox active domain (e.g., one or more of a metalloprotein, redox enzyme, binding domain or stimuli-responsive peptide) fused to the mutant amyloid polypeptide (e.g., mutant CsgA protein). According to one aspect, the nucleic acid further encodes one or more of plastocyanin, an oxygen-carrier protein (e.g., hemoglobin, myoglobin, hemerythrin, and hemocyanin), a microperoxidase, a cytochrome, a copper-binding protein (e.g., azurin), an iron-binding protein (e.g., ferritin, lactoferrin, and transferrin), a metal-binding domain (e.g., a gold-binding domain), a metalloenzyme, or rubredoxin, or fragments thereof, fused to the mutant CsgA protein.

Exemplary amino acid sequences of redox active domains (e.g., metalloproteins or domains thereof) are provided below:

```
Plastocyanin, PetE-Prochlorococcus marinus subsp.
marinus str. CCMP1375 (NCBI Reference Sequence:
NP_875473.1)
                                      (SEQ ID NO: 55)
MISSLRSALSACFALLLVLAFGVASAQAKTVEVKLGTDAGMLAFEPSSVT
ISTGDSVKFVNNKLAPHNAVFEGHEELSHPDLAFAPGESWQETFTEAGTY
DYYCEPHRGAGMVGKVVVN Ferritin, mitochondrial [Cricetulus griseus
(Chinese hamster)] (NCBI Reference Sequence:
XP_003507127)
                                      (SEQ ID NO: 56)
MLSGFWFFSKHIGPALMSLPRVLHRCTVPQCLASRYPLLPASPRRLLASV

ASSQGSDGTARVRHNFHPDSEAAINHQINMELYASYVYLSMAYYFSRDDV

ALYNFSKSFLRQSLEEREHAEKLMKLQNQRGGRICLQDIKKPEQDDWESG

LRAMECALLLEKSVNQSLLDLHTLASEKGDPHLCDFLETHYLNEQVKSIK

ELGDHVHNLVTMGAPAVGLAEYLFDKHTLGSESKH

Rubredoxin [Pyrococcus furiosus DSM 3638] (NCBI
Reference Sequence: WP_011012426.1)
                                      (SEQ ID NO: 57)
MAKWVCKICGYIYDEDAGDPDNGISPGTKFEELPDDWVCPICGAPKSEFE
KLED Microperoxidase-8 (MP-8)
                                      (SEQ ID NO: 58)
AQCHTVE Microperoxidase-9 (MP-9)
                                      (SEQ ID NO: 59)
AQCHTVEK Microperoxidase-11 (MP-11)
                                      (SEQ ID NO: 60)
QKCAQCHTVE
```

In some embodiments, a polypeptide described herein (e.g., a fusion protein or a mutant amyloid polypeptide described herein) comprises an redox active domain fused to the C-terminal of an amyloid polypeptide (e.g., a wild-type or mutant CsgA protein described herein). In some embodiments, a polypeptide (e.g., a fusion protein or a mutant amyloid polypeptide described herein) comprises an redox active domain fused to the N-terminal of an amyloid polypeptide (e.g., a wild-type or mutant CsgA protein described herein). In some embodiments, a polypeptide described herein comprises a linker disposed between the amyloid polypeptide and the polypeptide to which it is fused (e.g., a redox active domain). In some embodiments, a polypeptide described herein comprises a linker disposed between the amyloid polypeptide and the polypeptide to which it is fused (e.g., a redox active domain). In some embodiments, the linker is a flexible linker. In some embodiments, the flexible linker is a glycine-serine flexible linker. In some embodiments, the glycine-serine flexible linker is GSGGSGGSGGSG (SEQ ID NO: 61) In some embodiments, the linker is an inflexible linker. In some embodiments, the linker is between 5 and 100 amino acids in length. In some embodiments, the linker is 5, 10, 15, 20, 25, 30, 35, 40, 45, 50, 55, 60, 65, 70, 75, 80, 85, 90, 95, or 100 amino acids in length. In some embodiments, the linker is 12, 24, 36, 48, 60, 72, or 96 amino acid residues in length. In some embodiments, the linker is 36 amino acid residues in length. In some embodiments, the linker is a linker described herein. The linker length may be modified to affect electron transfer within an amyloid-based structure (e.g., a curli fiber).

In some embodiments, a polypeptide described herein (e.g., a fusion protein or a mutant amyloid polypeptide described herein) comprises a signal sequence to facilitate to transport of the protein to the extracellular milieu. In some embodiments, the signal peptide is disposed at the N-terminal of the polypeptide. Any signal peptide known in the art may be used to facilitate the export of the protein to the extracellular milieu. In some embodiments, the signal peptide is a Sec signal peptide. In some embodiments, the signal peptide is cleaved. In some embodiments, the signal peptide is not cleaved.

In some embodiments, a polypeptide described herein (e.g., a fusion protein or a mutant amyloid polypeptide described herein) comprises a peptide tag. In some embodiments, the linker is a glycine-serine linker. In some embodiments, the peptide tag is a His-tag. In some embodiments, the peptide tag is a myc-tag. In some embodiments, the peptide tag is a GST-tag. In some embodiments, the peptide tag is a V5 tag. The peptide tag may be disposed at the N-terminal, C-terminal or within the mutant amyloid polypeptide or fusion protein described herein. In some embodiments, the mutant amyloid polypeptide (e.g., mutant CsgA protein) and/or fusion protein (e.g., CsgA protein fused to a redox active domain) described herein further comprises a linker disposed between the peptide tag and the mutant amyloid polypeptide and/or between the fusion protein and the peptide tag. In some embodiments, the linker is a flexible linker. In some embodiments, the linker is a non-flexible linker. Any linker described herein may be disposed between the peptide tag and the polypeptides described herein.

Methods of purifying curli fibers are known in the art and may be used to purify a curli fiber comprising a mutant CsgA protein described herein. Curli fiber purification methods include, for example, affinity chromatography purification (e.g. poly-histidine-tagged-based affinity purification), purification from SDS-PAGE gels, and salt precipitation and sequential differential centrifugation (see, e.g., Chapman et al., *Science*, 295(5556):851-855 (2002); Zhou et al., Experimental Manipulation of the Microbial Functional Amyloid Called Curli. In *Bacterial Cell Surfaces: Methods and Protocols*, Delcour, H. A., Ed. Humana Press: Totowa, N.J., 2013; pp 53-75; Collinson et al., *J. Bact.* 173(15): 4773-81 (1991); Chapman et al., *Science*, 295(5556):851-5 (2002), which are incorporated herein by reference in their entirety). In addition, curli fibers may be purified using vacuum filtration, as described, for example, in Dorval Courchesne et al. *ACS Biomaterials Science & Engineering* Article ASAP, doi: 10.1021/acsbiomaterials.6b00437 (2016), the entire contents of which are incorporated herein by reference.

Aspects of the present disclosure are directed to a genetically-modified bacterium comprising a nucleic acid sequence encoding a mutant amyloid polypeptide (e.g., a mutant CsgA protein) having a series of aligned aromatic groups, wherein the nucleic acid sequence is under the control of a promoter to express the mutant amyloid polypeptide. Aspects of the present disclosure are directed to a non-naturally-occurring mutant amyloid polypeptides (e.g., a mutant CsgA protein) having a series of aligned aromatic groups. Aspects of the present disclosure are directed to a non-naturally occurring amyloid-based structure (e.g., a curli fiber) formed from a plurality of mutant amyloid polypeptides (e.g., mutant CsgA proteins) forming a series of aligned aromatic groups, wherein the amyloid-based structure (e.g., curli fiber) has a series of aligned aromatic groups forming electrically-conductive pi-pi stacking along the length of the amyloid-based structures. Aspects of the present disclosure are directed to a nucleic acid sequence encoding a non-naturally occurring mutant amyloid polypeptide (e.g., a CsgA protein) having a series of aligned aromatic groups. Aspects of the present disclosure are directed to a vector comprising a nucleic acid sequence encoding a non-naturally occurring mutant amyloid polypeptide (e.g., a mutant CsgA protein) having a series of aligned aromatic groups. Aspects of the present disclosure are directed to a bacterium including a nucleic acid sequence encoding a non-naturally occurring mutant amyloid polypeptide (e.g., a mutant CsgA protein) having a series of aligned aromatic groups. Aspects of the present disclosure are directed to a bacterium including a vector comprising a nucleic acid sequence encoding a non-naturally occurring mutant amyloid polypeptide (e.g., a mutant CsgA protein) having a series of aligned aromatic groups. Aspects of the present disclosure are directed to a bacterium expressing a nucleic acid sequence encoding a non-naturally occurring mutant amyloid polypeptide (e.g., a mutant CsgA protein) having a series of aligned aromatic groups. Aspects of the present disclosure are directed to a biofilm including a bacterium expressing a nucleic acid sequence encoding a non-naturally occurring mutant amyloid polypeptide (e.g., a mutant CsgA protein) having a series of aligned aromatic groups.

A "vector" includes a nucleic acid construct designed for delivery to a host cell or transfer between different host cells. A vector can be viral or non-viral. Many vectors useful for transferring genes into target cells are available, e.g. the vectors may be episomal, e.g., plasmids, virus derived vectors or may be integrated into the target cell genome, through homologous recombination or random integration. In some embodiments, a vector can be an expression vector. An "expression vector" can be a vector that has the ability to incorporate and express heterologous nucleic acid fragments in a cell. An expression vector may comprise additional elements, for example, the expression vector may have two replication systems, thus allowing it to be maintained in two organisms. The nucleic acid incorporated into the vector can be operatively linked to an expression control sequence when the expression control sequence controls and regulates the transcription and translation of that polynucleotide sequence.

In some embodiments, a nucleic acid encoding a mutant amyloid polypeptide (e.g., a mutant CsgA protein) alone or being connected to a redox active domain (e.g., a metalloprotein, redox enzyme, binding domain or stimuli-responsive peptide) can be present within a portion of a plasmid. In some embodiments, a nucleic acid encoding a fusion protein comprising an amyloid polypeptide fused to a redox active domain (e.g., a metalloprotein, redox enzyme, binding domain or stimuli-responsive peptide) can be present within a portion of a plasmid. Plasmid vectors can include, but are not limited to, pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif, which is hereby incorporated by reference), pQE, pIH821, pGEX, pET series (see Studier et. al., "Use of T7 RNA Polymerase to Direct Expression of Cloned Genes," Gene Expression Technology, vol. 185 (1990), which is hereby incorporated by reference in its entirety).

A "viral vector" may be a nucleic acid vector construct that includes at least one element of viral origin and has the capacity to be packaged into a viral vector particle. The viral vector can contain a transgenic gene in place of non-essential viral genes. The vector and/or particle may be utilized for the purpose of transferring any nucleic acids into cells either in vitro or in vivo. Numerous viral vectors are known in the art and can be used as carriers of a nucleic acid into a cell, e.g. lambda vector system gt11, gt WES.tB, Charon 4.

In some embodiments, the nucleic acid encoding a polypeptide described herein can be constitutively expressed. In some embodiments, the nucleic acid encoding a polypeptide described herein can be operably-linked to a constitutive promoter. In some embodiments, the nucleic acid encoding a polypeptide described herein can be operably-linked to a constitutive promoter. In some embodiments, the nucleic acid encoding a polypeptide described herein can be inducibly-expressed. In some embodiments, the nucleic acid encoding a a polypeptide described herein can be can be operably-linked to an inducible promoter. In some embodiments, the nucleic acid encoding a polypeptide described herein can be can be operably linked to an inducible promoter. In some embodiments, the nucleic acid encoding a polypeptide described herein can be can be operably linked to a native CsgA promoter.

An "inducible promoter" may be one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, and tetracycline, steroid-responsive promoters, rapamycin responsive promoters and the like. Inducible promoters for use in prokaryotic systems are well known in the art, see, e.g. the beta.-lactamase and lactose promoter systems (Chang et al., Nature, 275: 615 (1978, which is incorporated herein by reference); Goeddel et al., Nature, 281: 544 (1979), which is incorporated herein by reference), the arabinose promoter system, including the araBAD promoter (Guzman et al., J. Bacteriol., 174: 7716-7728 (1992), which is incorporated herein by reference; Guzman et al., J. Bacteriol., 177: 4121-4130 (1995), which is incorporated herein by reference; Siegele and Hu, Proc. Natl. Acad. Sci. USA, 94: 8168-8172 (1997), which is incorporated herein by reference), the rhamnose promoter (Haldimann et al., J. Bacteriol., 180: 1277-1286 (1998), which is incorporated herein by reference), the alkaline phosphatase promoter, a tryptophan (trp) promoter system (Goeddel, Nucleic Acids Res., 8: 4057 (1980), which is incorporated herein by reference), the PLtetO-1 and Plac/are-1 promoters (Lutz and Bujard, Nucleic Acids Res., 25: 1203-1210 (1997), which is incorporated herein by reference), and hybrid promoters such as the tac promoter. deBoer et al., Proc. Natl. Acad. Sci. USA, 80: 21-25 (1983), which is incorporated herein by reference.

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including $Cu^{2+}$ and $Zn^{2+}$), galactose, tetracycline, IPTG (isopropyl-β-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause the dissociation of the tet repressor from the engineered promoter and allow transcription of the sequence downstream of the engineered promoter to occur.

A bacterial cell of the methods and compositions described herein can be any of any species. Preferably, the bacterial cells are of a species and/or strain which is amenable to culture and genetic manipulation. In some embodiments, the bacterial cell can be a gram-positive bacterial cell. In some embodiments, the bacterial cell can be a gram-negative bacterial cell. In some embodiments, the parental strain of the bacterial cell of the technology described herein can be a strain optimized for protein expression. Non-limiting examples of bacterial species and strains suitable for use in the present technologies include *Escherichia coli, E. coli* BL21, *E. coli* Tuner, *E. coli* Rosetta, *E. coli* JM101, and derivatives of any of the foregoing. Bacterial strains for protein expression are commercially available, e.g. EXPRESS™ Competent *E. coli* (Cat. No. C2523; New England Biosciences; Ipswich, Mass.). In some embodiments, the cell is an *E. coli* cell.

In some embodiments, a bacterium as described herein includes a mutation and/or deletion of the wild-type amyloid polypeptide gene (e.g., a gene encoding CsgA or CspA), e.g. such that the cell does not express wild-type amyloid polypeptide protein (e.g., CsgA). In some embodiments, the nucleic acid encoding a polypeptide described herein is introduced into a cell by homologous recombination. In some embodiments, the nucleic acid encoding a mutant amyloid polypeptide (e.g., a mutant CsgA protein alone or being connected to a redox active domain (e.g., a metalloprotein, redox enzyme, binding domain or stimuli-responsive peptide) replaces the endogenous amyloid polypeptide-encoding gene in the cell.

In one aspect, provided herein herein is a biofilm comprising an engineered microbial cell comprising one or more mutant amyloid polypeptides or fusion proteins described herein (e.g., a CsgA polypeptide having one or more aromatic groups that are not present in wild type CsgA polypeptide) and/or comprising a vector or nucleic acid encoding such a polypeptide. In one aspect, provided herein herein is a biofilm comprising an amyloid-based structure (e.g., a curli fiber) comprising a mutant amyloid polypeptide or a fusion protein described herein. As used herein, a "biofilm" refers to a mass of microorganisms which can adhere to or is adhering to a surface. A biofilm comprises a matrix of extracellular polymeric substances, including, but not limited to extracellular DNA, proteins, glyopeptides, and polysaccharides. The nature of a biofilm, such as its structure and composition, can depend on the particular species of bacteria present in the biofilm. Bacteria present in a biofilm are commonly genetically or phenotypically different than corresponding bacteria not in a biofilm, such as isolated bacteria or bacteria in a colony.

In some embodiments, the technology described herein relates to a biofilm that is produced by culturing an engineered microbial cell described herein under conditions suitable for the production of a biofilm. In some embodiments, the engineered bacterial cell expresses a recombinant mutant amyloid polypeptide having a series of aligned aromatic groups. In some embodiments, the engineered bacterial cell expresses a recombinant fusion protein comprising an amyloid polypeptide and a redox active domain. In some embodiments, the engineered bacterial cell comprises an engineered CsgA polypeptide (and/or comprising a vector or nucleic acid encoding such a polypeptide) under conditions suitable for the production of a biofilm. Conditions suitable for the production of a biofilm can include, but are not limited to, conditions under which the microbial cell is capable of logarithmic growth and/or polypeptide synthesis. Conditions may vary depending upon the species and strain of microbial cell selected. Conditions for the culture of microbial cells are well known in the art. Biofilm production can also be induced and/or enhanced by methods well known in the art, e.g. contacting cells with subinhibitory concentrations of beta-lactam or aminoglycoside antibiotics, exposing cells to fluid flow, contacting cells with exogenous poly-N-acetylglucosamine (PNAG), or contacting cells with quorum sensing signal molecules. In some embodiments, conditions suitable for the production of a biofilm can also include conditions which increase the expression and secretion of CsgA, e.g., by exogenously expressing CsgD.

In some embodiments, the biofilm can comprise a cell which produced the biofilm. In some embodiments, the biofilm comprises a mutant amyloid polypeptide described herein. In some embodiments, the biofilm comprises a fusion protein comprising an amyloid polypeptide fused to a redox active domain. In some embodiments, the biofilm comprises an amyloid-based structure formed by a plurality of mutant amyloid polypeptides described herein. In some embodiments, the biofilm comprises an amyloid-based structure comprising a mutant amyloid polypeptide described herein. In some embodiments, the biofilm comprises a fusion protein comprising an amyloid polypeptide fused to a redox active domain. In some embodiments, the biofilm comprises an amyloid-based structure formed by a plurality of fusion proteins, wherein each fusion protein comprises an amyloid polypeptide fused to a redox active domain. In some embodiments, the biofilm comprises an amyloid-based structure comprising a fusion protein described herein. In some embodiments, a composition includes an engineered CsgA polypeptide which includes CsgA having one or more aromatic groups not present in the wild type CsgA, as described herein. When expressed by a cell capable of forming curli, e.g. a cell expressing CsgA, CsgB, CsgC, CsgD, CsgE, CsgF, and CsgG or some subset thereof, CsgA units will be assembled to form curli filaments, e.g. polymeric chains of CsgA. In some embodiments, filaments of the polypeptide can be present in the composition. In some embodiments, the filaments can be part of a proteinaceous network, e.g. multiple filaments which can be, e.g. interwoven, overlapping, and/or in contact with each other. In some embodiments, the proteinaceous network can comprise additional biofilm components, e.g. materials typically found in an *E. coli* biofilm. Non-limiting examples of biofilm components can include biofilm proteins (e.g. FimA, FimH, Ag43, AidA, and/or TibA) and/or non-proteinaceous biofilm components (e.g. cellulose, PGA and/or colonic acid). In some embodiments, the composition can further comprise an engineered microbial cell comprising an engineered CsgA polypeptide and/or comprising a vector or nucleic acid encoding such a polypeptide, as described herein.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

An "amyloid polypeptide" refers to an polypeptide capable of aggregating to form a structure having fibrillar morphology. In some embodiments, the amyloid polypeptides form an amyloid-based structure which typically consists of β-strands which are perpendicular to the fiber axis and β sheets which stack parallel to the fiber axis. In some embodiments, the amyloid polypeptide is selected from the group consisting of CsgA, CspA, a beta-lactoglobulin, a lysozyme, Sup35, and an amyloid-beta peptide, or a functional fragment thereof.

An "amyloid-based structure" or "amyloid-based fiber" as used herein refers to an polymeric aggregate of amyloid polypeptides. In some embodiments, the amyloid-based structure forms a structure of fibrillary morphology. In some embodiments, the amyloid-based structure is a curli fiber. In some embodiments, the amyloid-based structure is formed by a heterogeneous population of amyloid polypeptides. In some embodiments, the amyloid-based structure is formed by a homogenous population of amyloid polypeptides. An amyloid-based structure may be formed by any population of amyloid polypeptides, including but not limited to, CsgA, CspA, a beta-lactoglobulin, a lysozyme, Sup35, and an amyloid-beta peptide.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); and Current Protocols in Protein Science (CPPS) (John E. Coligan, et al., ed., John Wiley and Sons, Inc.), which are all incorporated by reference herein in their entireties.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The following examples are set forth as being representative of the present disclosure. These examples are not to be construed as limiting the scope of the present disclosure as these and other equivalent embodiments will be apparent in view of the present disclosure, figures and accompanying claims.

Example I

Biofilm Integrated Nanofiber Display (BIND)

Figure 2B:
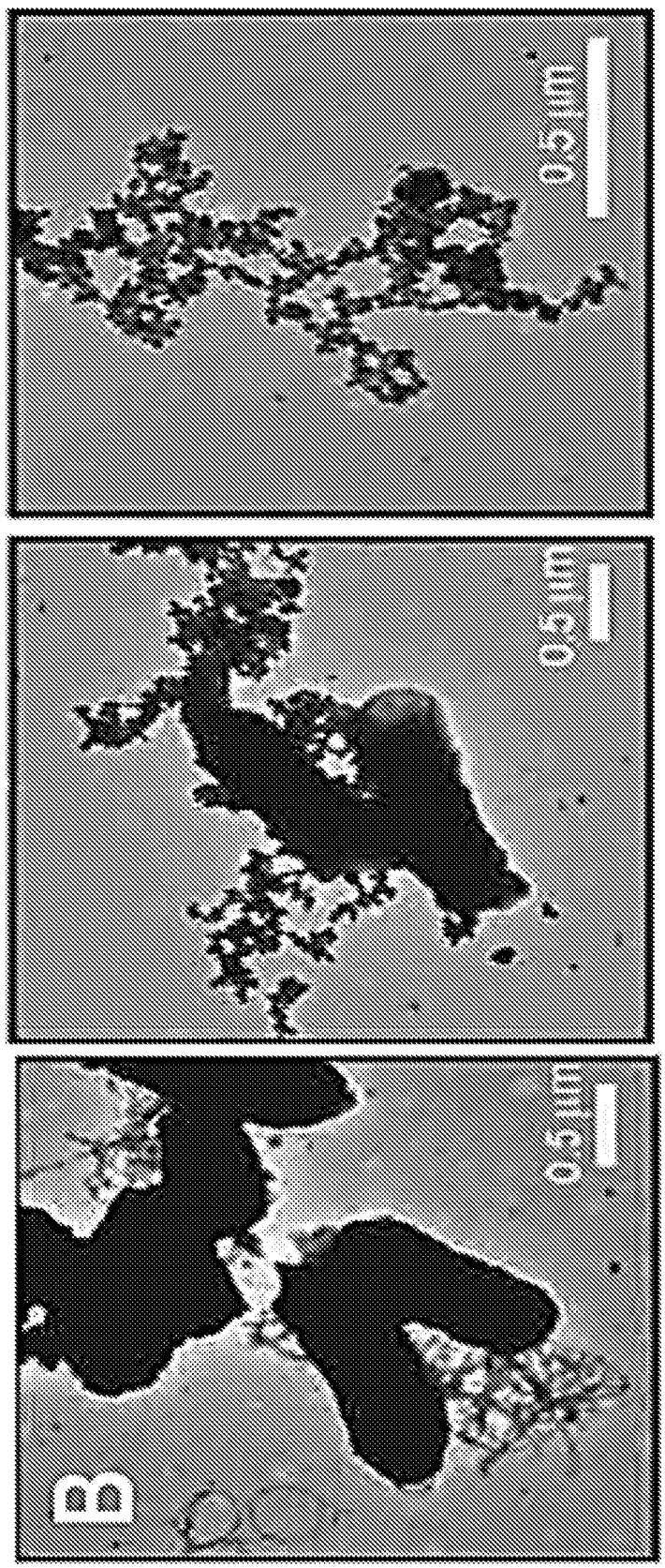
Figure 2C:
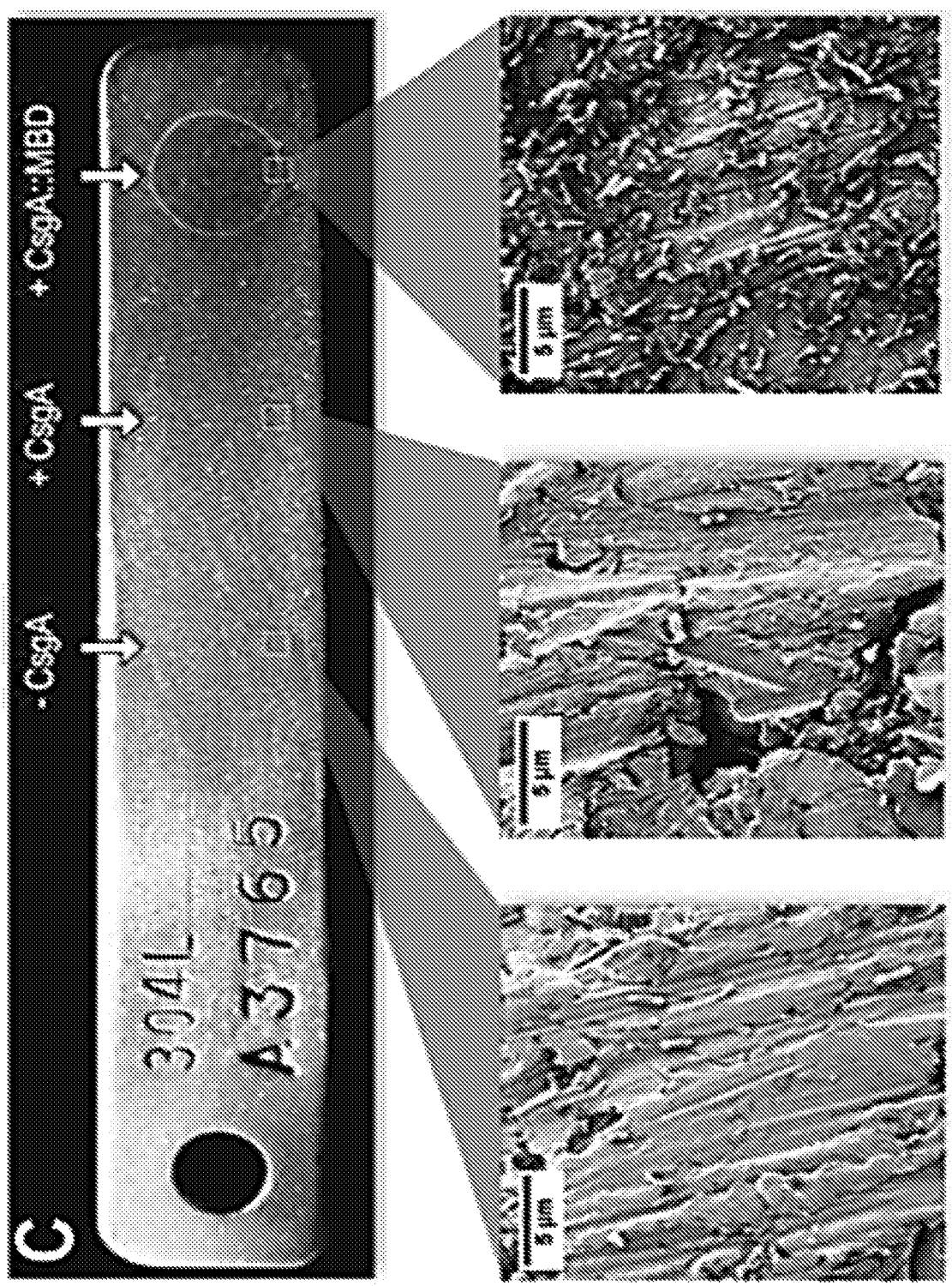
Figure 2D:
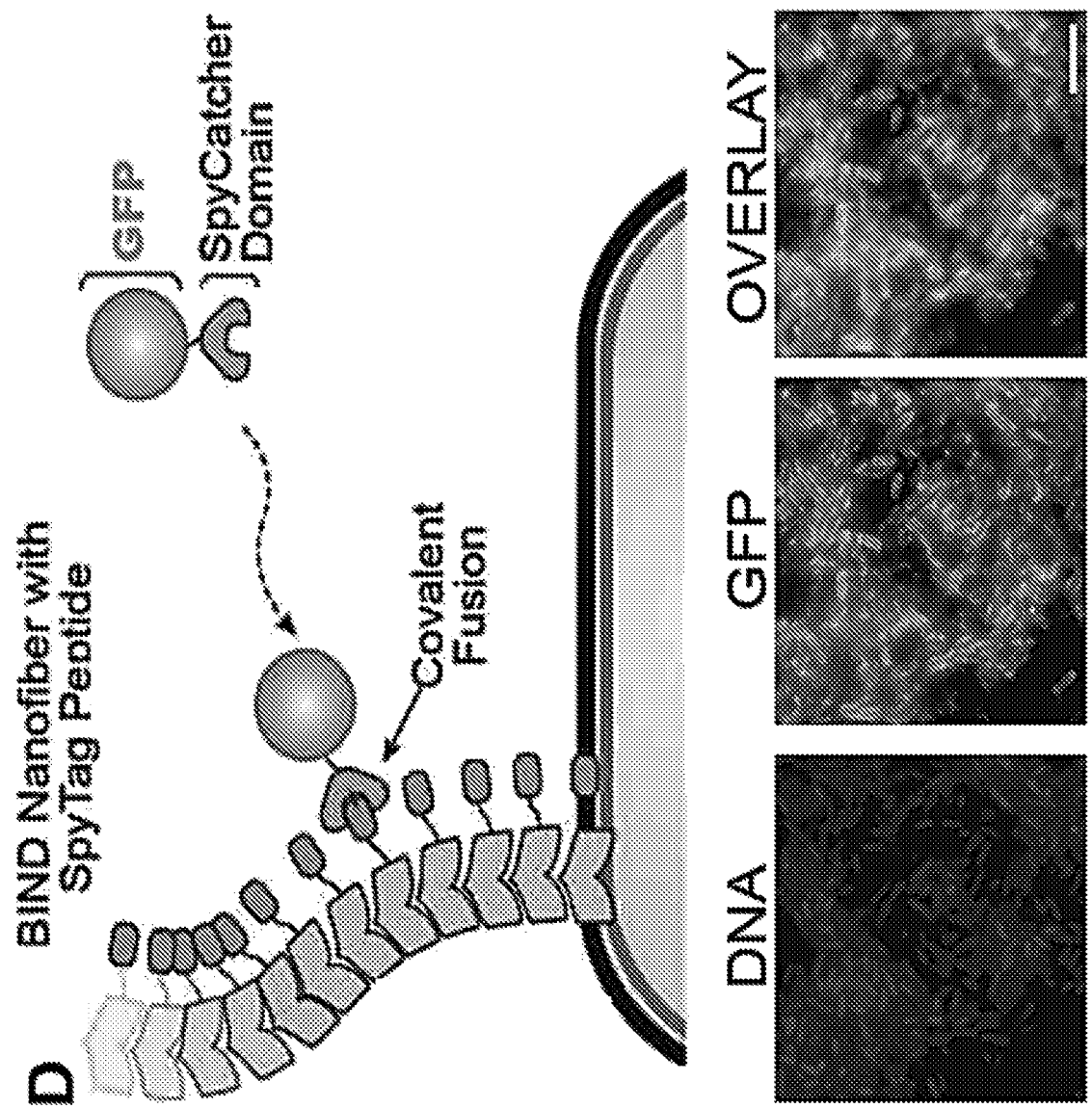

A method has been developed to repurpose the amyloid curli fibers of *E. coli* as a customizable nanomaterial, such as an electrically conductive fiber material or biofilm. This method, called Biofilm Integrated Nanofiber Display (BIND) uses straightforward genetic manipulation to append functional heterologous sequences to the CsgA protein, or a mutant as described herein, such as a redox active domain (e.g., a metalloprotein, redox enzyme, binding domain or stimuli-responsive peptide) fused to the mutant CsgA protein (FIG. 2A). These heterologous domains are chosen such that they convey non-natural or augmented functions to the biofilm as a whole. The result is a programmable and completely biosynthetic system for creating living materials with a wide range of defined functions, including electrical conductivity. Examples of functions include enhanced adhesion to abiotic surfaces, the ability to template the growth of inorganic nanoparticles, and the ability to site-specifically immobilize enzymes to yield a catalytic surface (FIGS. 2B-2D). See Botyanszki, Z., Tay, P. K. R., Nguyen, P. Q., Nussbaumer, M. G. & Joshi, N. S. Engineered catalytic biofilms: Site-specific enzyme immobilization onto *E. coli* curli nanofibers. *Biotechnol. Bioeng.* 112 (10): 2016-24 (2015); Nguyen, P. Q., Botyanszki, Z., Tay, P. K. R. & Joshi, N. S. (2014) Programmable biofilm-based materials from engineered curli nanofibers. *Nature Communications* 5:4945. Others functions include enhanced conduction of a curli-based biofilm programmed to specifically bind to gold nanoparticles. Zhong, C. et al. Strong underwater adhesives made by self-assembling multi-protein nanofibers. *Nature Nanotech* 1-9 (2014); Van Gerven, N. et al. Secretion and functional display of fusion proteins through the curli biogenesis pathway. *Molecular Microbiology* 91, 1022-1035 (2014); Chen, A. Y. et al. Synthesis and patterning of tunable multiscale materials with engineered cells. *Nature Materials* 13: 515-23 (2014).

Example II

Figure 3A:
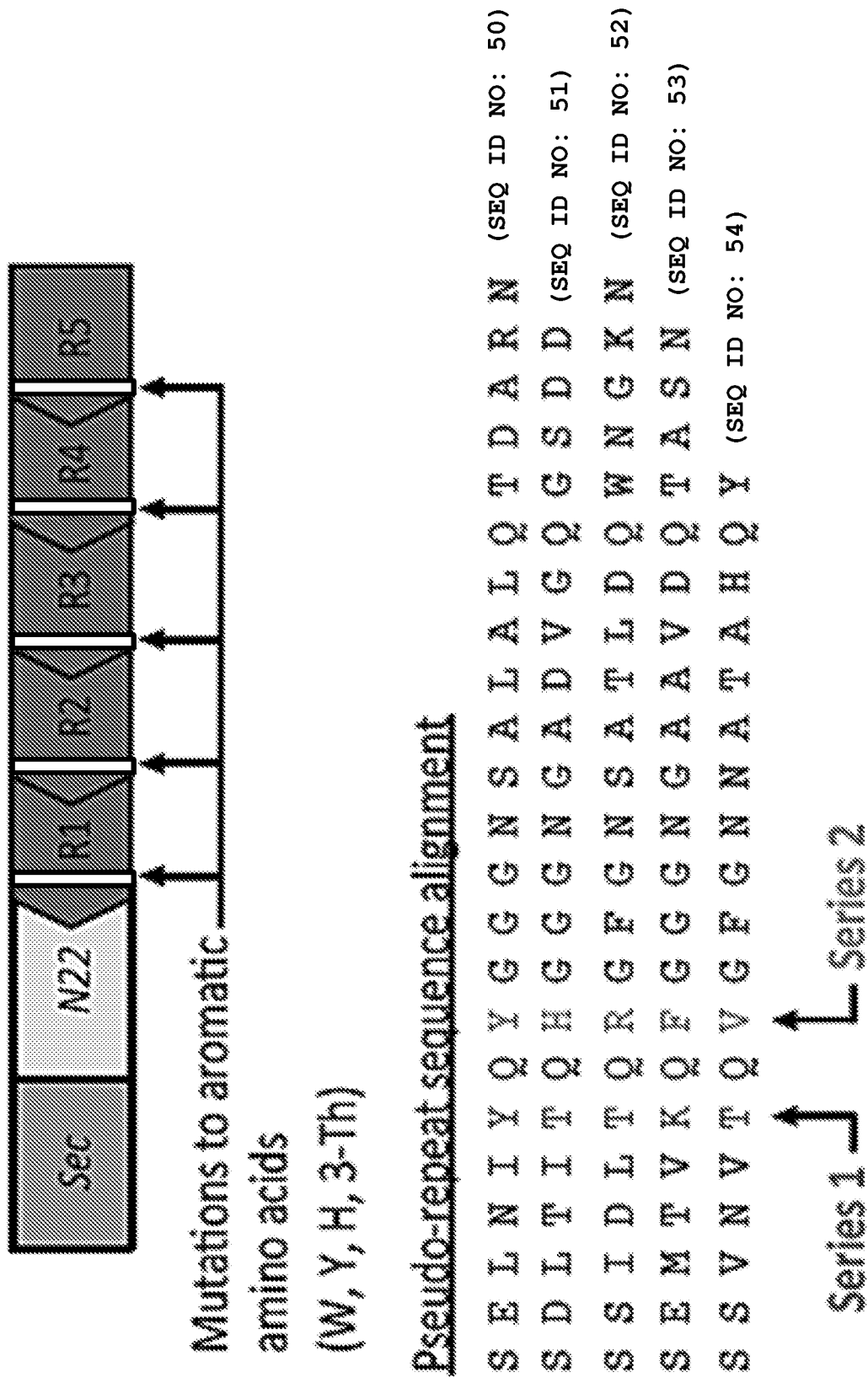
FIGS. 3A-3B schematically depict a proposed plan for CsgA engineering.

Production of Biosynthetic Amyloid Networks Containing Regularly Spaced Standard and Non-Standard Aromatic Amino Acids According to one aspect of the current disclosure, methods are included to create mutants of the CsgA protein that contain multiple periodic mutations. The CsgA sequence already consists mainly of 5 pseudo-repeats of a consensus sequence based on a Ser-$X_5$-Gln-$X_4$-Asn-$X_5$-Gln motif (SEQ ID NO: 90; FIG. 3A). The CsgA structure is quite malleable in terms of preserving its ability to assemble into amyloid fibers and can even participate in cross-seeding with a number of other amyloidogenic proteins. In one embodiment, the conserved residues in the above motif represent "gate-keeper" residues that are responsible for maintaining key intramolecular interactions, while several of the other residues can be altered without abolishing assembly function. Furthermore, some (but not all) permutations that shuffle the order the repeats R1-R5 preserve assembly as well. According to one aspect, a mutant CsgA protein is provided which includes aromatic groups on the outer face of the (β-helix.

Figure 3B:
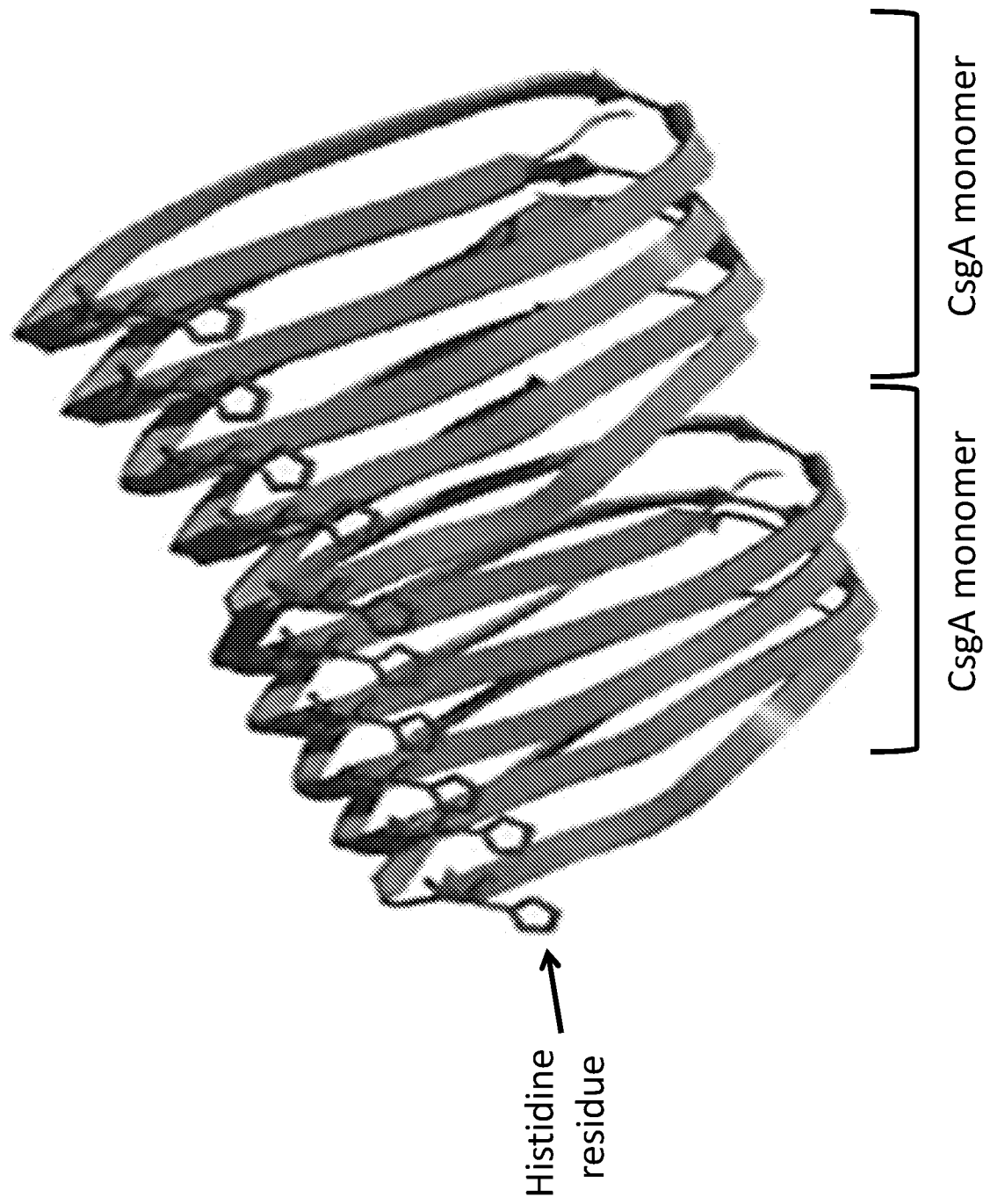
Figure 4A:
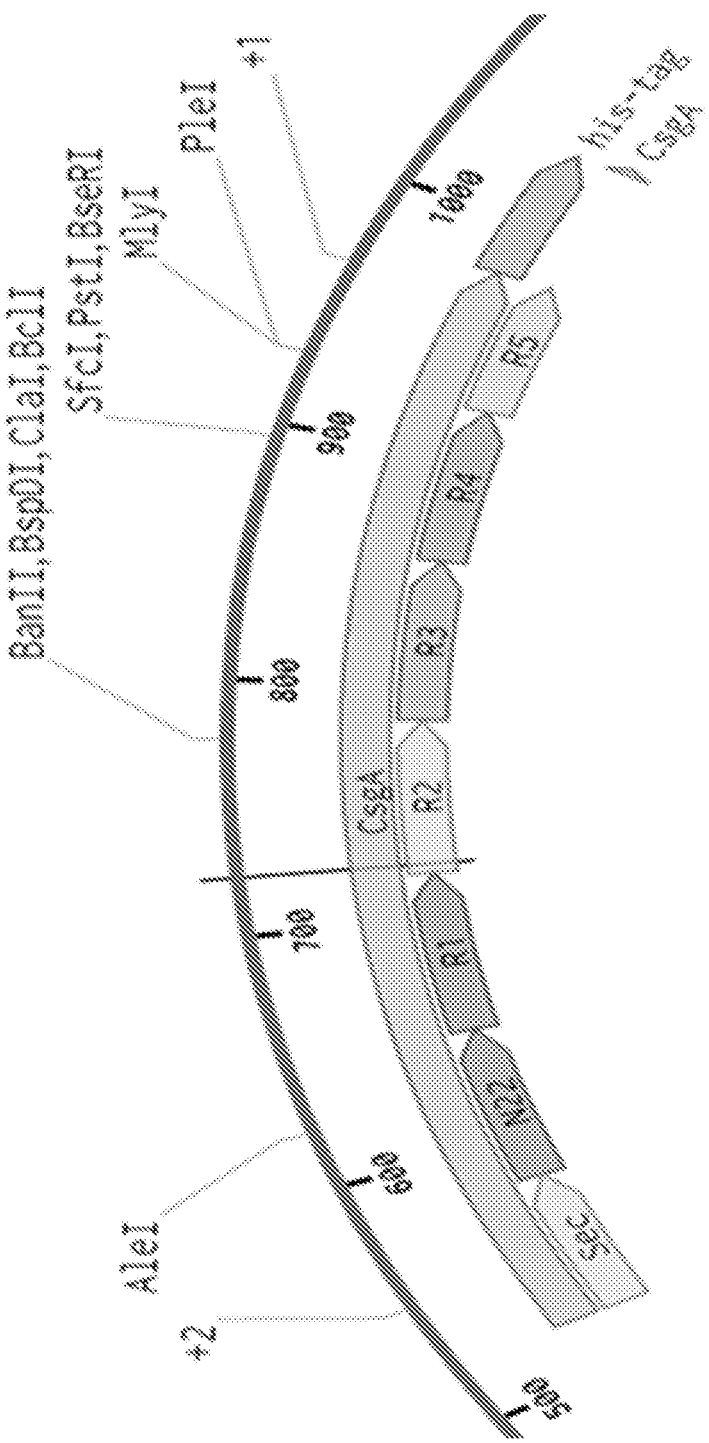

According to one aspect, a series of mutants that contain up to 5 mutations (1 per repeat) is created that result in the alignment of aromatic amino acids on the exterior of the CsgA β-helix (FIG. 3B). A representative example of one mutant containing 5 aligned histidine residues demonstrates their alignment in two consecutive CsgA monomers. Histidine is used as an example because it is isosteric with 3-thienylalanine, but other aromatic amino acids that are purported to be involved in long range EET in the *G. sulfurreducens* PilA nanowire (i.e., tyrosine and tryptophan) are also exemplary. The CsgA mutants are expressed recombinantly from a system developed that includes a plasmid containing a synthetic curli operon in an engineered strain containing the entire curli operon deleted. The amyloid production in each mutant is monitored using a standard plate-based Congo Red assay. A diagnostic device has been created to enable simultaneous monitoring of ~100s of bacterial colonies using time-lapse photography, facilitating the rapid identification of "hits" from relatively large libraries of *E. coli* variants. The hits are subsequently characterized using whole cell ELISA, TEM, and SEM on intact biofilms to confirm the identity and morphology of the mutant amyloid fibers. AFM of purified curli fibers is also conducted to confirm fiber dimensions. The variants are subjected to growth curve analyses to approximate the effects of the mutations on organismal fitness. Growth rates comparable to cells recombinantly producing the wild-type CsgA sequence are considered acceptable. According to one aspect, natural aromatic amino acids are sufficient to convey a base level of electronic conductance. According to one aspect, non-standard amino acid residues (NSAAs) are sufficient to convey a base level of electronic conductance. According to this aspect, an orthogonal set of tRNAs and aminoacyl-tRNA synthetases (aaRSs) are used to specifically incorporate synthetic amino acids. See Xiao, H. et al. Genetic Incorporation of Histidine Derivatives Using an Engineered PyrrolysyltRNA Synthetase. ACS Chemical Biology 9, 1092-1096 (2014) hereby incorporated by reference in its entirety. This requires the reassignment of the UAG stop codon (or another codon) to code for the NSAA. An MG1655-derived *E. coli* strain is specifically engineered to enable high-fidelity site-specific NSAA incorporation by having all of the genomic copies of the UAG stop codons removed. See Lajoie, M. J., Rovner, A. J., Goodman, D. B. & Aerni, H. R. Genomically recoded organisms expand biological functions. Science (2013) hereby incorporated by reference in its entirety.

The system is used to incorporate 3-thienylalanine (3-Th) into the permissive sites in the CsgA sequence, as determined by the above mutagenesis experiments. 3-Th is advantageous because of its similarity to the thiophene functional groups that pervade the field of conjugated conductive polymers, but several other non-standard amino acids are useful, including fluorinated phenylalanine analogs. See Mottishaw, J. D. & Sun, H. Effects of Aromatic Trifluoromethylation, Fluorination, and Methylation on Intermolecular π-π Interactions. *J. Phys. Chem. A* 117, 7970-9 (2013) hereby incorporated by reference in its entirety. Successful NSAA incorporation is determined by trypsin digest followed by LC/MS/MS analysis. Amyloid fiber formation ability for the 3-Th CsgA mutants is assayed as described above.

Example III

Screening of Curli Library for Electrical Conductivity

Successful mutants or "hits" that emerge from the screening protocol above are confirmed to secrete and assemble CsgA variants into microns long amyloid fibers containing aligned, consecutive aromatic amino acids where the synthetic amyloids exhibit measurable electrical conductivity. See Amit, M., Cheng, G., Hamley, I. W. & Ashkenasy, N. Conductance of amyloid β based peptide filaments: structure-function relations. *Soft Matter* 8, 8690 (2012); Del Mercato, L. L. et al. Charge transport and intrinsic fluorescence in amyloid-like fibrils. *Proceedings of the National Academy of Sciences* 104, 18019-18024 (2007); Amdursky, N. Enhanced solid-state electron transport via tryptophan containing peptide networks. *Phys. Chem. Chem. Phys.* 15, 13479 (2013) each of which are hereby incorporated by reference in its entirety. Computational studies of amyloid folds containing stacked thienyl moieties indicate that a spacing on the order of 4-6 Å is sufficient to allow for delocalization. See Hamley, I. W. et al. Self-Assembly of a Designed Amyloid Peptide Containing the Functional Thienylalanine Unit. *J. Phys. Chem. B* 114, 10674-10683 (2010) hereby incorporated by reference in its entirety. Based on a computationally derived structure for CsgA, the proposed mutations exhibit an average distance of 5.11 Å between their respective β-carbons. In order to screen the narrowed library for conductive properties, the modified curli fibers are purified using standard protocols and measure their absorbance and fluorescence spectra under oxidizing and reducing conditions. See Tian, P. et al. Structure of a Functional Amyloid Protein Subunit Computed Using Sequence Variation. *J Am Chem Soc* 137, 22-25 (2015); Wang, X. & Chapman, M. R. Sequence Determinants of Bacterial Amyloid Formation. *J Mol Biol* 380, 570-580 (2008) hereby incorporated by reference in its entirety. The readout for delocalization is red-shifted in emission wavelength coupled with a decrease in intensity. Conductivity is measured directly by conductive AFM (ORCA) measurements on purified curli fibers. Finally, 96-well plates with an embedded array of addressable electrodes are used (Applied Biophysics, Inc.) to monitor bulk conductivity in intact biofilms.

Example IV

Assessing the Ability of Conductive Fibers to Enhance EET Between Electrodes and Bacteria Biosynthetically produced conductive nanofibers are useful for several applications independently. Biosynthetically produced conductive nanofibers are also useful to mediate electron transport between electrodes and bacteria with the ability to use electrons directly as terminal electron acceptors in their metabolism. This is accomplished by using methods analogous to genetic engineering of the pili synthesized by microbes naturally, heterologously expressing the conductive curli fibers in the electroactive bacteria, or co-culturing two different bacterial species. According to one aspect of hybrid biofilm formation, the conductive matrix is created by engineered *E. coli* in an initial step, followed by colonization of the matrix with a different *E. coli* strain that has been specifically engineered to use external electrodes as terminal acceptors in its metabolism. See Jensen, H. M. et al. Engineering of a synthetic electron conduit in living cells. *Proc. Natl. Acad. Sci. USA* 107, 19213-8 (2010) hereby incorporated by reference in its entirety.

Example V

Cell Strains and Plasmids

All cloning was performed in Mach1 cells.

For fibers containing only natural amino acids, the CsgA gene was isolated from *E. coli* K12 and cloned in a pET21d plasmid, under the control of the T7 promoter. A six his tag was added to the N-terminus of CsgA to allow for protein purification. Aromatic amino acid mutations were introduced in CsgA using gBlocks gene fragments (Integrated DNA Technologies) containing the point mutations, and isothermal Gibson assembly. Protein expression was performed in PQN4, an *E. coli* strain derived from LSR10, in which the curli operon was knocked out to prevent any background expression level of wild-type curli fibers.

For fibers containing non-natural amino acids, the CsgA gene was cloned in a pBbB8k or pBbB8a vector under the control of a PBAD vector, and a six his tag was added to the N-terminus of CsgA. Mutations were introduced in CsgA using gBlocks gene fragments with UAG codons at the desired mutation sites, and isothermal assembly was used to generate the mutant plasmids. Protein expression was performed in C321.ΔA.exp (obtained from Addgene, Bacterial strain #49018), an *E. coli* strain in which UAG codons have been removed from the genome to allow for non-natural amino acid incorporation. C321.ΔA.exp are co-transformed with a plasmid coding for CsgA, along with a plasmid coding for the aminoacyl-tRNA synthetase and tRNA specific for a non-natural amino acid of interest. A plasmid specific for 2-thienylalanine or 3-thienylalanine (pKB-pylHRS plasmid) was used and plasmids specific for p-acetylphenylalanine (pEVOL-pAcF plasmid), and p-azidophenylalanine (pEVOL-pAzF plasmid) were used. For protein expression, the non-natural amino acid of interest is added to the culture medium at induction.

Example VI

Designing Conductive CsgA Proteins

Mutations introduced in CsgA are referred to by residue number for single mutations, or by stacks for groups of four or five residues mutated together. The residues selected for mutations corresponding to each stack are listed below. The numbering begins at the first glycine residues in the N22 peptide (it excludes the Sec peptide). Residues selected for mutations face outward (exposed to the solvent), and are located in the β-sheets of CsgA. Each stack represents an aligned series of residues useful in forming pi-stacks.

Stack 1: Glu 24, Asp 47, Ser 69, Glu 92, Ser 114 (SEQ ID NO:45)
Stack 2: Asn 26, Thr 49, Asp 71, Thr 94, Asn 116 (SEQ ID NO:46)
Stack 3: Thr 51, Thr 73, Lys 96, Thr 118 (SEQ ID NO:47)
Stack 4: Ala 38, Asp 60, Thr 82, Ala 105, Thr 127 (SEQ ID NO:48)

Stack 5: Gln 40, Gly 62, Asp 84, Asp 107 (SEQ ID NO:49)

The residues in each stack were simultaneously mutated to tyrosine. Then, for stack 1, the residues were also simultaneously mutated to tryptophan, phenylalanine or histidine, or to a non-natural amino acid. In addition, all five stacks were mutated together to tyrosine (23 mutations) in a single mutant.

TABLE 1 gBlock gene fragments used to produce the CsgA mutants with stacked aromatic residues or fusions comprising redox active domains (e.g., metalloproteins or domains thereof), and corresponding primers used to linearize the plasmids. NSAA stands for non-standard amino acid.

| CONSTRUCT | GBLOCK GENE FRAGMENT (5' TO 3') | PRIMERS USED TO LINEARIZE THE PLASMID BEFORE GIBSON ASSEMBLY (5' TO 3') |
|---|---|---|
| Stack 1-Tyr | ACGGTGGTGGCGGTAATAATAGCGGCCCAAATTCTTA TCTGAACATTTACCAGTACGGTGGCGGTAACTCTGCA CTTGCTCTGCAAACTGATGCCCGTAACTCTTACTTGAC TATTACCCAGCATGGCGGCGGTAATGGTGCAGATGTT GGTCAGGGCTCAGATGACAGCTATATCGATCTGACCC AACGTGGCTTCGGTAACAGCGCTACTCTTGATCAGTG GAACGGCAAAAATTCTTATATGACGGTTAAACAGTTC GGTGGTGGCAACGGTGCTGCAGTTGACCAGACTGCAT CTAACTCCTACGTCAACGTGACTCAGGTTGGCTTTGG TAAC (SEQ ID NO: 3) | Fwd: GTGACTCAGGTT GGCTTTGGTAAC AACGCGACCG (SEQ ID NO: 82) Rev: GAATTTGGGCCG CTATTATTACCG CCACCA (SEQ ID NO: 83) |
| Stack 2-Tyr | GGTAATAATAGCGGCCCAAATTCTGAGCTGTACATTT ACCAGTACGGTGGCGGTAACTCTGCACTTGCTCTGCA AACTGATGCCCGTAACTCTGACTTGTATATTACCCAG CATGGCGGCGGTAATGGTGCAGATGTTGGTCAGGGCT CAGATGACAGCTCAATCTATCTGACCCAACGTGGCTT CGGTAACAGCGCTACTCTTGATCAGTGGAACGGCAAA AATTCTGAAATGTATGTTAAACAGTTCGGTGGTGGCA ACGGTGCTGCAGTTGACCAGACTGCATCTAACTCCTC CGTCTACGTGACTCAGGTTGGCTTTGGTAACAACGCG (SEQ ID NO: 4) | Fwd: GTGACTCAGGTT GGCTTTGGTAAC AACGCGACCG (SEQ ID NO: 82) Rev: GAATTTGGGCCG CTATTATTACCG CCACCA (SEQ ID NO: 83) |
| Stack 3-Tyr | ACTGATGCCCGTAACTCTGACTTGACTATTTACCAGC ATGGCGGCGGTAATGGTGCAGATGTTGGTCAGGGCTC AGATGACAGCTCAATCGATCTGTACCAACGTGGCTTC GGTAACAGCGCTACTCTTGATCAGTGGAACGGCAAAA ATTCTGAAATGACGGTTTATCAGTTCGGTGGTGGCAA CGGTGCTGCAGTTGACCAGACTGCATCTAACTCCTCC GTCAACGTGTATCAGGTTGGCTTTGGTAACAACGCGA CCGCT (SEQ ID NO: 5) | Fwd: CAGGTTGGCTTT GGTAACAACGCG ACCGCTCATCAG (SEQ ID NO: 84) Rev: TAGTCAAGTCAG AGTTACGGGCAT CAGTTT (SEQ ID NO: 85) |
| Stack 4-Tyr | TACCAGTACGGTGGCGGTAACTCTGCACTTTATCTGC AAACTGATGCCCGTAACTCTGACTTGACTATTACCCA GCATGGCGGCGGTAATGGTGCATATGTTGGTCAGGGC TCAGATGACAGCTCAATCGATCTGACCCAACGTGGCT TCGGTAACAGCGCTTATCTTGATCAGTGGAACGGCAA AAATTCTGAAATGACGGTTAAACAGTTCGGTGGTGGC AACGGTGCTTATGTTGACCAGACTGCATCTAACTCCT CCGTCAACGTGACTCAGGTTGGCTTTGGTAACAACGC GTATGCTCATCAGTACGGcTCTGGTGGcTCTGGT (SEQ ID NO: 6) | Fwd: CAGTACGGCTCT GGTGGCTCTGGT GGCTCT (SEQ ID NO: 86) Rev: AAGTGCAGAGTT ACCGCCACCGTA CTGG (SEQ ID NO: 87) |
| Stack 5-Tyr | TACGGTGGCGGTAACTCTGCACTTGCTCTGTATACTG ATGCCCGTAACTCTGACTTGACTATTACCCAGCATGG CGGCGGTAATGGTGCAGATGTTTATCAGGGCTCAGAT GACAGCTCAATCGATCTGACCCAACGTGGCTTCGGTA ACAGCGCTACTCTTTATCAGTGGAACGGCAAAAATTC TGAAATGACGGTTAAACAGTTCGGTGGTGGCAACGGT GCTGCAGTTTACCAGACTGCATCTAACTCCTCCGTCA ACGTG (SEQ ID NO: 7) | Fwd: GACTGCATCTAA CTCCTCCGTCAA CGTGAC (SEQ ID NO: 88) Rev: AAGTGCAGAGTT ACCGCCACCGTA CTGG (SEQ ID NO: 87) |
| Stack 1-Trp | ACGGTGGTGGCGGTAATAATAGCGGCCCAAATTCTTG GCTGAACATTTACCAGTACGGTGGCGGTAACTCTGCA CTTGCTCTGCAAACTGATGCCCGTAACTCTTGGTTGAC TATTACCCAGCATGGCGGCGGTAATGGTGCAGATGTT | Fwd: GTGACTCAGGTT GGCTTTGGTAAC AACGCGACCG |

TABLE 1-continued gBlock gene fragments used to produce the CsgA mutants with stacked aromatic residues or fusions comprising redox active domains (e.g., metalloproteins or domains thereof), and corresponding primers used to linearize the plasmids. NSAA stands for non-standard amino acid.

| CONSTRUCT | GBLOCK GENE FRAGMENT (5' TO 3') | PRIMERS USED TO LINEARIZE THE PLASMID BEFORE GIBSON ASSEMBLY (5' TO 3') |
|---|---|---|
|  | GGTCAGGGCTCAGATGACAGCTGGATCGATCTGACCC AACGTGGCTTCGGTAACAGCGCTACTCTTGATCAGTG GAACGGCAAAAATTCTTGGATGACGGTTAAACAGTTC GGTGGTGGCAACGGTGCTGCAGTTGACCAGACTGCAT CTAACTCCTGGGTCAACGTGACTCAGGTTGGCTTTGG TAAC (SEQ ID NO: 8) | (SEQ ID NO: 82) Rev: GAATTTGGGCCG CTATTATTACCG CCACCA (SEQ ID NO: 83) |
| Stack 2-Trp | GGTAATAATAGCGGCCCAAATTCTGAGCTGTGGA TTTACCAGTACGGTGGCGGTAACTCTGCACTTGC TCTGCAAACTGATGCCCGTAACTCTGACTTGTGG ATTACCCAGCATGGCGGCGGTAATGGTGCAGATG TTGGTCAGGGCTCAGATGACAGCTCAATCGGCT GACCCAACGTGGCTTCGGTAACAGCGCTACTCTT GATCAGTGGAACGGCAAAAATTCTGAAATGTGG GTTAAACAGTTCGGTGGTGGCAACGGTGCTGCAG TTGACCAGACTGCATCTAACTCCTCCGTCTGGGT GACTCAGGTTGGCTTTGGTAACAACGCG (SEQ ID NO: 62) | Fwd: GTGACTCAGGT TGGCTTTGGTA ACAACGCGACC G (SEQ ID NO: 82) Rev: GAATTTGGGCC GCTATTATTAC CGCCACCA (SEQ ID NO: 83) |
| Stack 3-Trp | ACTGATGCCCGTAACTCTGACTTGACTATTGGC AGCATGGCGGCGGTAATGGTGCAGATGTTGGTCA GGGCTCAGATGACAGCTCAATCGATCTGTGGCAA CGTGGCTTCGGTAACAGCGCTACTCTTGATCAGT GGAACGGCAAAAATTCTGAAATGACGGTTTGGC AGTTCGGTGGTGGCAACGGTGCTGCAGTTGACCA GACTGCATCTAACTCCTCCGTCAACGTGTGGCAG GTTGGCTTTGGTAACAACGCGACCGCT (SEQ ID NO: 63) | Fwd: CAGGTTGGCTT TGGTAACAACG CGACCGCTCAT CAG (SEQ ID NO: 89) Rev: TAGTCAAGTCA GAGTTACGGGC ATCAGTTT (SEQ ID NO: 85) |
| Stack 4-Trp | TACCAGTACGGTGGCGGTAACTCTGCACTTTGGC TGCAAACTGATGCCCGTAACTCTGACTTGACTAT TACCCAGCATGGCGGCGGTAATGGTGCATGGGTT GGTCAGGGCTCAGATGACAGCTCAATCGATCTGA CCCAACGTGGCTTCGGTAACAGCGCTTGGCTTGA TCAGTGGAACGGCAAAAATTCTGAAATGACGGTT AAACAGTTCGGTGGTGGCAACGGTGCTTGGGTTG ACCAGACTGCATCTAACTCCTCCGTCAACGTGAC TCAGGTTGGCTTTGGTAACAACGCGTGGGCTCAT CAGTACGGcTCTGGTGGcTCTGGT (SEQ ID NO: 64) | Fwd: CAGTACGGCTC TGGTGGCTCTG GTGGCTCT (SEQ ID NO: 86) Rev: AAGTGCAGAGT TACCGCCACCG TACTGG (SEQ ID NO: 87) |
| Stack 5-Trp | TACGGTGGCGGTAACTCTGCACTTGCTCTGTGGA CTGATGCCCGTAACTCTGACTTGACTATTACCCA GCATGGCGGCGGTAATGGTGCAGATGTTTGGCAG GGCTCAGATGACAGCTCAATCGATCTGACCCAAC GTGGCTTCGGTAACAGCGCTACTCTTTGGCAGTG GAACGGCAAAAATTCTGAAATGACGGTTAAACA GTTCGGTGGTGGCAACGGTGCTGCAGTTTGGCAG ACTGCATCTAACTCCTCCGTCAACGTG (SEQ ID NO: 65) | Fwd: GACTGCATCTA ACTCCTCCGTC AACGTGAC (SEQ ID NO: 88) Rev: AAGTGCAGAGT TACCGCCACCG TACTGG (SEQ ID NO: 87) |
| Stack 1-Phe | ACGGTGGTGGCGGTAATAATAGCGGCCCAAATTCTTT TCTGAACATTTACCAGTACGGTGGCGGTAACTCTGCA CTTGCTCTGCAAACTGATGCCCGTAACTCTTTCTTGAC TATTACCCAGCATGGCGGCGGTAATGGTGCAGATGTT GGTCAGGGCTCAGATGACAGCTTTATCGATCTGACCC AACGTGGCTTCGGTAACAGCGCTACTCTTGATCAGTG GAACGGCAAAAATTCTTTTATGACGGTTAAACAGTTC GGTGGTGGCAACGGTGCTGCAGTTGACCAGACTGCAT CTAACTCCTTCGTCAACGTGACTCAGGTTGGCTTTGGT AAC (SEQ ID NO: 9) | Fwd: GTGACTCAGGTT GGCTTTGGTAAC AACGCGACCG (SEQ ID NO: 82) Rev: GAATTTGGGCCG CTATTATTACCG CCACCA (SEQ ID NO: 83) |
| Stack 1-His | ACGGTGGTGGCGGTAATAATAGCGGCCCAAATTCTCA TCTGAACATTTACCAGTACGGTGGCGGTAACTCTGCA CTTGCTCTGCAAACTGATGCCCGTAACTCTCACTTGAC TATTACCCAGCATGGCGGCGGTAATGGTGCAGATGTT GGTCAGGGCTCAGATGACAGCCATATCGATCTGACCC | Fwd: GTGACTCAGGTT GGCTTTGGTAAC AACGCGACCG (SEQ ID NO: 82) |

TABLE 1-continued gBlock gene fragments used to produce the CsgA mutants with stacked aromatic residues or fusions comprising redox active domains (e.g., metalloproteins or domains thereof), and corresponding primers used to linearize the plasmids. NSAA stands for non-standard amino acid.

| CONSTRUCT | GBLOCK GENE FRAGMENT (5' TO 3') | PRIMERS USED TO LINEARIZE THE PLASMID BEFORE GIBSON ASSEMBLY (5' TO 3') |
|---|---|---|
| | AACGTGGCTTCGGTAACAGCGCTACTCTTGATCAGTG GAACGGCAAAAATTCTCATATGACGGTTAAACAGTTC GGTGGTGGCAACGGTGCTGCAGTTGACCAGACTGCAT CTAACTCCCACGTCAACGTGACTCAGGTTGGCTTTGG TAAC (SEQ ID NO: 10) | Rev: GAATTTGGGCCG CTATTATTACCG CCACCA (SEQ ID NO: 83) |
| Stack 1,2,3,4 and 5-Tyr | ACGGTGGTGGCGGTAATAATAGCGGCCCAAATTCTTA TCTGTATATTTACCAGTACGGTGGCGGTAACTCTGCA CTTTATCTGTATACTGATGCCCGTAACTCTTACTTGTA TATTTATCAGCATGGCGGCGGTAATGGTGCATATGTT TATCAGGGCTCAGATGACAGCTATATCTATCTGTATC AACGTGGCTTCGGTAACAGCGCTTATCTTTATCAGTG GAACGGCAAAAATTCTTATATGTATGTTTATCAGTTC GGTGGTGGCAACGGTGCTTATGTTTATCAGACTGCAT CTAACTCCTACGTCTATGTGTATCAGGTTGGCTTTGGT AACAACGCGTATGCTCATCAGTACGGCTCTGGTGGcTC TGGT (SEQ ID NO: 11) | Fwd: CAGTACGGCTCT GGTGGCTCTGGT GGCTCT (SEQ ID NO: 86) Rev: GAATTTGGGCCG CTATTATTACCG CCACCA (SEQ ID NO: 83) |
| Stack-NSAA | ACGGTGGTGGCGGTAATAATAGCGGCCCAAATTCTTA GCTGAACATTTACCAGTACGGTGGCGGTAACTCTGCA CTTGCTCTGCAAACTGATGCCCGTAACTCTTAGTTGAC TATTACCCAGCATGGCGGCGGTAATGGTGCAGATGTT GGTCAGGGCTCAGATGACAGCTAGATCGATCTGACCC AACGTGGCTTCGGTAACAGCGCTACTCTTGATCAGTG GAACGGCAAAAATTCTTAGATGACGGTTAAACAGTTC GGTGGTGGCAACGGTGCTGCAGTTGACCAGACTGCAT CTAACTCCTAGGTCAACGTGACTCAGGTTGGCTTTGG TAAC (SEQ ID NO: 12) | Fwd: GTGACTCAGGTT GGCTTTGGTAAC AACGCGACCG (SEQ ID NO: 82) Rev: GAATTTGGGCCG CTATTATTACCG CCACCA (SEQ ID NO: 83) |
| Microperoxi-dase-8 fusion | GTAACAACGCGACCGCTCATCAGTACGGTGGATC TGGTAGCAGCGGCTCTGGTGGTTCTGGGGGCGGA AGTGGCTCCTCTGGGAGCGGGGGGTCGGGTGGT GGCTCGGGTTCATCTGGTAGTGGCGGTTCGGGTT GCGCGCAGTGCCATACCGTGGAAGGcTCTGGTGG cTCTGGTGGcTCTGGcGGCAGCGGGCAtCACCACC ACCATCATTAATACATCATTTGTATTACAGAAAC AGGGC (SEQ ID NO: 66) | |
| Microperoxi-dase-9 fusion | TAACAACGCGACCGCTCATCAGTACGGTGGATCT GGTAGCAGCGGCTCTGGTGGTTCTGGGGGCGGA AGTGGCTCCTCTGGGAGCGGGGGGTCGGGTGGT GGCTCGGGTTCATCTGGTAGTGGCGGTTCGGGTT GCGCGCAGTGCCATACCGTGGAAAAAGGcTCTGG TGGcTCTGGTGGcTCTGGcGGCAGCGGGCAtCACC ACCACCATCATTAATACATCATTTGTATTACAGA AACAGGGC (SEQ ID NO: 67) | |
| Microperoxi-adse-11 fusion | ACAACGCGACCGCTCATCAGTACGGTGGATCTGG TAGCAGCGGCTCTGGTGGTTCTGGGGGCGGAAGT GGCTCCTCTGGGAGCGGGGGGTCGGGTGGTGGCT CGGGTTCATCTGGTAGTGGCGGTTCGGGTGTGCA GAAATGCGCAGTGCCATACCGTGGAAGGcTCT GGTGGcTCTGGTGGcTCTGGcGGCAGCGGGCAtCA CCACCACCATCATTAATACATCATTTGTATTACA G (SEQ ID NO: 68) | |
| Plastocyanin fusion | ACAACGCGACCGCTCATCAGTACGGTGGATCTGG TAGCAGCGGCTCTGGTGGTTCTGGGGGCGGAAGT GGCTCCTCTGGGAGCGGGGGGTCGGGTGGTGGCT CGGGTTCATCTGGTAGTGGCGGTTCGGGTATGAT TTCCTCGCTTCGCTCAGCGCTATCTGCATGTTTTG CATTGCTTTTGGTGCTTGCCTTTGGAGTTGCATCC GCACAAGCTAAAACAGTTGAAGTAAAACTAGGA ACTGATGCTGGAATGCTTGCATTCGAACCCAGCT CTGTAACCATAAGTACTGGCGACTCTGTGAAGTT TGTCAACAACAAACTTGCTCCTCACAATGCAGTT TTTGAAGGTCATGAAGAATTAAGTCATCCTGACC TTGCTTTTGCTCCTGGCAAAGCTGGCAAGAAAC TTTTACAGAAGCAGGTACATATGACTATTACTGC | |

TABLE 1-continued gBlock gene fragments used to produce the CsgA mutants with stacked aromatic residues or fusions comprising redox active domains (e.g., metalloproteins or domains thereof), and corresponding primers used to linearize the plasmids. NSAA stands for non-standard amino acid.

| CONSTRUCT | GBLOCK GENE FRAGMENT (5' TO 3') | PRIMERS USED TO LINEARIZE THE PLASMID BEFORE GIBSON ASSEMBLY (5' TO 3') |
|---|---|---|
| | GAGCCTCATAGAGGAGCAGGGATGGTCGGGAAA GTAGTTGTTAACGGcTCTGGTGGcTCTGGTGGcTC TGGcGGCAGCGGGCAtCACCACCACCATCATTAAT ACATCATTTGTATTACAGAAACAGGGC (SEQ ID NO: 69) | |
| Mitochondrial ferritin fusion | AACGCGACCGCTCATCAGTACGGTGGATCTGGTA GCAGCGGCTCTGGTGGTTCTGGGGGCGGAAGTG GCTCCTCTGGGAGCGGGGGGTCGGGTGGTGGCTC GGGTTCATCTGGTAGTGGCGGTTCGGGTATGCTG TCTGGTTTCTGGTTCTTCTCCAAGCACATCGGCCC TGCATTGATGTCCTTGCCCCGTGTGCTACACAGG TGCACTGTCCCACAGTGTTTGGCCTCCAGGTATC CTTTACTACCCGCCTCCCCTCGACGTCTGCTGGCC TCGGTGGCCTCCTCCCAGGGCTCTGATGGAACTG CCAGGGTGCGCCACAACTTTCACCCAGACTCTGA GGCAGCCATCAACCACCAAATCAACATGGAGCTT TACGCATCCTACGTGTACCTGTCCATGGCCTACT ACTTCTCCAGGGATGATGTGGCCTTGTACAACTT CTCCAAGTCTTTCCTTCGCCAGTCGCTGGAGGAG AGGGAGCATGCAGAGAAGCTAATGAAGCTGCAG AACCAACGCGGAGGCCGGATCTGCCTCCAGGAT ATCAAGAAGCCAGAGCAAGATGACTGGGAGAGC GGACTGCGGGCCATGGAATGTGCTCTGCTCCTGG AAAAGAGTGTAAACCAGTCGCTGCTGGACCTGC ATACTCTGGCCTCAGAAAAAGGAGATCCTCATTT GTGCGACTTTCTGGAAACACACTACCTGAATGAG CAGGTGAAGTCTATCAAAGAATTAGGTGACCAC GTGCACAACTTAGTCACCATGGGGGCTCCAGCTG TTGGCCTAGCGGAGTACCTTTTTGACAAGCACAC CCTTGGAAGTGAGAGCAAGCACGGcTCTGGTGGc TCTGGTGGcTCTGGcGGCAGCGGGCAtCACCACCA CCATCATTAATACATCATTTGTATTAC (SEQ ID NO: 70) | |
| Rubredoxin fusion | AACGCGACCGCTCATCAGTACGGTGGATCTGGTA GCAGCGGCTCTGGTGGTTCTGGGGGCGGAAGTG GCTCCTCTGGGAGCGGGGGGTCGGGTGGTGGCTC GGGTTCATCTGGTAGTGGCGGTTCGGGTATGGCA AAGTGGGTTTGTAAGATATGCGGATACATATATG ATGAAGATGCAGGAGATCCAGACAATGGTATTTC TCCTGGAACTAAGTTTGAGGAGCTACCAGATGAT TGGGTTTGCCCCATTTGTGGGGCTCCAAAAAGTG AATTTGAAAAGTTAGAAGATGGcTCTGGTGGcTCT GGTGGcTCTGGcGGCAGCGGGCAtCACCACCACCA TCATTAATACATCATTTGTATTACAGAAACAGGG C (SEQ ID NO: 71) | |

TABLE 2

Protein sequence and expected molecular weight of the mutants containing stacked aromatic amino acids or fusions comprising redox active domains (e.g., metalloproteins or domains thereof). The Sec peptide (underlined) has a molecular weight of 1974.5 Da, which should be subtracted from the molecular weight of the protein after CsgA is secreted outside of the cell, as Sec is cleaved. The molecular weight of wild-type CsgA with his-tag and Sec peptide is 16677 Da. The Sec peptide in each of the protein sequences below is underlined. His-tags (and corresponding flexible linkers) are italicized. The flexible linkers between fusion proteins are also italicized.

| CONSTRUCT | PROTEIN SEEQUENCE (INCLUDING SEC PEPTIDE) FOR HIS-TAGGED PROTEINS | EXPECTED MOLECULAR WEIGHT BEFORE CLEAVAGE OF THE SEC PEPTIDE (DA) |
|---|---|---|
| Stack 1-Tyr Sec peptide is underlined; linker and His-tag sequences are italicized. | MKLLKVAAIAAIVFSGSALAGVVPQYGGGGNHGG GGNNSGPNSYLNIYQYGGGNSALALQTDARNSYLT ITQHGGGNGADVGQGSDDSYIDLTQRGFGNSATLD QWNGKNSYMTVKQFGGGNGAAVDQTASNSYVNV TQVGFGNNATAHQY*GSGGSGGSGGSGHHHHHH**\* (SEQ ID NO: 13) | 169452 |
| Stack 2-Tyr Sec peptide is underlined; linker and His-tag sequences are italicized. | MKLLKVAAIAAIVFSGSALAGVVPQYGGGGNHGG GGNNSGPNSELYIYQYGGGNSALALQTDARNSDLY ITQHGGGNGADVGQGSDDSSIYLTQRGFGNSATLD QWNGKNSEMYVKQFGGGNGAAVDQTASNSSVYV TQVGFGNNATAHQY*GSGGSGGSGGSGHHHHHH**\* (SEQ ID NO: 14) | 16947 |
| Stack 3-Tyr Sec peptide is underlined; linker and His-tag sequences are italicized. | MKLLKVAAIAAIVFSGSALAGVVPQYGGGGNHGG GGNNSGPNSELNIYQYGGGNSALALQTDARNSDLT IYQHGGGNGADVGQGSDDSSIDLYQRGFGNSATLD QWNGKNSEMTVYQFGGGNGAAVDQTASNSSVNV YQVGFGNNATAHQY*GSGGSGGSGGSGHHHHHH**\* (SEQ ID NO: 15) | 16897 |
| Stack 4-Tyr Sec peptide is underlined; linker and His-tag sequences are italicized. | MKLLKVAAIAAIVFSGSALAGVVPQYGGGGNHGG GGNNSGPNSELNIYQYGGGNSALYLQTDARNSDLT ITQHGGGNGAYVGQGSDDSSIDLTQRGFGNSAYLD QWNGKNSEMTVKQFGGGNGAYVDQTASNSSVNV TQVGFGNNAYAHQY*GSGGSGGSGGSGHHHHHH**\* (SEQ ID NO: 16) | 17033 |
| Stack 5-Tyr Sec peptide is underlined; linker and His-tag sequences are italicized. | MKLLKVAAIAAIVFSGSALAGVVPQYGGGGNHGG GGNNSGPNSELNIYQYGGGNSALALYTDARNSDLT ITQHGGGNGADVYQGSDDSSIDLTQRGFGNSATLY QWNGKNSEMTVKQFGGGNGAAVYQTASNSSVNV TQVGFGNNATAHQY*GSGGSGGSGGSGHHHHHH**\* (SEQ ID NO: 17) | 16914 |
| Stack 1-Trp Sec peptide is underlined; linker and His-tag sequences are italicized. | MKLLKVAAIAAIVFSGSALAGVVPQYGGGGNHGG GGNNSGPNSWLNIYQYGGGNSALALQTDARNSWL TITQHGGGNGADVGQGSDDSWIDLTQRGFGNSATL DQWNGKNSWMTVKQFGGGNGAAVDQTASNSWV NVTQVGFGNNATAHQY*GSGGSGGSGGSGHHHHHH**\* (SEQ ID NO: 18) | 17060 |
| Stack 2-Trp | MKLLKVAAIAAIVFSGSALAGVVPQYGGGGNHGG GGNNSGPNSELWIYQYGGGNSALALQTDARNSDL WITQHGGGNGADVGQGSDDSSIWLTQRGFGNSAT LDQWNGKNSEMWVKQFGGGNGAAVDQTASNSSV WVTQVGFGNNATAHQY*GSGGSGGSGGSGHHHHHH* (SEQ ID NO: 72) | 17062 |
| Stack 3-Trp | MKLLKVAAIAAIVFSGSALAGVVPQYGGGGNHGG GGNNSGPNSELNIYQYGGGNSALALQTDARNSDLT IWQHGGGNGADVGQGSDDSSIDLWQRGFGNSATL DQWNGKNSEMTVWQFGGGNGAAVDQTASNSSVN VWQVGFGNNATAHQY*GSGGSGGSGGSGHHHHHH* (SEQ ID NO: 73) | 16990 |
| Stack 4-Trp | MKLLKVAAIAAIVFSGSALAGVVPQYGGGGNHGG GGNNSGPNSELNIYQYGGGNSALWLQTDARNSDL | 17148 |

TABLE 2-continued

Protein sequence and expected molecular weight of the mutants containing stacked aromatic amino acids or fusions comprising redox active domains (e.g., metalloproteins or domains thereof). The Sec peptide (underlined) has a molecular weight of 1974.5 Da, which should be subtracted from the molecular weight of the protein after CsgA is secreted outside of the cell, as Sec is cleaved. The molecular weight of wild-type CsgA with his-tag and Sec peptide is 16677 Da. The Sec peptide in each of the protein sequences below is underlined. His-tags (and corresponding flexible linkers) are italicized. The flexible linkers between fusion proteins are also italicized.

| CONSTRUCT | PROTEIN SEQUENCE (INCLUDING SEC PEPTIDE) FOR HIS-TAGGED PROTEINS | EXPECTED MOLECULAR WEIGHT BEFORE CLEAVAGE OF THE SEC PEPTIDE (DA) |
|---|---|---|
| | TITQHGGGNGAWVGQGSDDSSIDLTQRGFGNSAW LDQWNGKNSEMTVKQFGGGNGAWVDQTASNSSV NVTQVGFGNNAWAHQY*GSGGSGGSGGSGHHHHH H* (SEQ ID NO: 74) | |
| Stack 5-Trp | <u>MKLLKVAAIAAIVFSGSALA</u>GVVPQYGGGGNHGG GGNNSGPNSELNIYQYGGGNSALALWTDARNSDL TITQHGGGNGADVWQGSDDSSIDLTQRGFGNSATL WQWNGKNSEMTVKQFGGGNGAAVWQTASNSSV NVTQVGFGNNATAHQY*GSGGSGGSGGSGHHHHHH* (SEQ ID NO: 75) | 17006 |
| Stack 1-Phe Sec peptide is underlined; linker and His-tag sequences are italicized. | <u>MKLLKVAAIAAIVFSGSALA</u>GVVPQYGGGGNHGG GGNNSGPNSFLNIYQYGGGNSALALQTDARNSFLTI TQHGGGNGADVGQGSDDSFIDLTQRGFGNSATLD QWNGKNSFMTVKQFGGGNGAAVDQTASNSFVNV TQVGFGNNATAHQY*GSGGSGGSGGSGHHHHHH** (SEQ ID NO: 19) | 16865 |
| Stack 1-His Sec peptide is underlined; linker and His-tag sequences are italicized. | <u>MKLLKVAAIAAIVFSGSALA</u>GVVPQYGGGGNHGG GGNNSGPNSHLNIYQYGGGNSALALQTDARNSHLT ITQHGGGNGADVGQGSDDSHIDLTQRGFGNSATLD QWNGKNSHMTVKQFGGGNGAAVDQTASNSHVNV TQVGFGNNATAHQY*GSGGSGGSGGSGHHHHHH** (SEQ ID NO: 20) | 16815 |
| Stack 1,2,3,4 and 5-Tyr Sec peptide is underlined; linker and His-tag sequences are italicized. | <u>MKLLKVAAIAAIVFSGSALA</u>GVVPQYGGGGNHGG GGNNSGPNSYLYIYQYGGGNSALYLYTDARNSYL YIYQHGGGNGAYVYQGSDDSYIYLYQRGFGNSAY LYQWNGKNSYMYVYQFGGGNGAYVYQTASNSYV YVYQVGFGNNAYAHQY*GSGGSGGSGGSGHHHHH H** (SEQ ID NO: 21) | 18031 |
| Microperoxi- dase-8 fusion | <u>MKLLKVAAIAAIVFSGSALA</u>GVVPQYGGGGNHGG GGNNSGPNSELNIYQYGGGNSALALQTDARNSDLT ITQHGGGNGADVGQGSDDSSIDLTQRGFGNSATLD QWNGKNSEMTVKQFGGGNGAAVDQTASNSSVNV TQVGFGNNATAHQY*GGSGSSGSGGSGGGSGSSGSG GSGGGSGSSGSGGSG*CAQCHTVE*GSGGSGGSGGSG HHHHHH* (SEQ ID NO: 76) | 20052 |
| Microperoxi- dase-9 fusion | <u>MKLLKVAAIAAIVFSGSALA</u>GVVPQYGGGGNHGG GGNNSGPNSELNIYQYGGGNSALALQTDARNSDLT ITQHGGGNGADVGQGSDDSSIDLTQRGFGNSATLD QWNGKNSEMTVKQFGGGNGAAVDQTASNSSVNV TQVGFGNNATAHQY*GGSGSSGSGGSGGGSGSSGSG GSGGGSGSSGSGGSG*CAQCHTVEK*GSGGSGGSGGS GHHHHHH* (SEQ ID NO: 77) | 20181 |
| Microperoxi- dase-11 fusion | <u>MKLLKVAAIAAIVFSGSALA</u>GVVPQYGGGGNHGG GGNNSGPNSELNIYQYGGGNSALALQTDARNSDLT ITQHGGGNGADVGQGSDDSSIDLTQRGFGNSATLD QWNGKNSEMTVKQFGGGNGAAVDQTASNSSVNV TQVGFGNNATAHQY*GGSGSSGSGGSGGGSGSSGSG GSGGGSGSSGSGGSGVQKCAQCHTVE*GSGGSGGSG GSGHHHHHH* (SEQ ID NO: 78) | 20408 |
| Plastocyanin fusion | <u>MKLLKVAAIAAIVFSGSALA</u>GVVPQYGGGGNHGG GGNNSGPNSELNIYQYGGGNSALALQTDARNSDLT ITQHGGGNGADVGQGSDDSSIDLTQRGFGNSATLD | 31772 |

TABLE 2-continued

Protein sequence and expected molecular weight of the mutants containing stacked aromatic amino acids or fusions comprising redox active domains (e.g., metalloproteins or domains thereof). The Sec peptide (underlined) has a molecular weight of 1974.5 Da, which should be subtracted from the molecular weight of the protein after CsgA is secreted outside of the cell, as Sec is cleaved. The molecular weight of wild-type CsgA with his-tag and Sec peptide is 16677 Da. The Sec peptide in each of the protein sequences below is underlined.
His-tags (and corresponding flexible linkers) are italicized. The flexible linkers between fusion proteins are also italicized.

| CONSTRUCT | PROTEIN SEEQUENCE (INCLUDING SEC PEPTIDE) FOR HIS-TAGGED PROTEINS | EXPECTED MOLECULAR WEIGHT BEFORE CLEAVAGE OF THE SEC PEPTIDE (DA) |
|---|---|---|
|  | QWNGKNSEMTVKQFGGGNGAAVDQTASNSSVNV TQVGFGNNATAHQY*GGSGSSGSGGSGGGSGSSGSG GSGGGSGSSGSGGSG*MISSLRSALSACFALLLVLAFG VASAQAKTVEVKLGTDAGMLAFEPSSVTISTGDSV KFVNNKLAPHNAVFEGHEELSHPDLAFAPGESWQE TFTEAGTYDYYCEPHRGAGMVGKVVV*NGSGGSGG SGGSGHHHHHH* (SEQ ID NO: 79) |  |
| Mitochondrial ferritin fusion | <u>MKLLKVAAIAAIVFSGSALAG</u>VVPQYGGGGNHGG GGNNSGPNSELNIYQYGGGNSALALQTDARNSDLT ITQHGGGNGADVGQGSDDSSIDLTQRGFGNSATLD QWNGKNSEMTVKQFGGGNGAAVDQTASNSSVNV TQVGFGNNATAHQY*GGSGSSGSGGSGGGSGSSGSG GSGGGSGSSGSGGSG*MLSGFWFFSKHIGPALMSLPR VLHRCTVPQCLASRYPLLPASPRRLLASVASSQGSD GTARVRHNFHPDSEAAINHQINMELYASYVYLSMA YYFSRDDVALYNFSKSFLRQSLEEREHAEKLMKLQ NQRGGRICLQDIKKPEQDDWESGLRAMECALLLEK SVNQSLLDLHTLASEKGDPHLCDFLETHYLNEQVK SIKELGDHVHNLVTMGAPAVGLAEYLFDKHTLGSE SKH*GSGGSGGSGGSGHHHHHH* (SEQ ID NO: 80) | 45821 |
| Rubredoxin fusion | <u>MKLLKVAAIAAIVFSGSALAG</u>VVPQYGGGGNHGG GGNNSGPNSELNIYQYGGGNSALALQTDARNSDLT ITQHGGGNGADVGQGSDDSSIDLTQRGFGNSATLD QWNGKNSEMTVKQFGGGNGAAVDQTASNSSVNV TQVGFGNNATAHQY*GGSGSSGSGGSGGGSGSSGSG GSGGGSGSSGSGGSG*MAKWVCKICGYIYDEDAGDP DNGISPGTKFEELPDDWVCPICGAPKSEFEKLED*GS GGSGGSGGSGHHHHHH* (SEQ ID NO: 81) | 25190 |

In an alternative embodiment, the mutant may lack the Sec peptide (underlined sequence). In an alternative embodiment, the mutant may lack the His tag.

Example VII

Curli-Producing Biofilm Formation

For fibers containing only natural amino acids, biofilms producing curli can be grown on agar plates, or in liquid medium. Transformed PQN4 cells are streaked onto Luria-Bertani (LB) agar plates containing 100ug/mL carbenicillin and 0.5% glucose (to prevent activation of the T7 promoter). Colonies are picked from the plates and 5 mL cultures are inoculated (in LB containing and 100ug/mL carbenicillin). Cultures are grown overnight at 37° C. The overnight cultures are diluted 100 times in fresh LB medium with 100ug/mL carbenicillin and 2% glucose, and grown at 37° C. until they reach an optical density (OD) at 600 nm of 0.6 to 0.8. Cells are pelleted at 4000×g, and gently resuspended in an induction medium (LB without glucose, containing 0.4 mM IPTG and 100 ug/mL carbenicillin). Protein expression is allowed to occur at 30° C. overnight.

For fibers containing non-natural amino acids, biofilm formation in solution follows the same procedure as for fibers containing only natural amino acids, except that no glucose is used at any step, and carbenicillin is replaced by a combination of two antibiotics selected specifically for each vector used. Carbenicillin or ampicillin is used for pBbB8a, and kanamycin is used for pBbB8k plasmids, in combination with the appropriate selection marker for pKB-pylHRS (kanamycin) or pEVOL (spectinomycin) plasmids. In addition, at the point of induction, the non-natural amino acid of interest is added to the culture medium at a final concentration ranging between 1 mM and 10 mM.

Example VIII

Assessment and Quantification of Curli Fiber Production

Two types of Congo red assays were performed. 1) Agar plates containing LB, Congo red, coomassie blue and carbenicilling, with or without IPTG, were prepared. 5 to 10 ul of biofilm-forming cultures were spotted onto the plates at an $OD_{600\ nm}$ of 0.6 to 0.8 and incubated for one to two days. The incubation was done at room temperature for plates with IPTG (induced expression), and at 37° C. for plates without IPTG. 2) Congo red spin-down assay were performed to quantify the relative expression levels of the mutants. 1 mL of cultures that were induced with IPTG or simply grown overnight were centrifuged at 4000×g for 10 minutes and resuspended gently in phosphate buffer. 100 ul of a Congo red solution at 0.015% was added to each suspension and incubated 5 minutes. The suspensions were then centrifuged at maximum speed to 10 minutes. 100 ul of the supernatant was transferred to a 96-well plate and the absorption at 490 nm was recorded. This reading corresponds to Congo red molecules that are not bound to the biofilm. As controls, wild-type cultures were included in the experiment, as well as bacteria producing no CsgA but a maltose-binding protein instead.

To quantitatively detect the presence of CsgA, an adapted whole-cell ELISA was also performed. The same cultures used for Congo assays were diluted to an OD 600 nm of 0.3 in Tris-buffered saline (TBS), and filtered on a 96-well filter plate (as described in Nguyen et al., Nature Communications, 2014). The filtered cultures were successively incubated with a blocking solution, an anti-his antibody and a secondary antibody, with several wash steps in between each incubation. Finally, an ELISA substrate was added to each well and incubated 5 min. 100 ul of this reaction mixture was transferred to a 96-well plate and the absorbance at 450 and 650 nm was recorded.

Example IX

Purification of Curli Fibers Via His-Tag Affinity Purification

Curli fibers can be separated from bacteria using cell lysis and his-tag affinity purification, or using constructs without CsgB proteins to secrete CsgA directly in the culture medium and collecting the produced CsgA using Ni NTA beads. 1) For purification with cell lysis: After expression, cells are harvested by centrifugation at 4000×g for 20 minutes and resuspended in a lysis buffer containing 7M guanidine chloride. A protease inhibitor is added, and the suspension is stored at −20° C. overnight. The suspension is thawed on ice, and sonicated to lyse the cells completely (40% amp, 3×25s ON, 35 OFF). The cell debris is pelleted at 10000×g for 30 minutes. 4 mL of Ni NTA beads are added to the supernatant, along with 10 mM imidazole, and the mixture is incubated with agitation at room temperature for 2 hours. The beads are added to a column, and rinsed three times with phosphate buffer to remove residual imidazole. The column is then washed five times with one column volume with phosphate buffer containing 40 mM imidazole. CsgA is then eluted with phosphate buffer containing 500 mM imidazole. 2) For purification of secreted CsgA: Ni NTA beads are added directly to the culture medium at the time of induction. After overnight expression, the beads are allowed to settle down in a conical flask, and then separated from the supernatant and bacteria by pipetting the bottom layer. As described before, the beads are added to a column, from which CsgA can be eluted.

Example X

Characterization Via Electron Microscopy

Scanning electron microscopy (SEM) samples are prepared by filtering biofilms in suspension onto Nucleopore filters (0.22 um pore size, GE Healthcare Bio-Sciences) under vacuum. The filters are then washed with 0.1M sodium cacodylate buffer, and fixed with 2% glutaraldehyde and 2% paraformaldehyde for 2h at room temperature. They are then washed with water, and an increasing ethanol step gradient, before drying in a critical point dryer and sputtering with 5 nm of Pt/Pd.

Example XI

CsgA Proteins Engineered to Allow for Electron Transfer

Figure 5B:
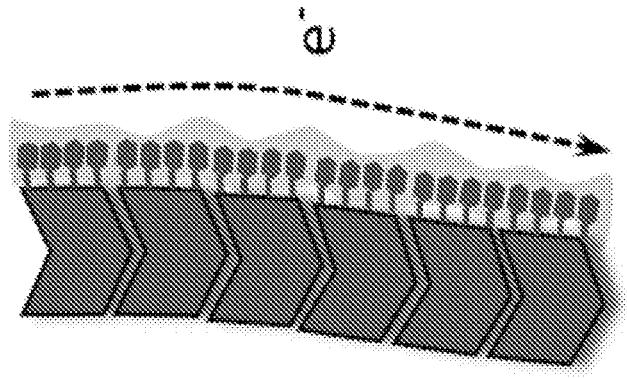
FIGS. 5A, 5B, 5C, and 5D schematically depict a biomimetic approach for the synthesis of conductive curli nanofibers.
Figure 5A:
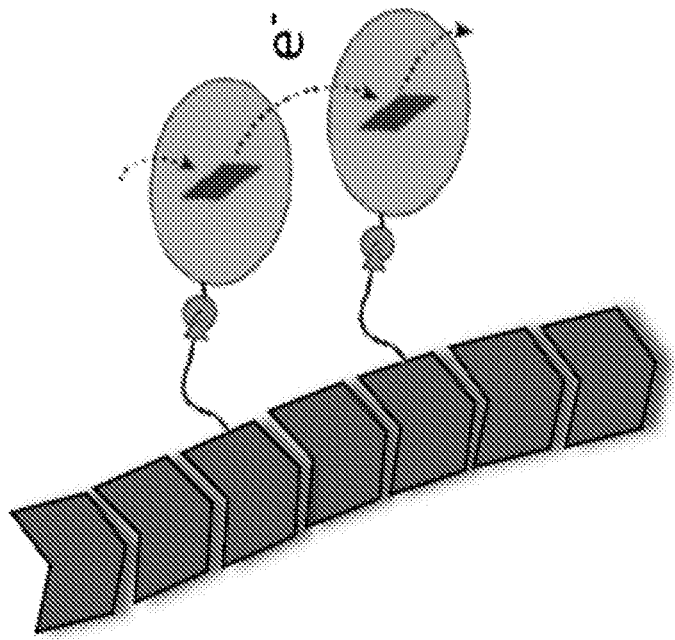

FIG. 5A shows small peptide domains containing metal centers fused to CsgA (e.g., via SpyCatcher-SpyTag binding), thereby forming a close-packed network of conductive peptides allowing for electron hopping.

FIG. 5B shows CsgA mutants wherein aromatic rings form a π-π stacking network along the fibers, which induces interchain electron delocalization.

Figure 5D:
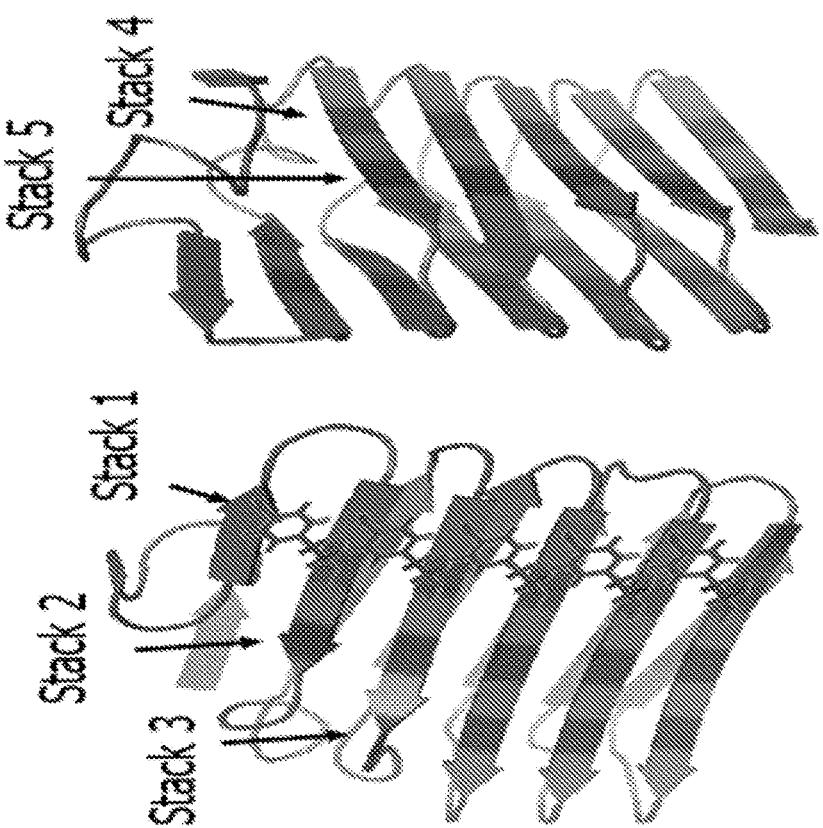
Figure 5C:
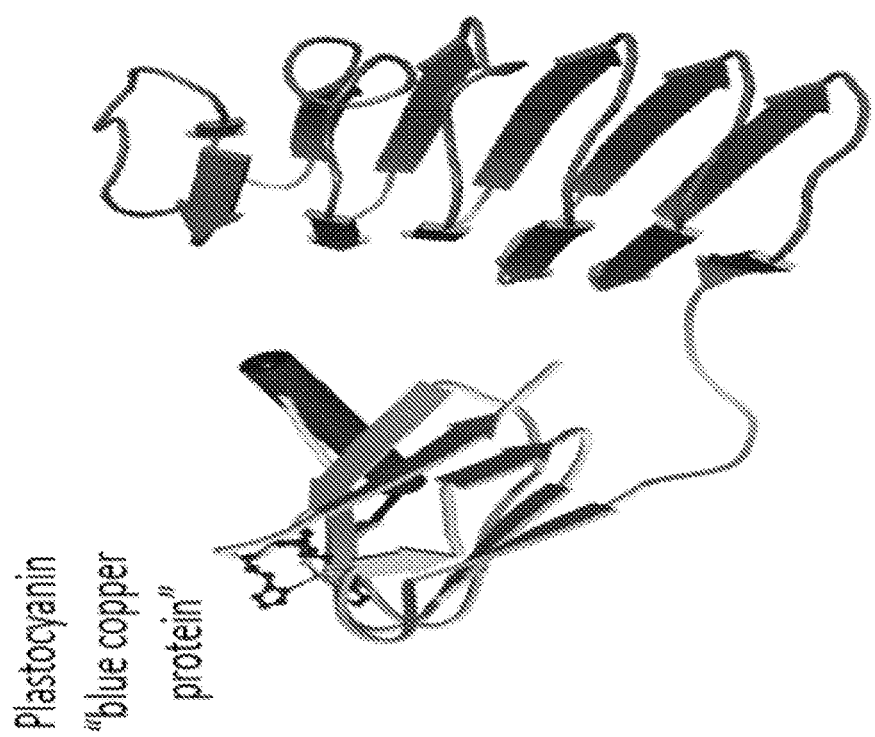

FIG. 5C depicts an example of a fusion protein of CsgA with a small protein or domain containing a metal center, in this case, CsgA fused to plastocyanin.

FIG. 5D depicts the series or stacks of aligned amino acid residues in the five pseudo-repeats of the CsgA β-helix structure that have been identified and mutated to aromatic amino acids. The aromatic residues are expected to interact and form π-stacks, leading to electron delocalization and optical phenomena.

Example XII

CsgA Fusions and Mutants are Expressed and Form Curli Nanofibers

Figure 6B:

As depicted in FIG. 6A, an amyloid-specific dye, Congo Red, binds to curli nanofibers produced by bacteria having CsgA mutations and CsgA fusions (CsgA-plastocyanin and CsgA-rubredoxin), indicating the formation of curli nanofibers. FIG. 6B illustrates that biofilm formation was observed with all CsgA-fusions and mutants.

Example XIII

CsgA Fusions and Mutants are Expressed and Form Curli Nanofibers

As depicted in FIG. 7, electron microscopy reveals the presence of mutant curli fibers with morphology similar to wild-type curli fibers.

Figure 8:
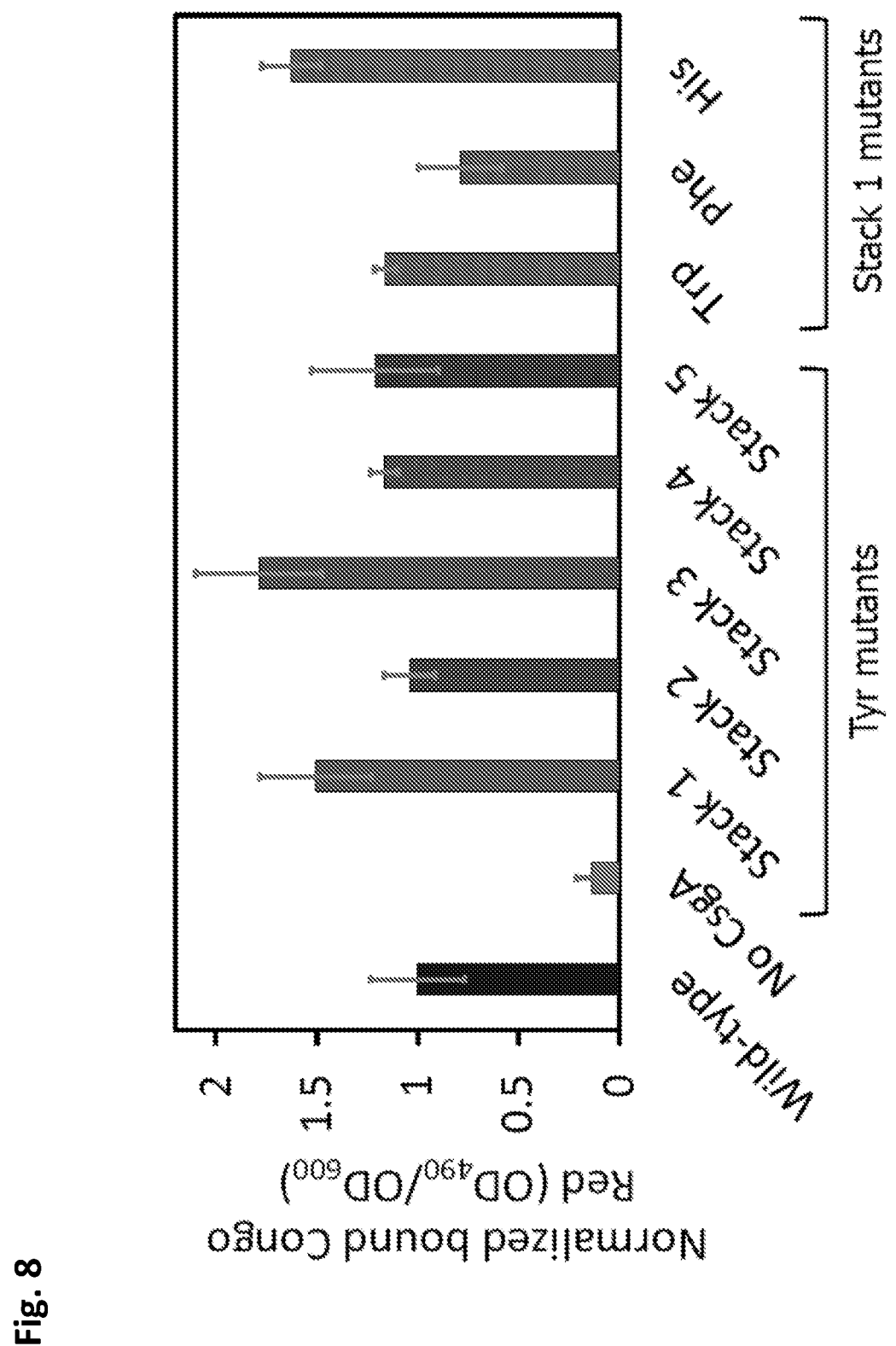
FIG. 8 depicts the amounts of curli fibers produced by mutant and control bacteria, as quantitated by a Congo Red binding assay.

Congo Red, a dye that binds specifically to amyloid fibers, was also used to detect the formation of curli fibers. As shown in FIG. 8, all biofilms with aromatic amino acid mutations express curli fibers significantly more than control biofilms without plasmid encoding CsgA.

Figure 9:
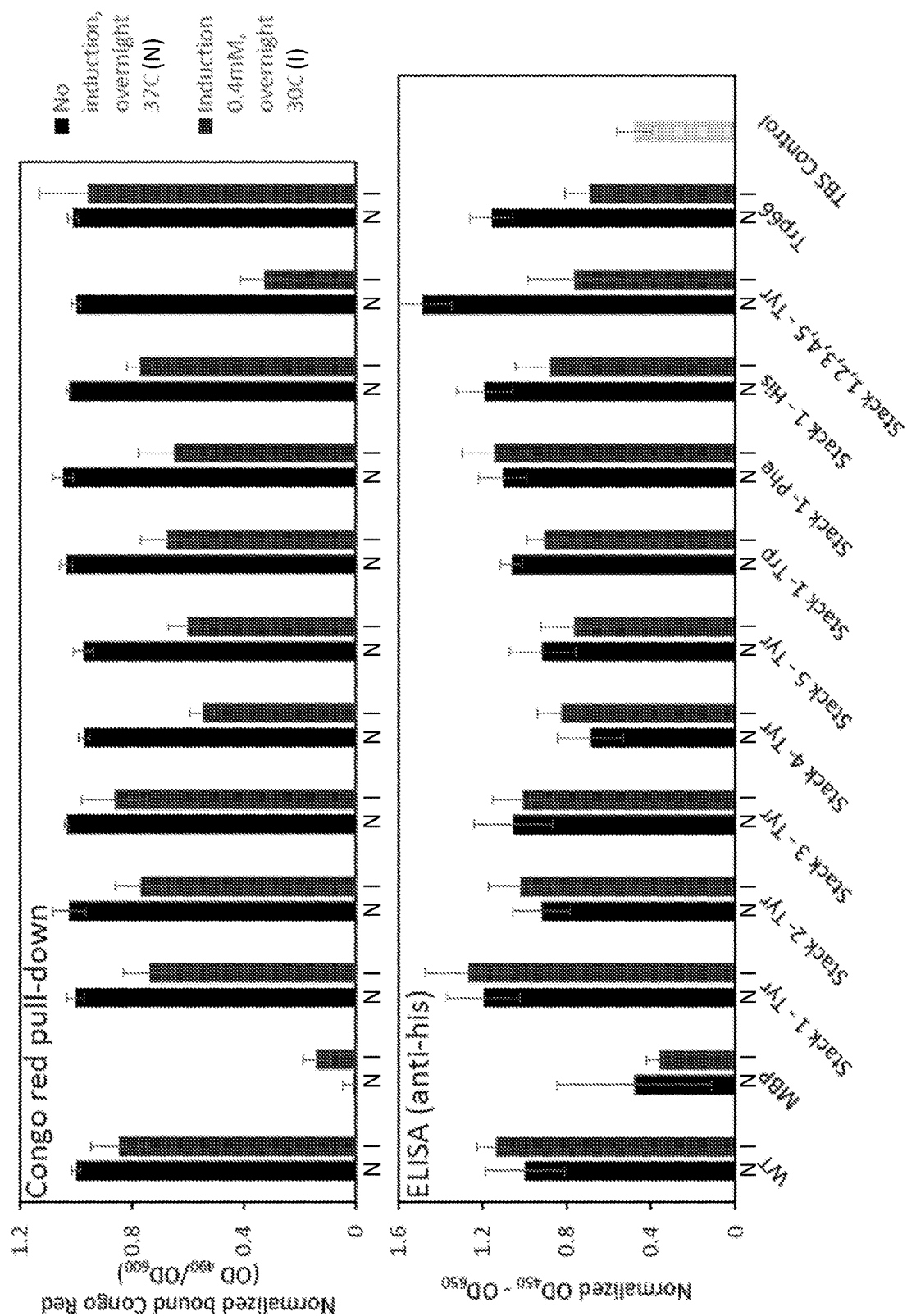
FIG. 9 depicts the amounts of curli fibers produced by mutant bacteria that express CsgA under the control of an inducible promoter.

FIG. 9 shows that all bacteria with aromatic amino acid mutations produce curli nanofibers, whether or not a CsgA inducible promoter was induced, based on a Congo Red pull-down assay and ELISA using an anti-his antibody. Expression levels vary with or without induction.

Figure 10:
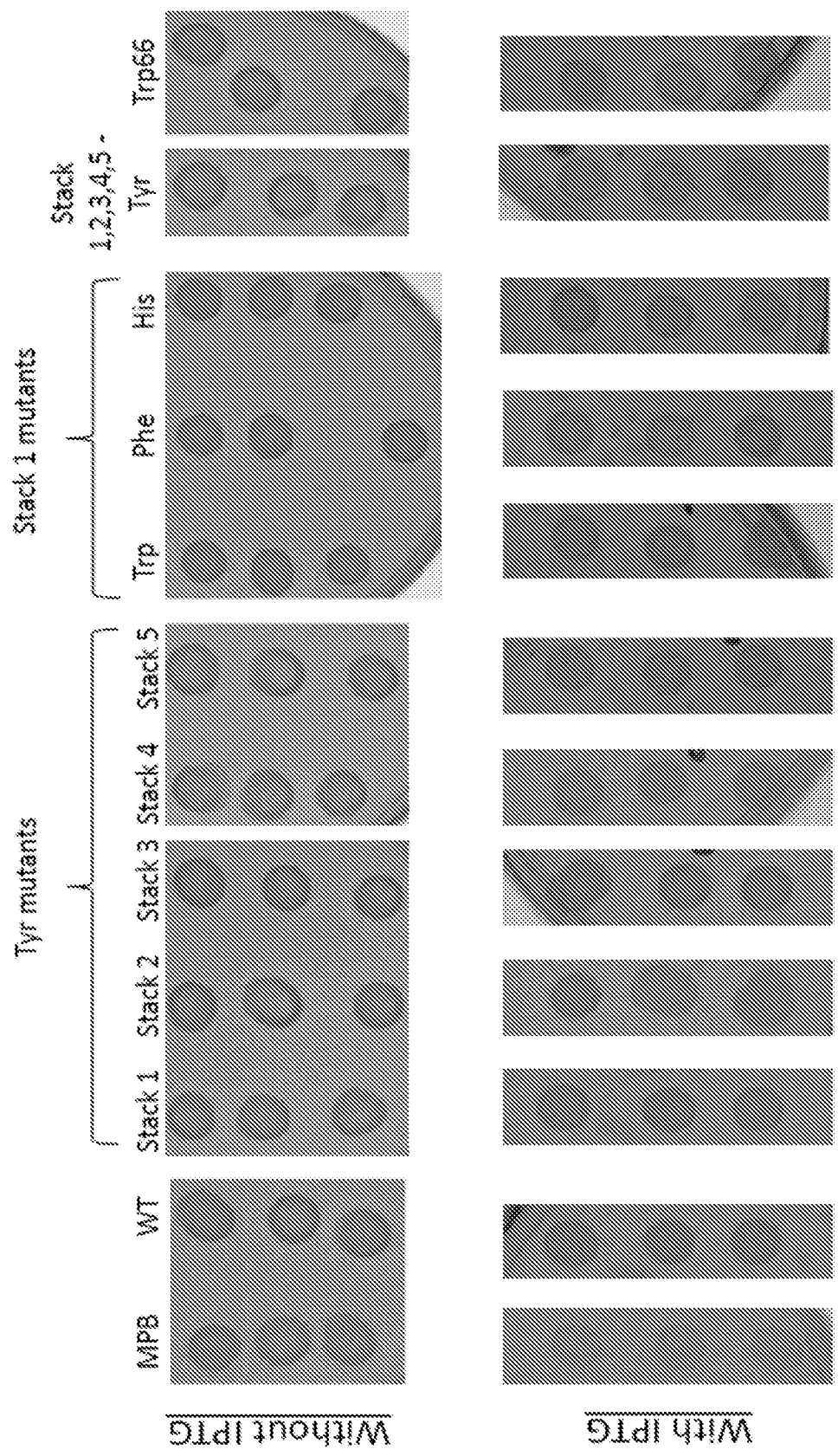
FIG. 10 depicts a Congo Red spot test showing curli fiber formation by mutant and control bacteria.

Similarly, as depicted in FIG. 10, a Congo Red spot test shows that mutant and control bacteria produce curli fibers. Curli fibers were produced, whether or not CsgA was under the control of an IPTG-inducible promoter, and the promoter was induced.

Example XVI

Mutant Curli Fibers Exhibit Increased Fluorescence

Figure 11:
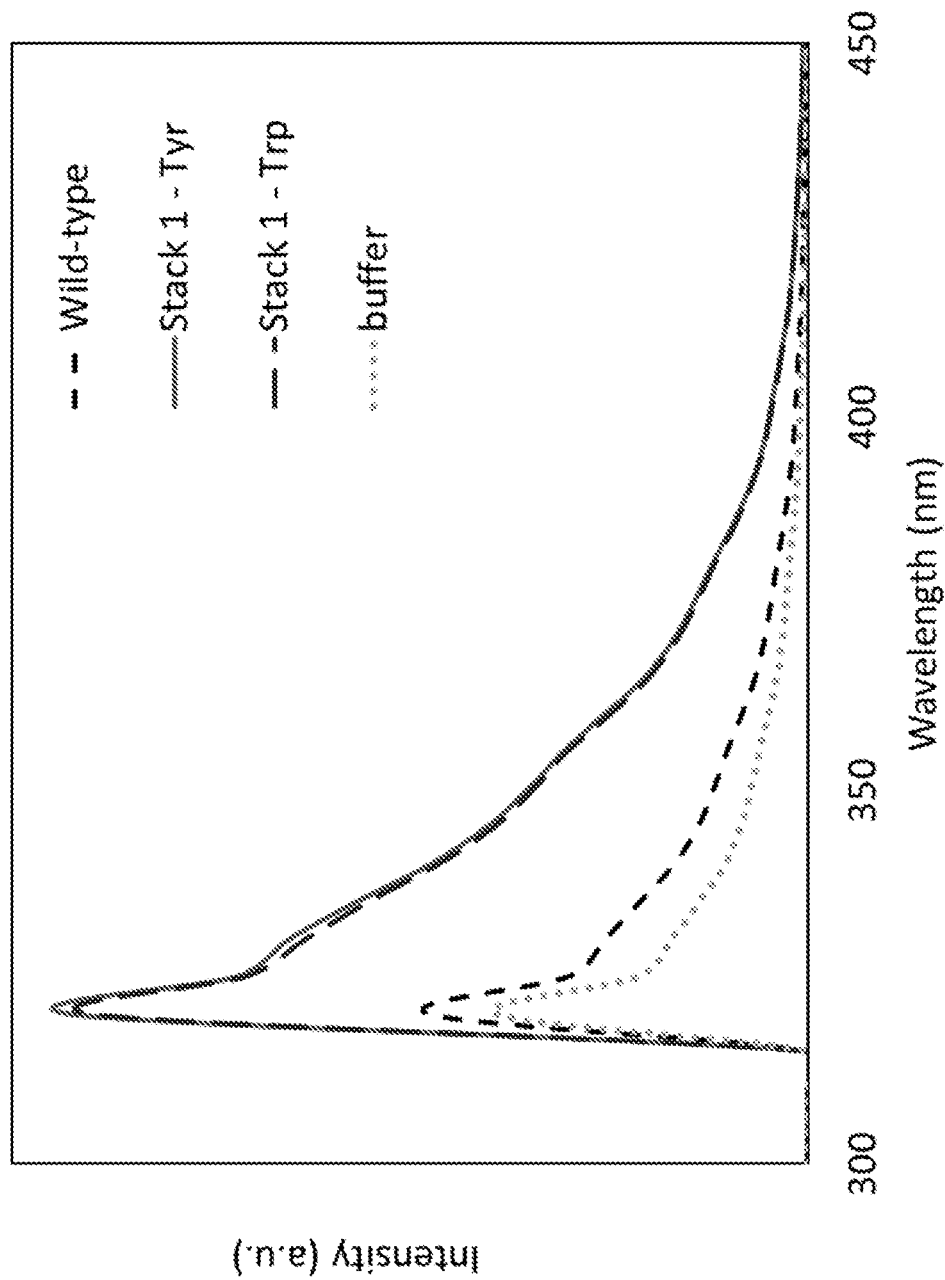
FIG. 11 depicts the fluorescence intensity of wild-type and mutant curli fibers.

As depicted in FIG. 11, curli fibers composed of CsgA mutants, e.g., stack 1 tyrosine or tryptophan mutants, exhbit increase fluorescence relative to wild-type control curli fibers.

Example XV

Mutant Curli Fibers Isolated from Bacteria

Figure 12:
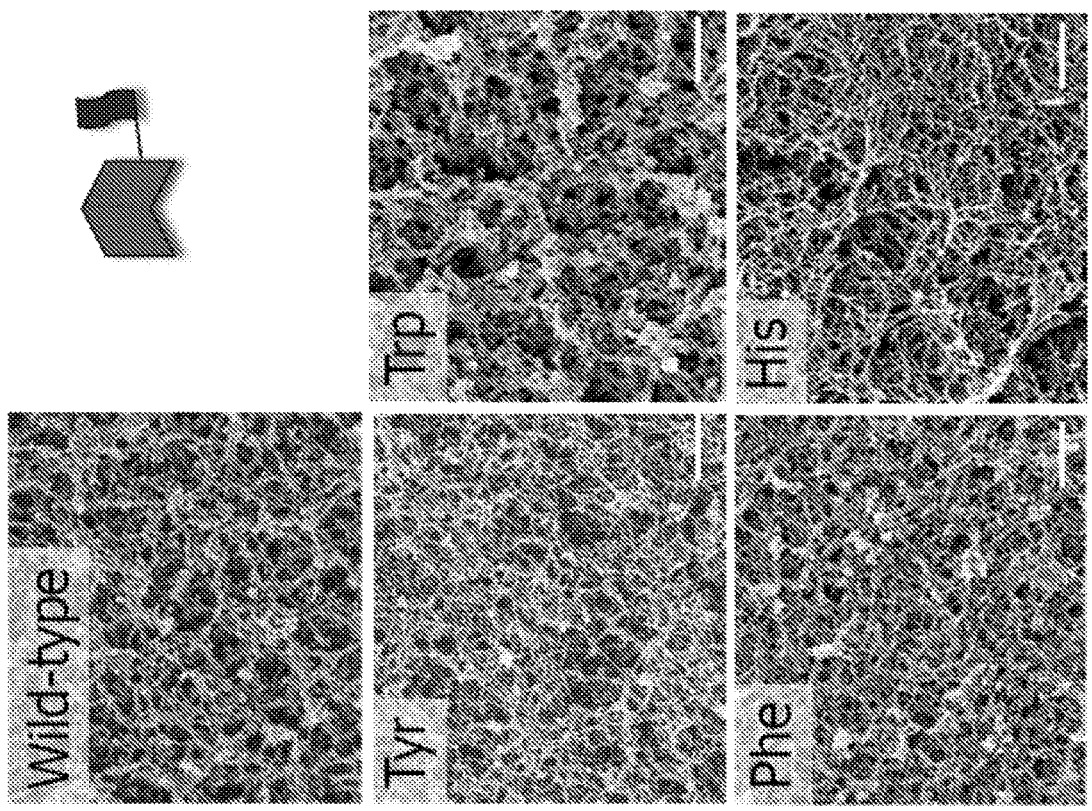
FIG. 12 shows electron microscopy of mutant and control curli fibers that have been isolated and purified.

His-tagged CsgA monomers and fibers were isolated using an affinity column, as described herein. About 1-2 mg of proteins was purified per 500 ml of culture. Isolated CsgA monomers spontaneously re-assemble into fibers in buffer. Electron microscopy was used to assess morphology of isolate, purified mutant curli fibers relative to a wild-type control. As shown in FIG. 12, purified mutant fibers exhibit slightly different aggregation behavior relative to wild-type control.

SDS-Page and Western blots using anti-His antibody were used to determine the impurity levels remaining after the purification process. FIG. 13 shows that some impurities remain after purification of mutant and control curli fibers.

Example XVI

Figure 14A:
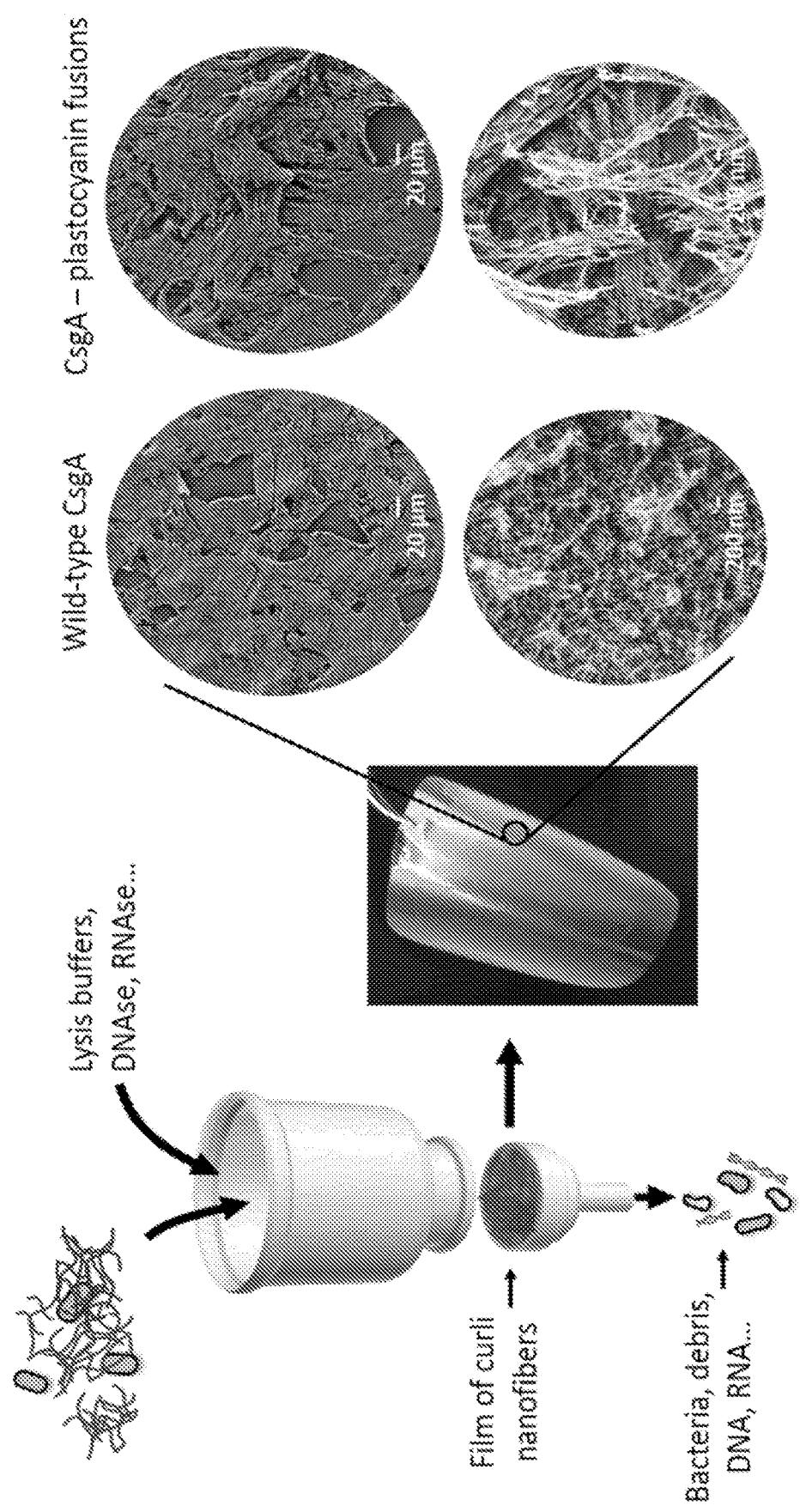

Purification of Curli Nanofiber Thin Films and Measurement of Electrical Properties As depicted in FIG. 14A, filtration purification was used to purify wild-type and mutant curli nanofiber thin films, and curli nanofiber films made from CsgA fusions, including CsgA-plastocyanin fusion. The electrical properties of these thin films were then measured. As shown in FIG. 14B, silver interdigitated electrodes were drawn directly onto dried curli films deposited on filter membranes. Resistance and current-voltage curves were then measured to determine which of the protein films were conductive. Purified films made using CsgA fusions to rubredoxin, plastocyanin, and mitochondrial ferritin were tested, as were purified films made using CsgA mutants, e.g., tyrosine stack mutants and tryptophan stack mutants.

Example XVII

Figure 15A:
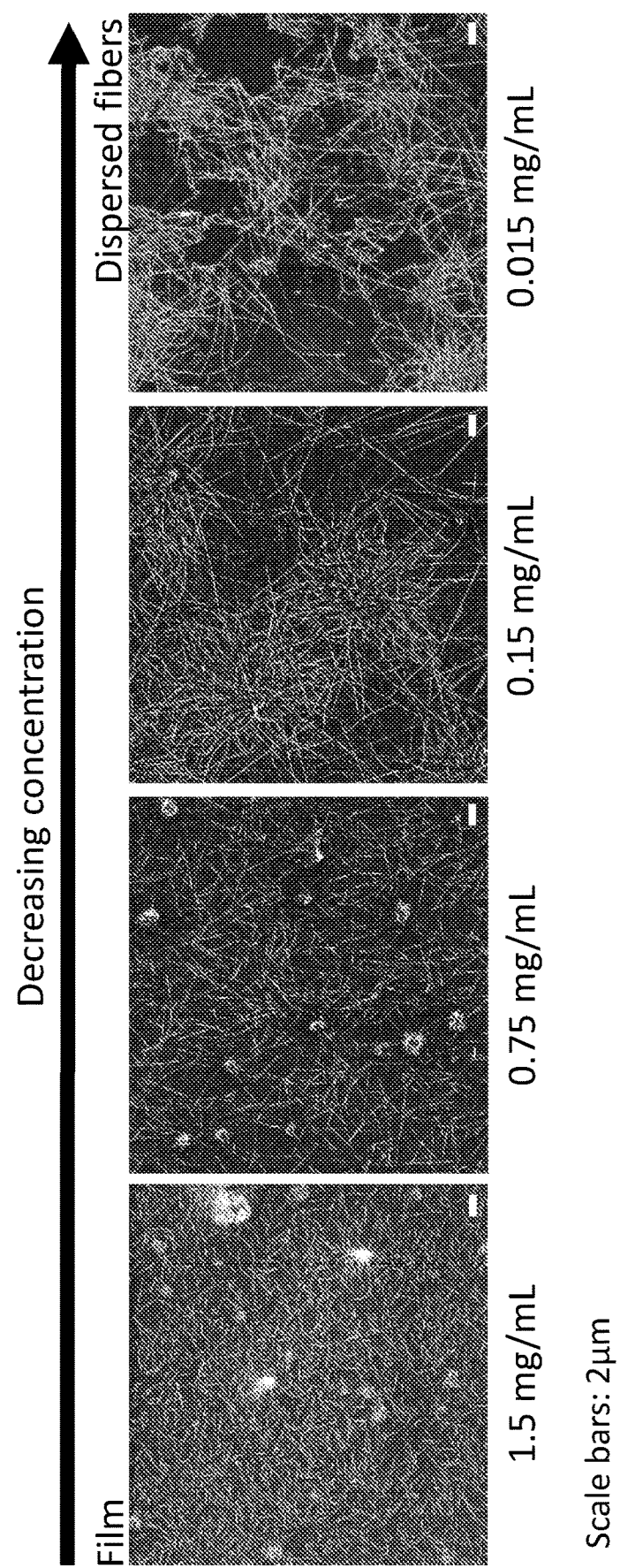
FIGS. 15A and 15B depict dropcast films of curli fibers, or single curli fibers on substrates and electrodes.
Figure 15B:
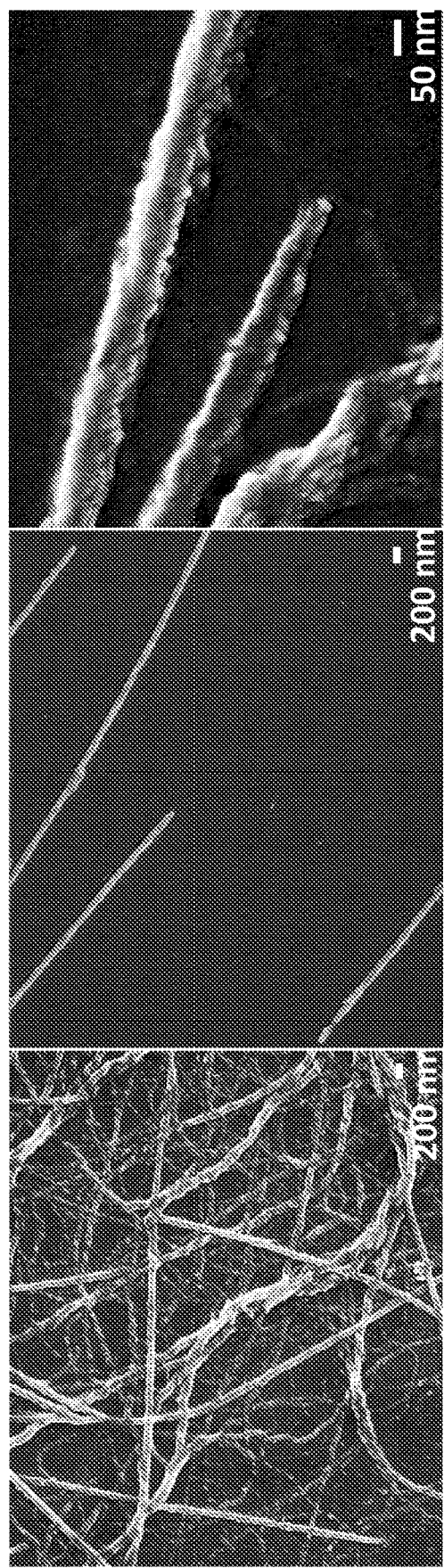
Figure 16B:
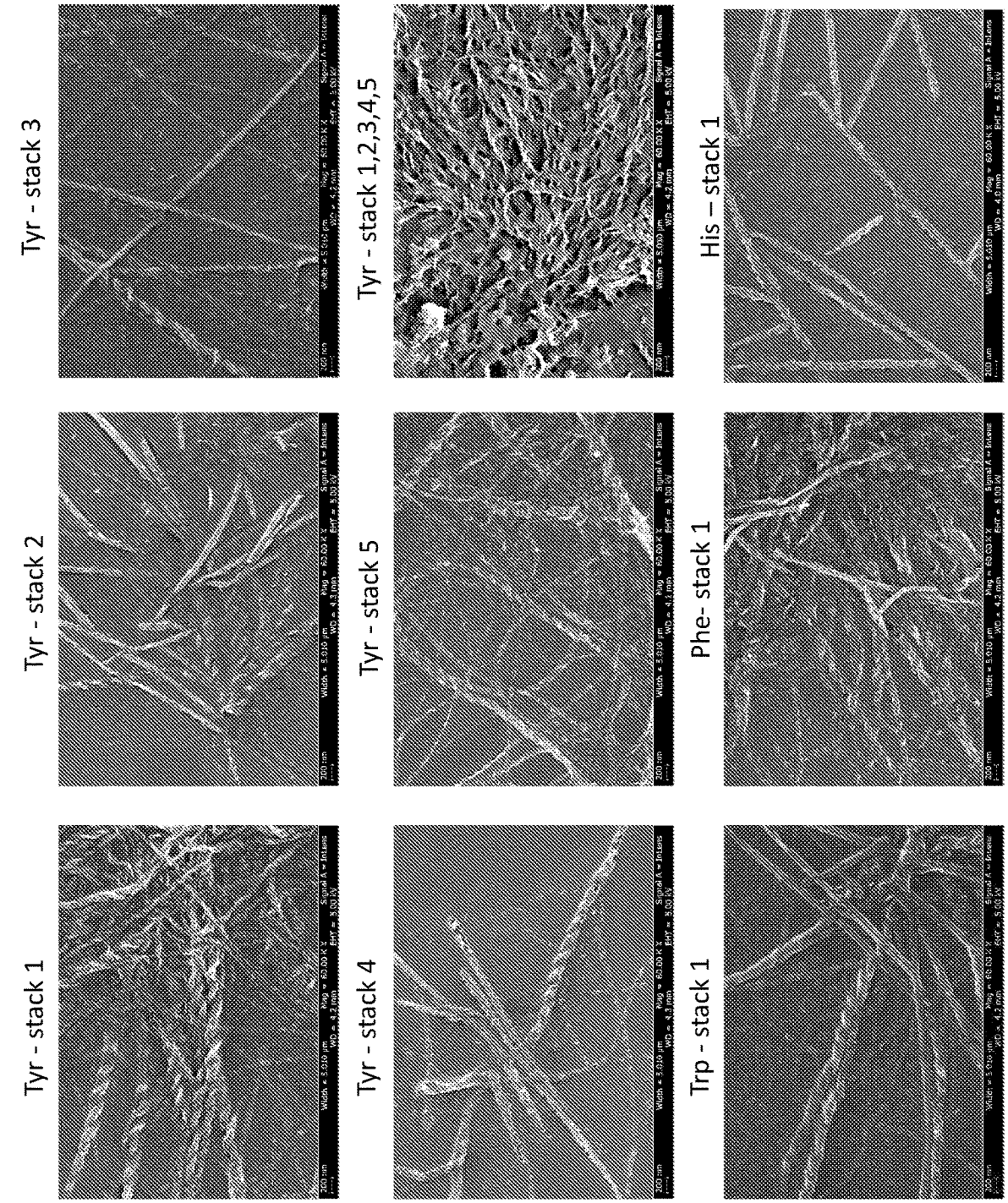
Figure 17A:
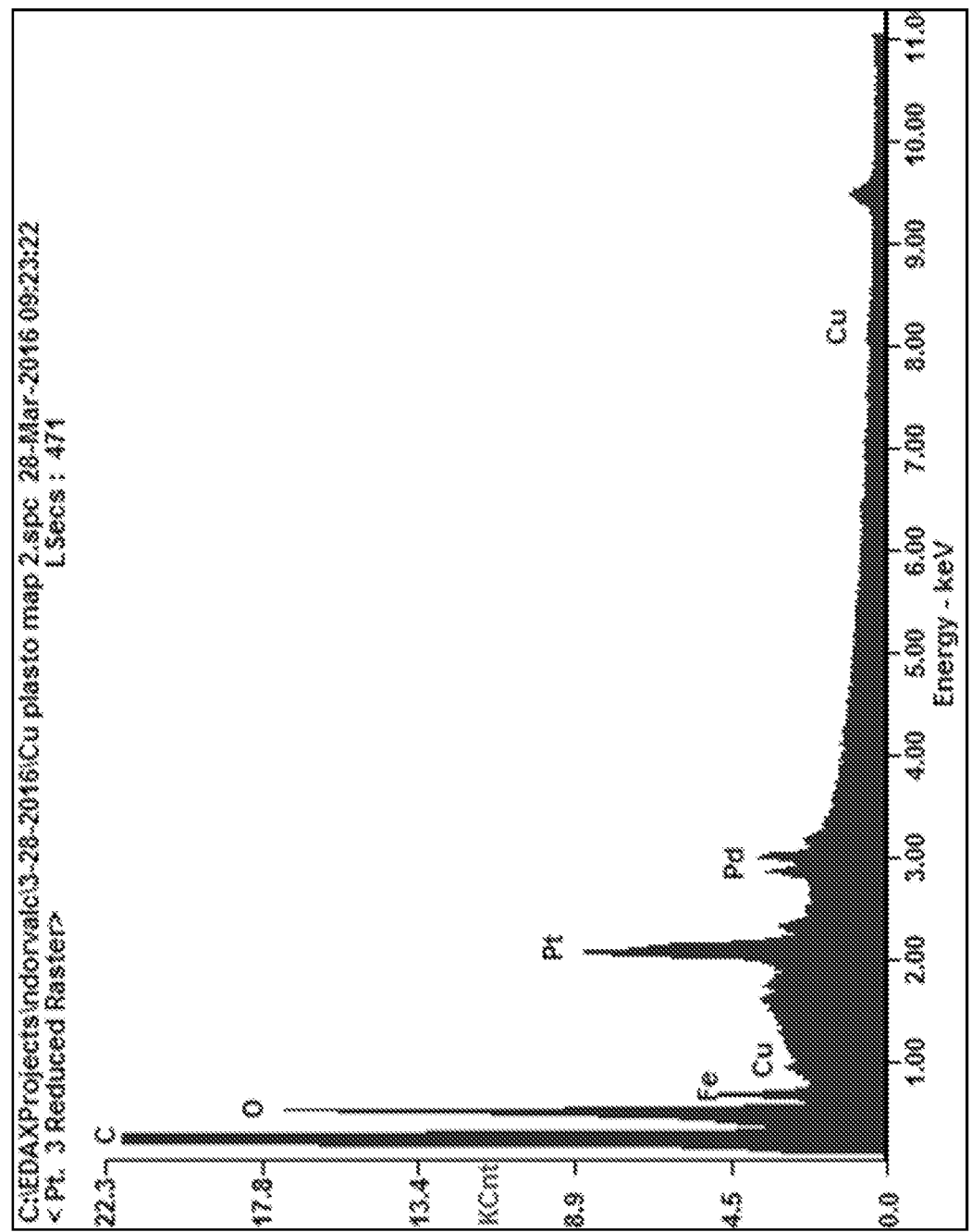
FIGS. 17A-17C depict curli fibers comprising CsgA fused to a 36 amino acid linker and -plastocyanin and 10 mM copper nitrate on 10 μm polycarbonate membrane. Energy-dispersive X-ray spectroscopy (EDX) of CsgA-plastocyanin fusions showing the presence of copper in the samples. EDX was used to perform elemental mapping on fibers, after filtration purification on polycarbonate filter membranes. Copper was detected at a weight percent of 0.49 for CsgA-plastocyanin fusions. Samples were coated with 5 nm of Pt/Pd prior to imaging. Fe signal is detected mainly in the pores of the filter membrane and comes from the SEM holder.
Figure 17B:
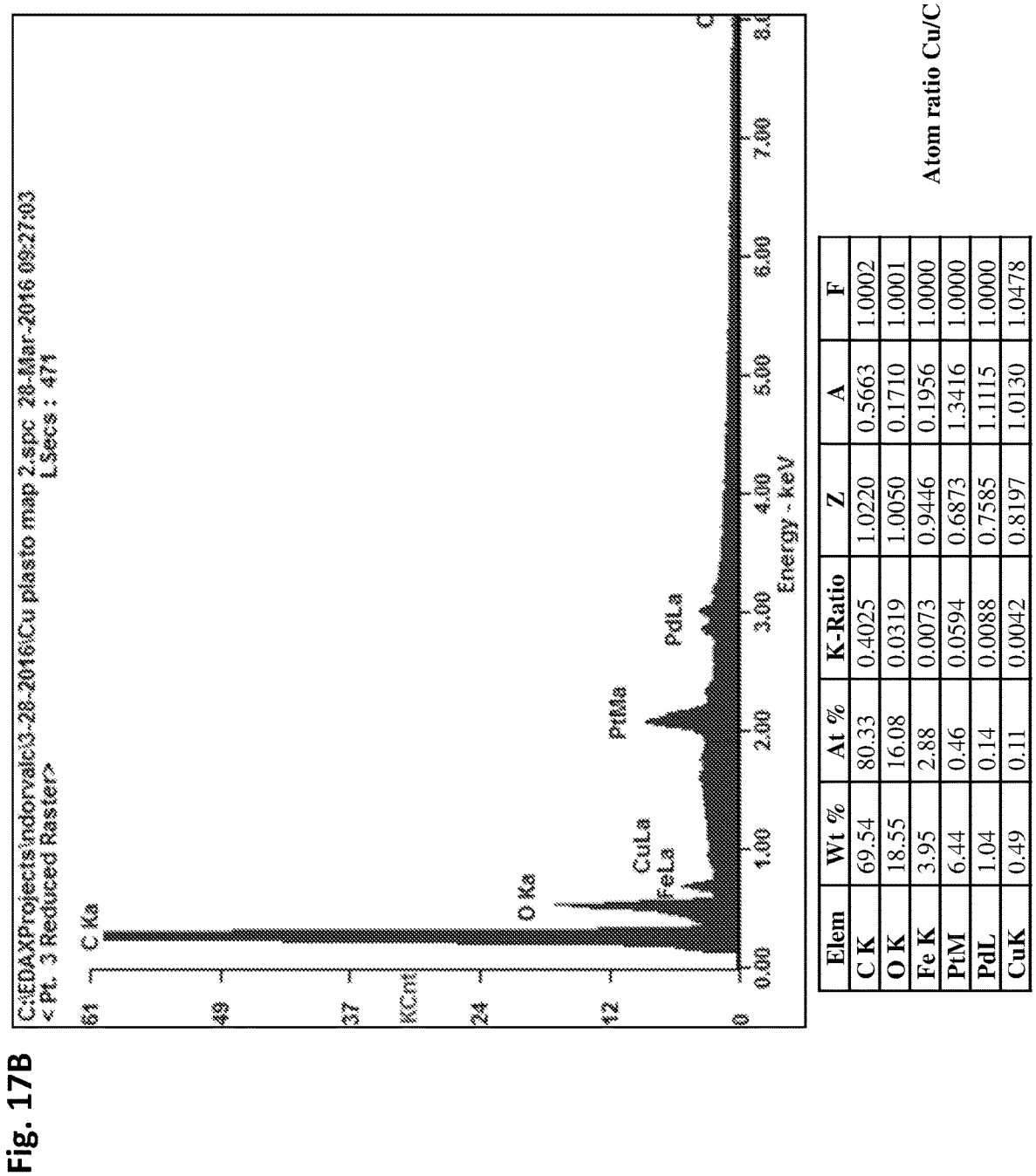
Figure 17C:
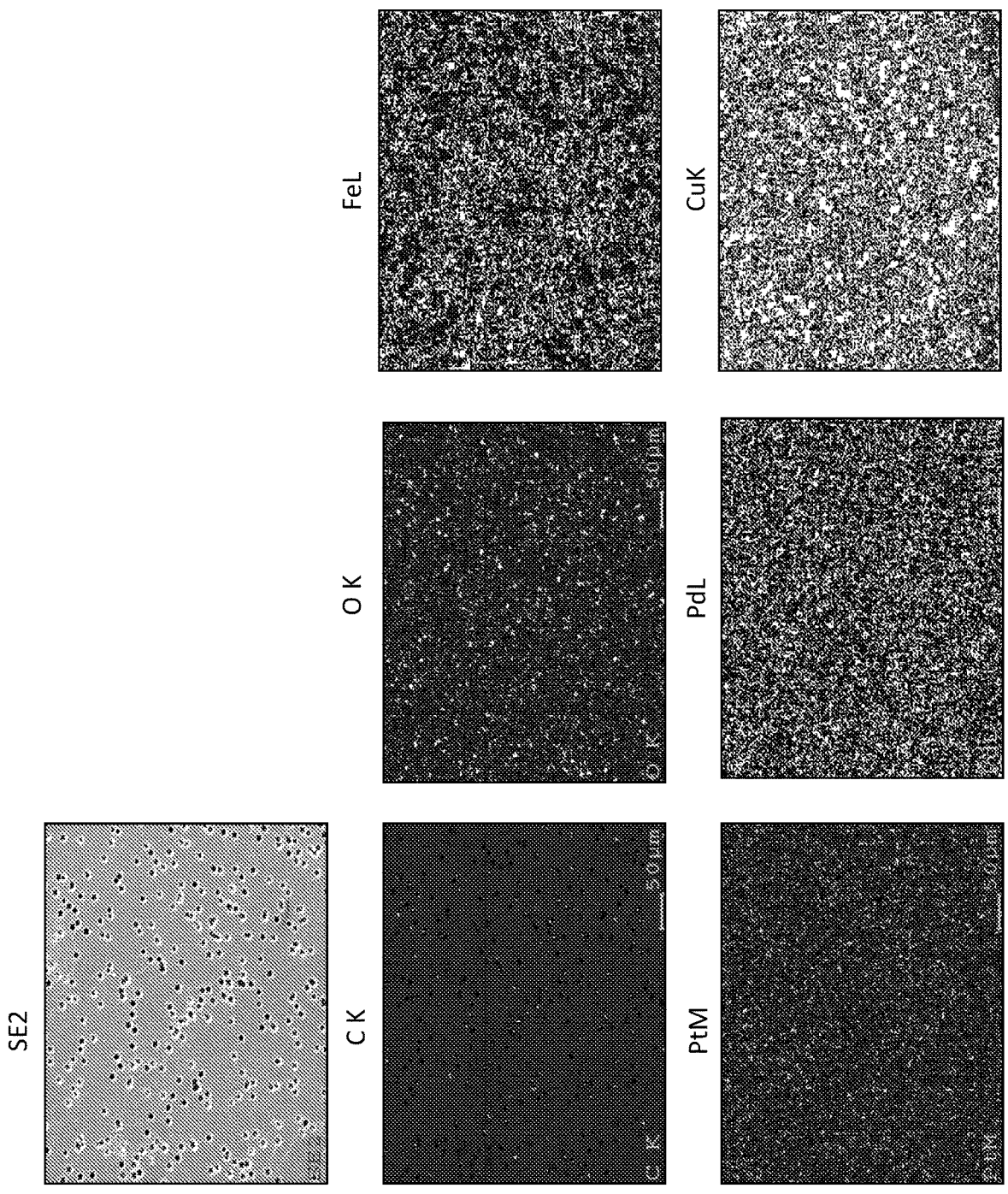
Figure 18A:
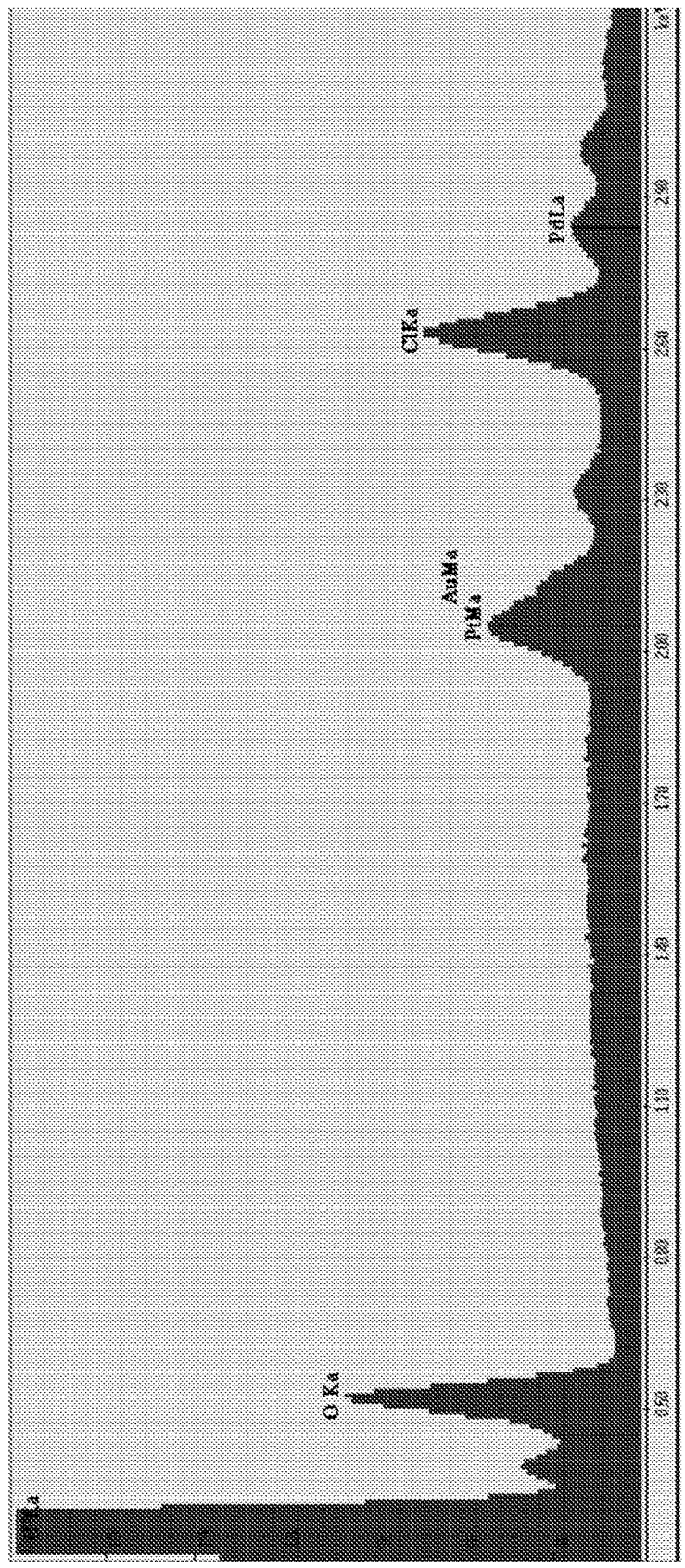
FIGS. 18A and 18B depict wild-type curli fiber plus NiNTA on 10 μm polycarbonate membrane. EDX of wild-type curli fibers with a His-tag that were purified via filtration, and incubated with NiNTA-Au nanoparticles. Copper was not detected in this sample, but gold (from the nanoparticles) was detected. Samples were coated with 5 nm of Pt/Pd prior to imaging. Residual salts from rinses with guanidine hydrochloride during filtration purification can explain the Cl signal.
Figure 18B:
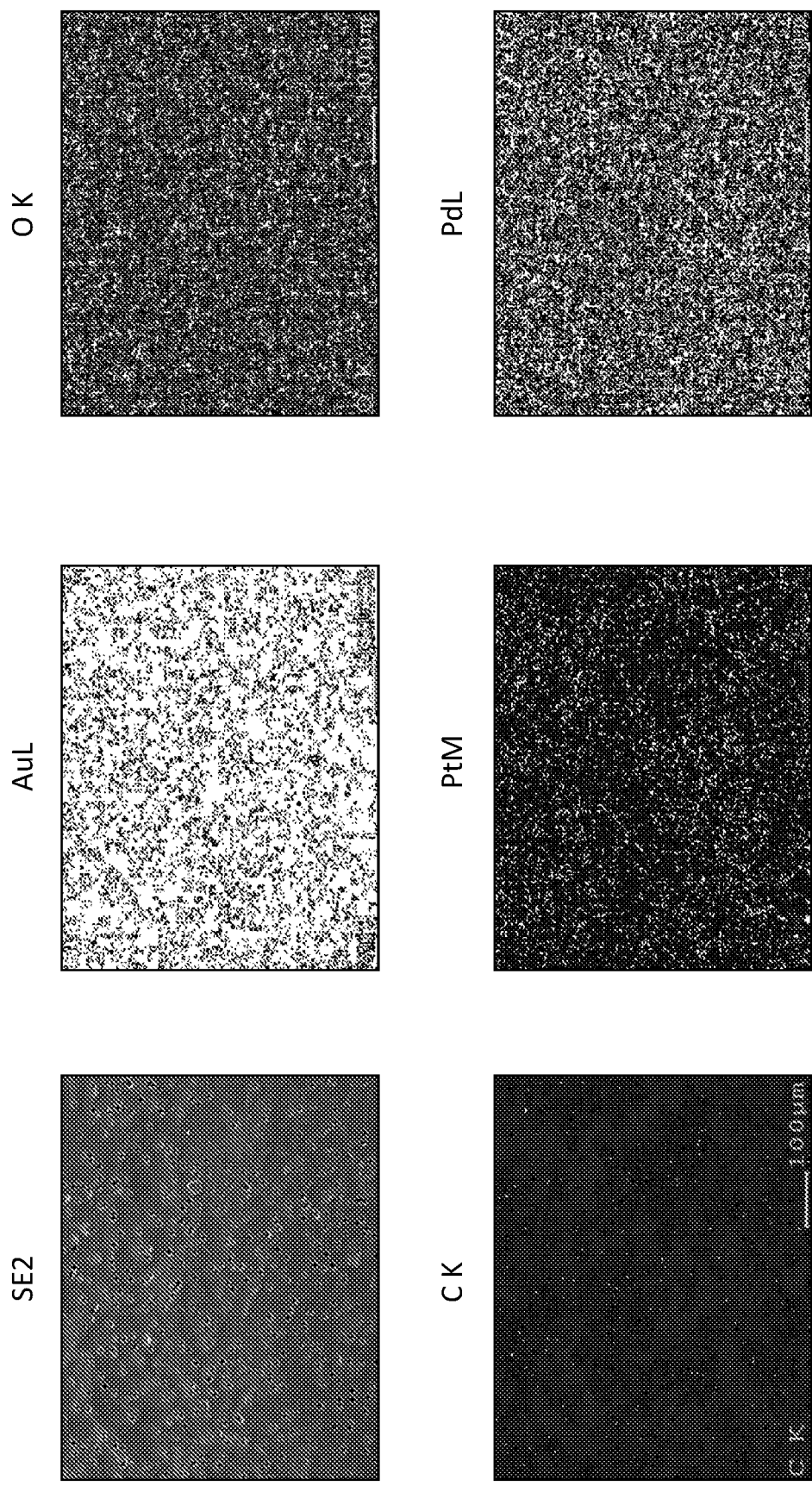

Dropcasting of Curli Fiber Comprising Mutant CsgA or CsgA Fused to a Redox Active Domain to Form Thin Films on Substrates and Electrodes To demonstrate that curli fibers comprising mutant CsgA or CsgA fused to a redox active domain may be used to form thin films, curli fibers comprising wild-type CsgA or curli fibers comprising mutant CsgA or CsgA fused to a redox active domain were dropcast from a 1:1 HFIP:TFA solution onto substrates to form thin films. After dropcasting, samples were rinsed with DI water and dried in air. The morphology of some amyloid fibers has been studied and described previously (see, e.g., Jordens et al. (2011) *Biomacromolecules* 12(1): 187-93; Abraham et al. (2015) European Polymer Journal 65: 268-275; Adamcik et al. (2016) *Angew. Chem. Int. Ed.* 55: 618-22; Assenza et al. (2014) *Phys. Rev. Lett.* 113: 268103; Usov and Mezzenga (2014) *ACS Nano* 8 (11): 11035-41; and Zhong et al. (2014) Nature Nanotechnology 9: 858-866; the entire contents of each of which are incorporated herein by reference). As shown in FIG. 15A, thin films formed by dropcasting curli fibers comprising wild-type CsgA onto plasma-treated silicon wafers at decreasing concentrations led to the formation of thin films and dispersed curli fibers. For high concentrations (0.75 mg/mL and above), fibrous thin films were obtained. For lower concentrations, dispersed fiber aggregates, and dispersed single fibers were obtained. High magnification scanning electron microscopy (SEM) images of individual curli fibers are shown in FIG. 15B. Curli fibers comprising CsgA fused to either ferritin domain, plastocyanin or rubredoxin, or curli fibers comprising mutant CsgA were also dropcast onto silicon substrate to form thin films as described above, and characterized using SEM. As shown in FIGS. 16A and 16B, thin films were successfully formed using both types of curli fibers. The films were also further deposited on glass and stained with Congo Red to confirm the presence of amyloid fibers.

Example XVIII

Figure 19A:
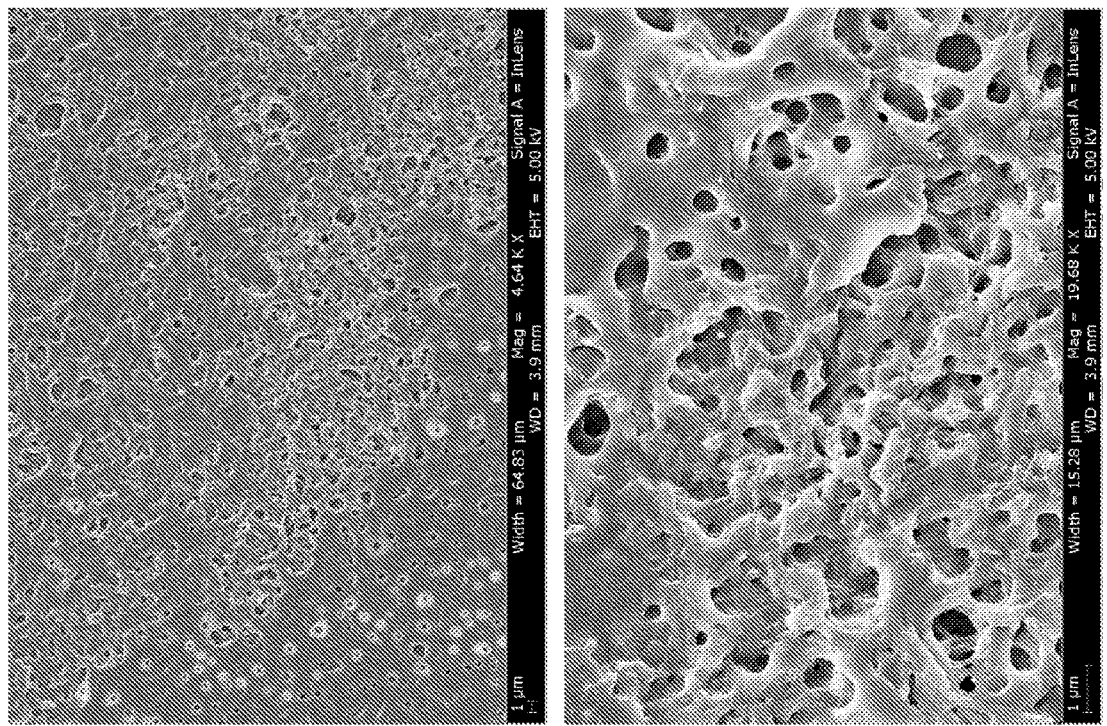
FIGS. 19A and 19B depict SEM images of dropcast films formed using curli fibers comprising CsgA fused to plastocyanin overlayed on commercial Micrux interdigitated electrodes. Samples were coated with 5 nm of Pt/Pd prior to imaging.
Figure 19B:
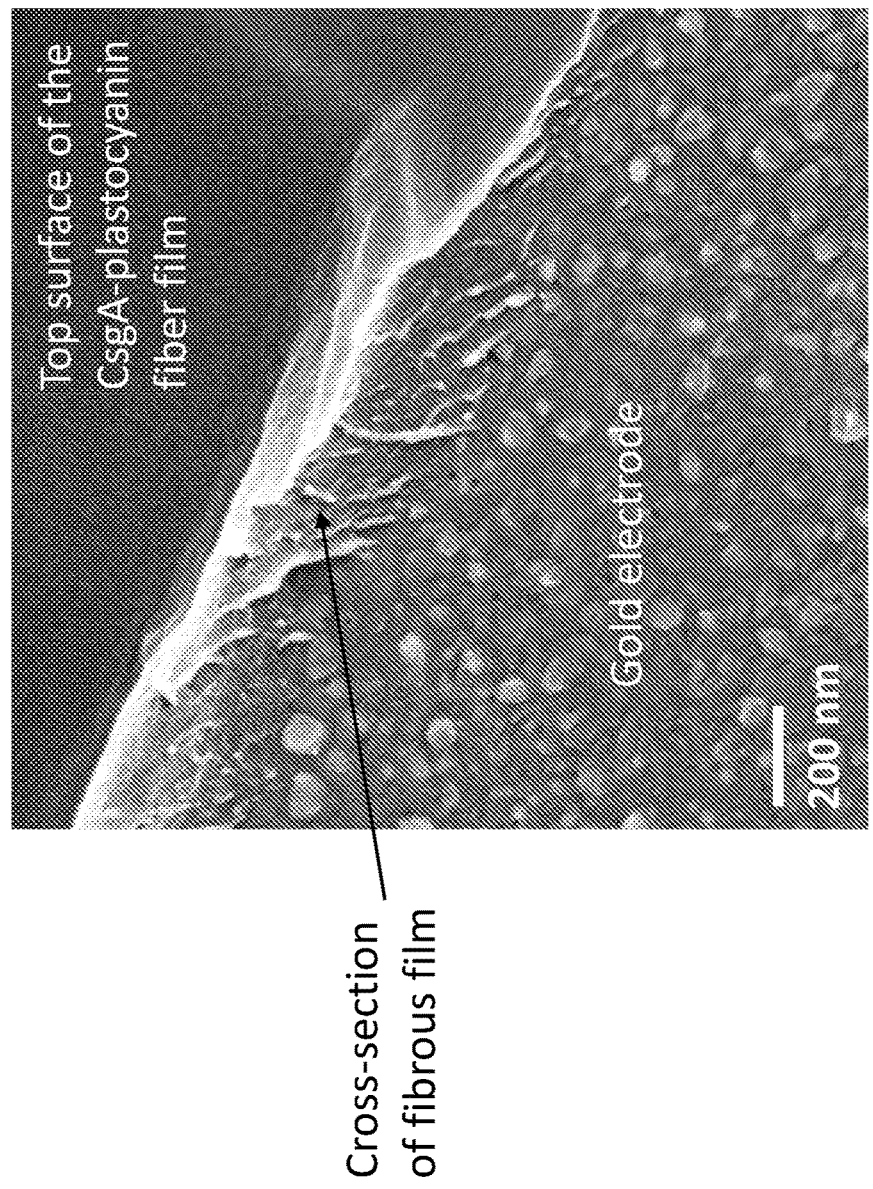
Figure 21A:
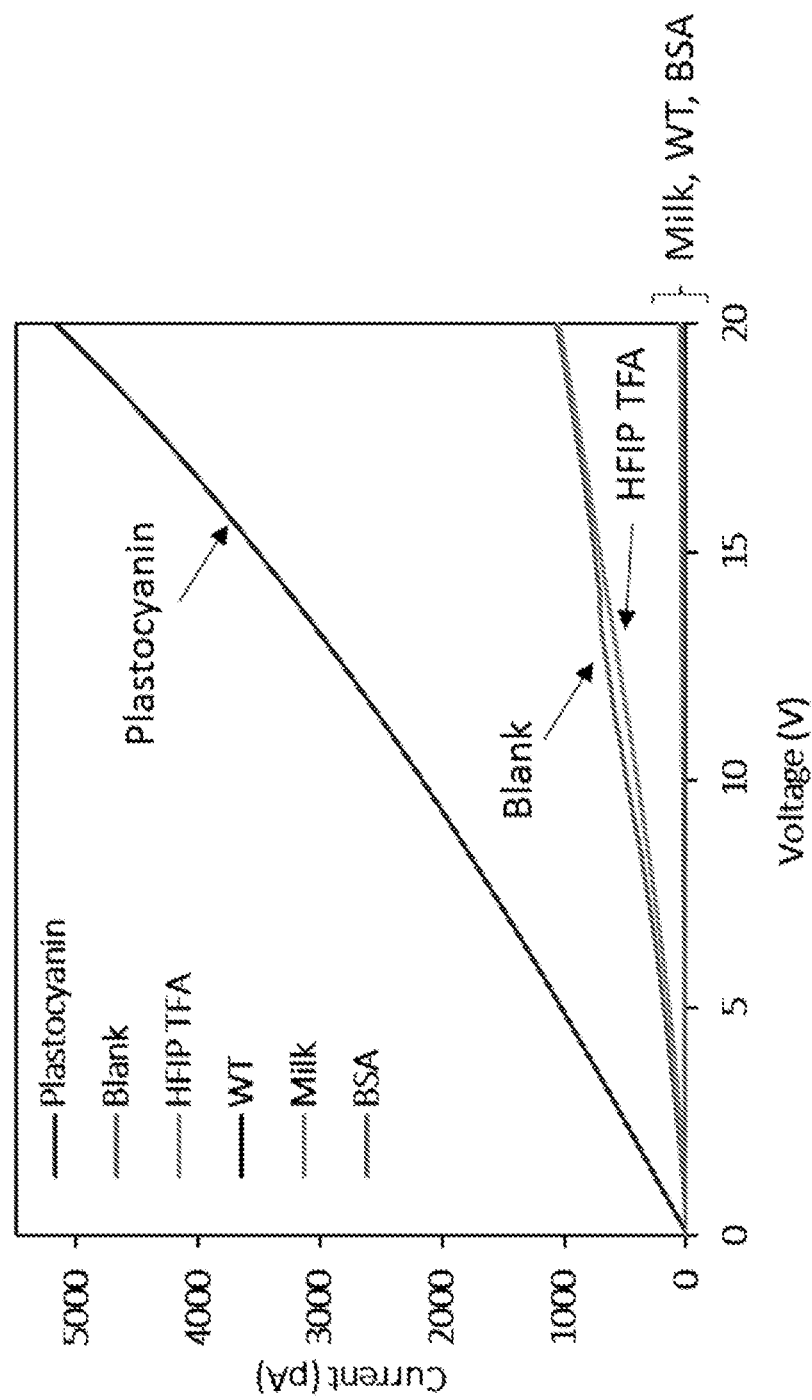
FIGS. 21A and 21B depict current-voltage curves for curli fibers comprising CsgA-fused to plastocyanin relative to wild-type curli fibers and control proteins. Protein fibers and control proteins at 5 mg/mL in 1:1 HFIP:TFA mixture were dropcast on commercial Micrux interdigitated electrodes with 10 μm spacing. Prior to dropcasting, electrodes were cleaned with isopropanol and were plasma-treated. After drying of the fiber solution, electrodes were rinsed with deionized water and dried in air. A probe station was used to measure current-voltage curves.
Figure 21B:
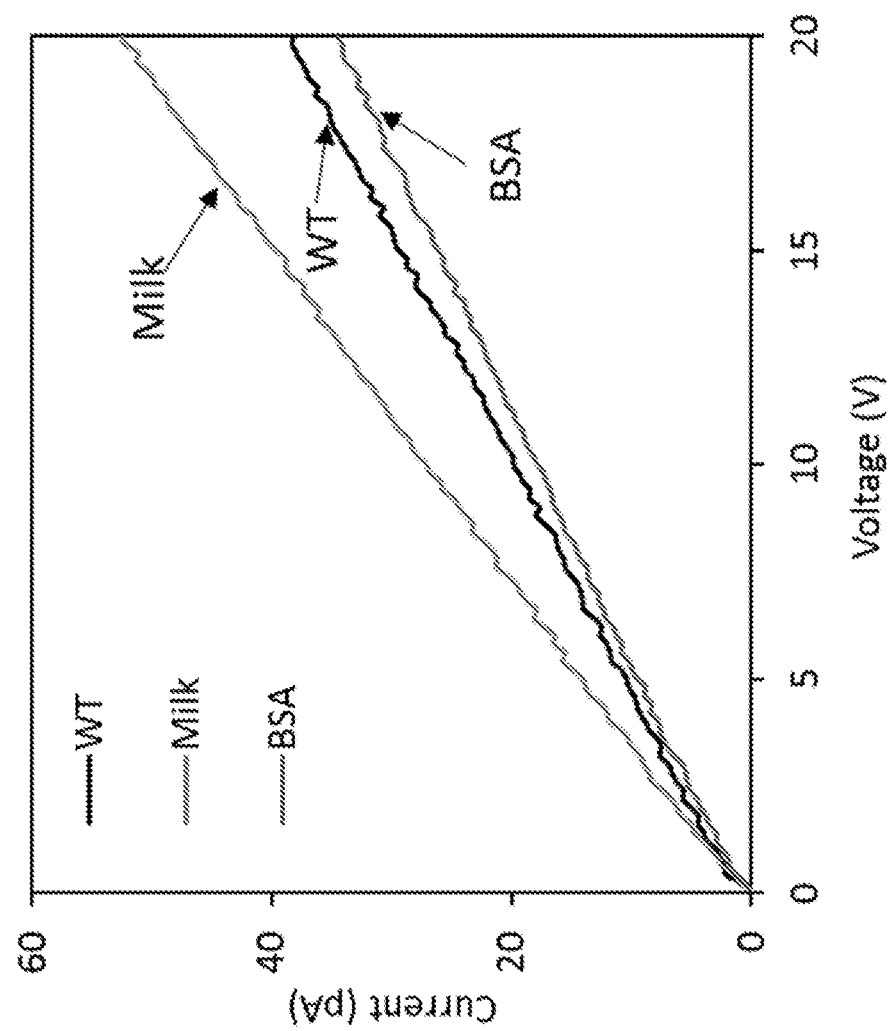

Measurement of Electrical Properties of Thin Films Formed by Dropcasting of Curli Fiber Comprising Mutant CsgA or CsgA Fused to a Redox Active Domain To characterize the electric conductivity of thin films of curli fibers comprising mutant CsgA or CsgA fused to a redox active domain were formed by dropcasting the disassembled curli fibers from a 1:1 HFIP:TFA solution onto electrodes, and allowing them to reassemble by as the solvent evaporates. Thin films formed using curli fibers comprising CsgA fused to plastocyanin were overlayed onto commercial Micrux interdigitated electrodes. Samples were coated with 5 nm of Pt/Pd prior to SEM imaging. As shown in FIG. 19A, film formed by protein fibers was continuous, and revealed some porosity and nano structured fibrous morphology. Moreover, as shown in FIG. 19B, SEM images of the interface between the film and the electrode showed a fibrous cross-section and good contact between the fibers and the gold electrode. The surface morphology of the thin films formed on interdigitated electrodes was further characterized using SEM with samples that were not coated with Pt/Pd prior to imaging. As shown in FIGS. 20A and 20B, thin films formed using curli fibers comprising CsgA fused to plastocyanin formed thick films that fully covered the electrode.

Figure 22B:
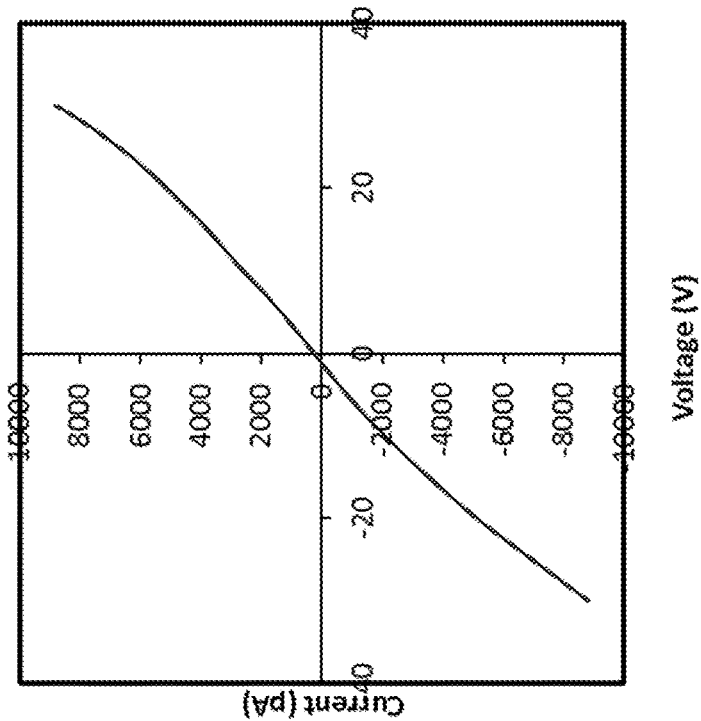
FIGS. 22A-22C depict additional current-voltage curves for curli fibers comprising CsgA fused to plastocyanin.
Figure 22A:
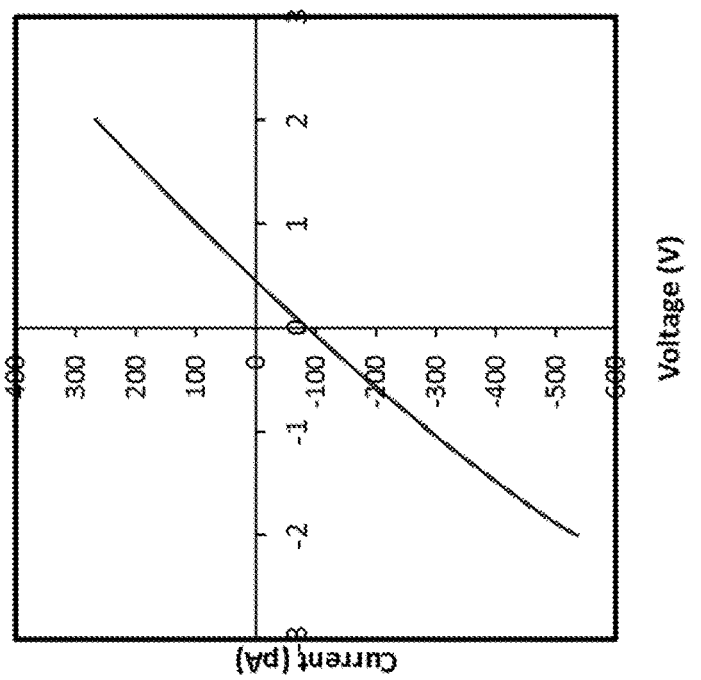
Figure 22C:
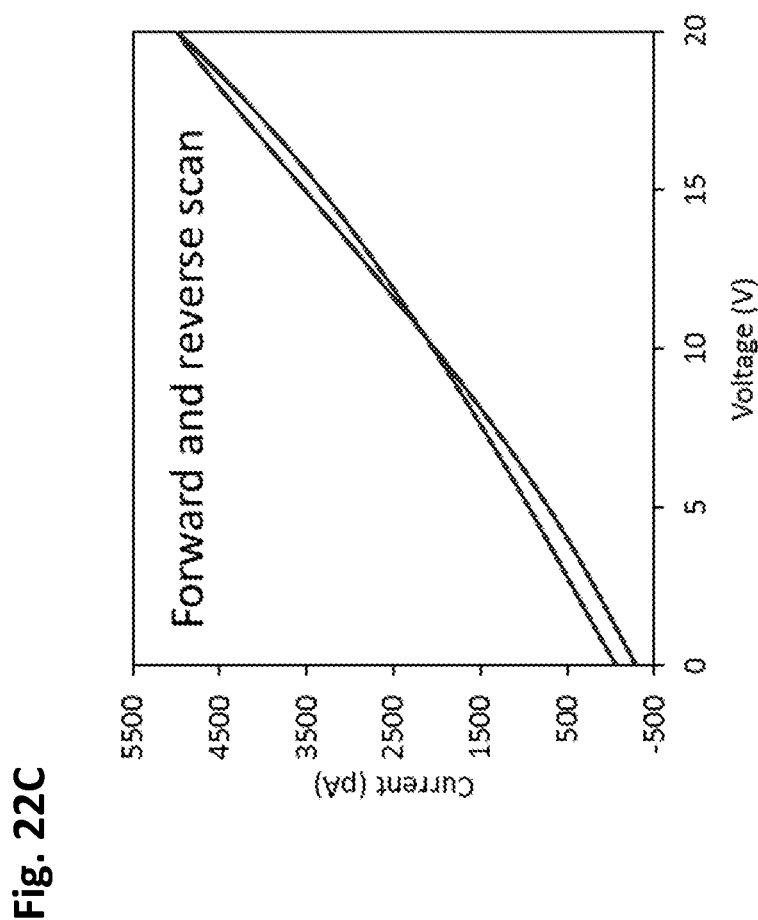
Figure 23:
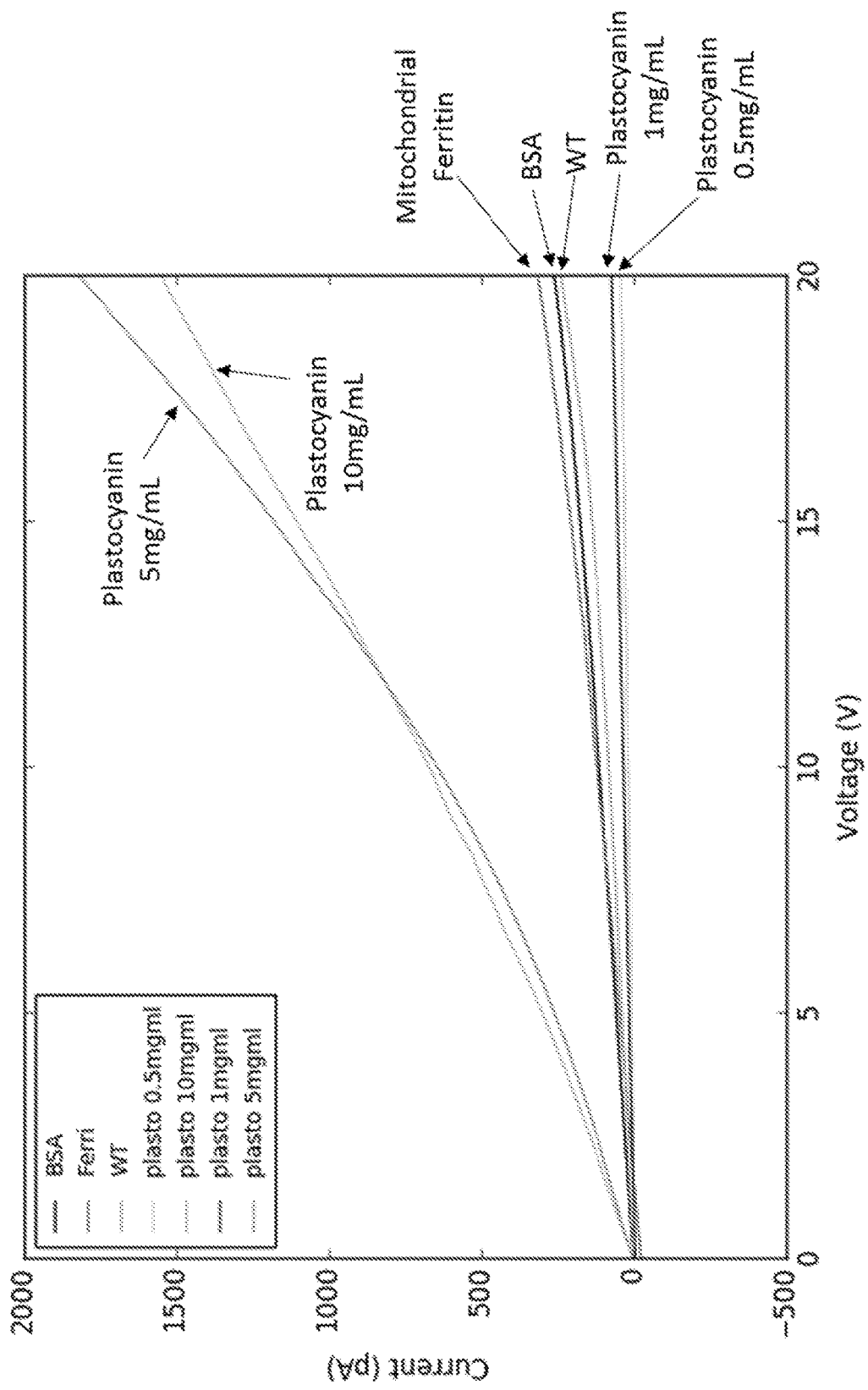
FIG. 23 depicts current-voltage curves for curli fibers comprising CsgA fused to plastocyanin and for curli fibers comprising CsgA fused to ferritin relative to wild-type curli fibers and control proteins dropcast on commercial Micrux electrodes (10 μm spacing) from 1:1 hexafluoro-2-propanol: trifluoroacetic acid solvent control (HFIP:TFA), dried and rinsed with water. Curli fibers or control proteins were dropped at the indicated concentration (where indicated). Current-voltage curves were measured from 0 V to 20 V using a probe station. Current-voltage curves are shown for curli fibers comprising CsgA fused to plastocyanin ("plasto") dropcast at the indicated concentration; curli fibers comprising CsgA fused to ferritin ("Fern"); curli fibers comprising wild-type CsgA ("WT"); or bovine serum albumin control ("BSA"). Where the concentration of the curli fiber or protein is not specified, protein were dropcast at 5 mg/mL. Concentrations of curli fiber comprising CsgA fused to plastocyanin below 5 mg/mL caused a decrease in current.
Figure 24:
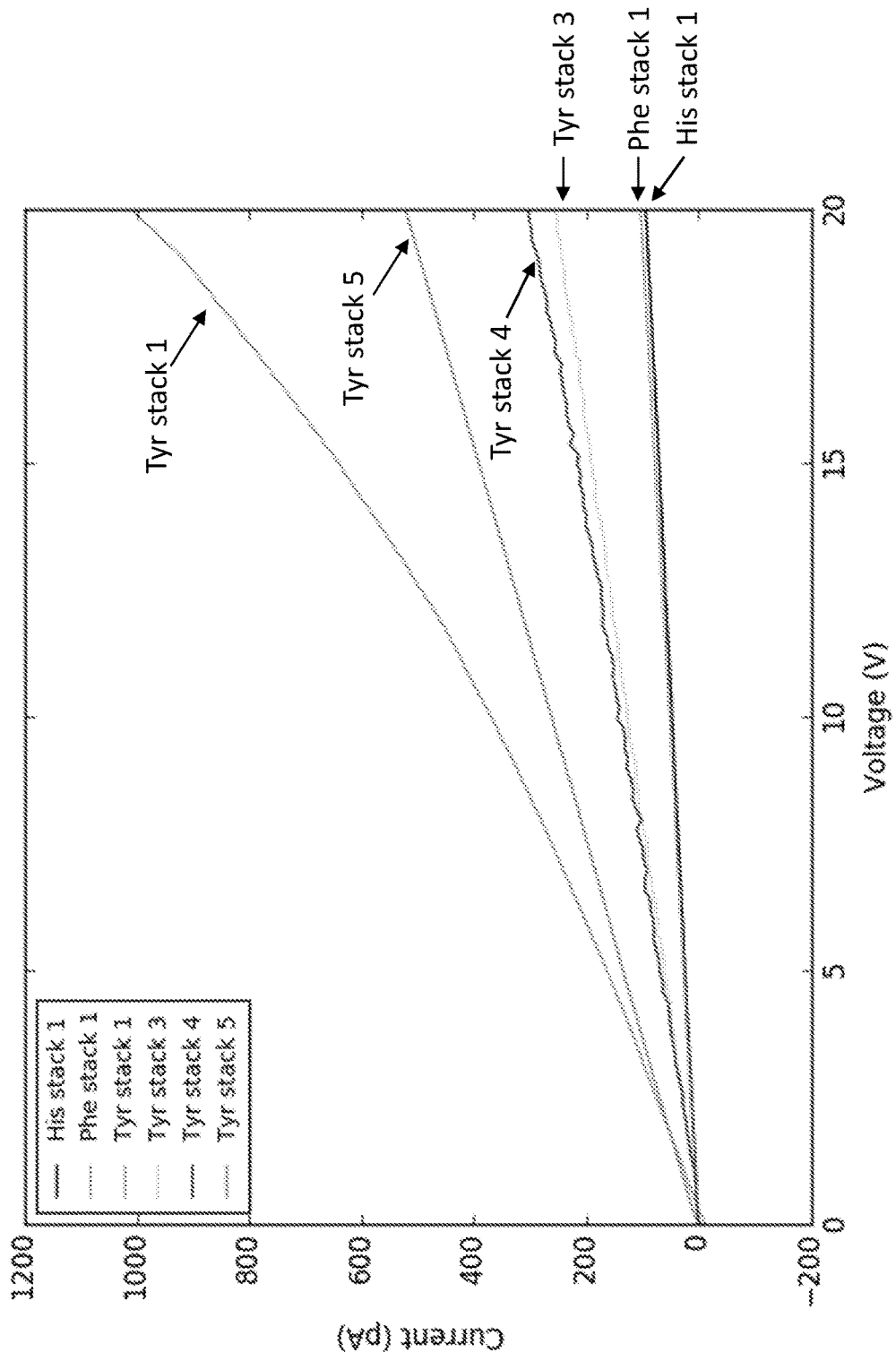
FIG. 24 depicts current-voltage curves of various pi-stack-containing curli fibers. 5 mg/mL solution of curli fiber in 1:1 HFIP:TFA were dropcast on commercial Micrux interdigitated electrodes (10 μm spacing), rinsed with water after drying, and dried in air. Current-voltage curves were measured from 0 V to 20 V using a probe station.
Figure 25:
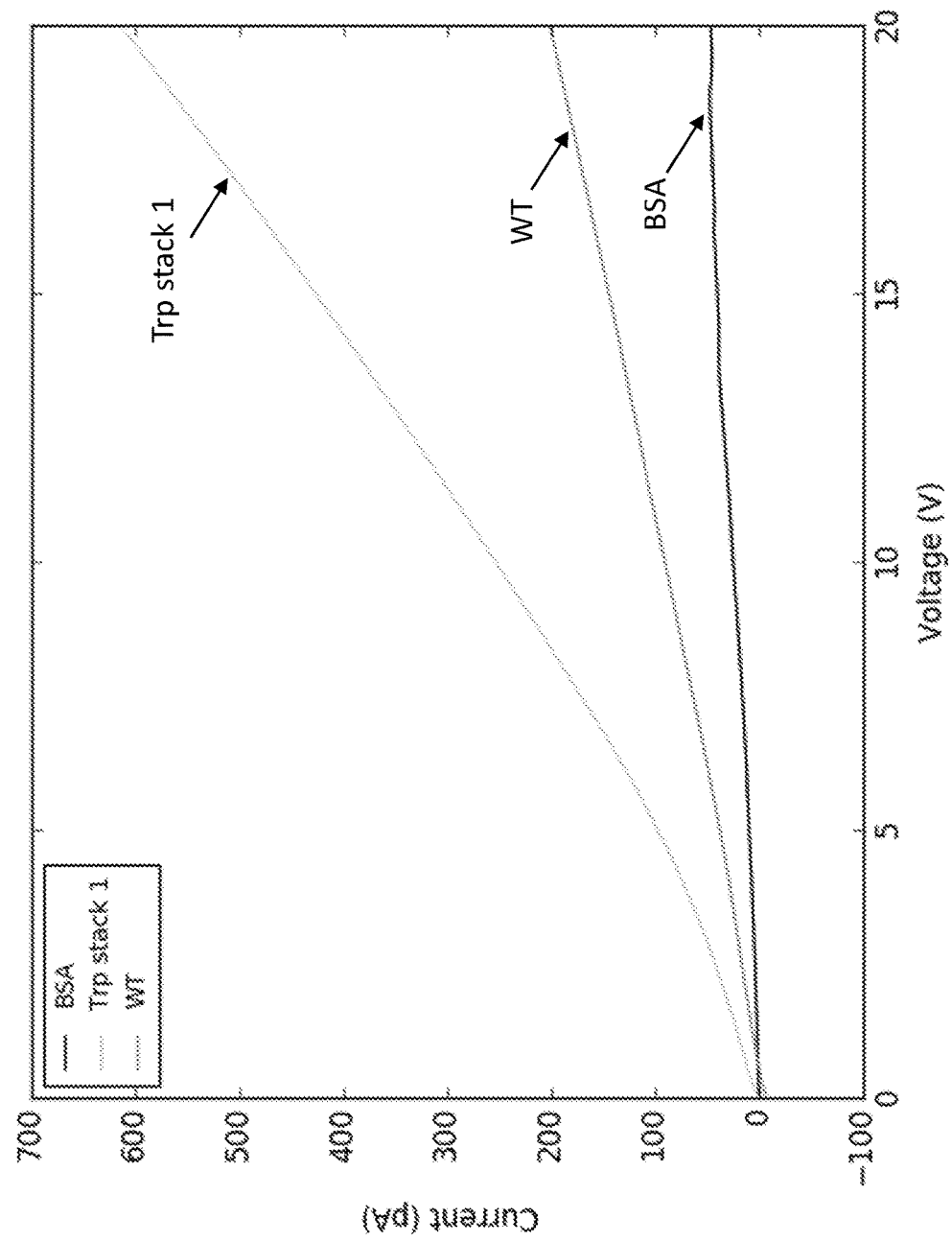
FIG. 25 depicts current voltage curves of curli fibers comprising CsgA mutant containing Trp at positions of stack 1 ("Trp stack 1") relative to curli fibers comprising wild-type CsgA ("WT") and BSA control ("BSA"). 5 mg/mL solution of fibers in 1:1 HFIP:TFA were dropcast on commercial micrux interdigitated electrodes (10 um spacing), rinsed with water after drying, and dried in air. Current-voltage curves were measured from 0 V to 20 V using a probe station.

To characterize the conductivity of thin films using curli fiber comprising mutated CsgA or CsgA fused to a redox active domain, a probe station was used to perform voltage sweeps from 0 to 20 V and the current response was measured (FIGS. 21, 23, 24, 25). The engineered curli fibers with the highest current at a given voltage or steepest curves correspond to curli fibers with the highest conductivity. For CsgA-plastocyanin fusions, −2 V to +2 V, and −30 V to +30 V sweeps were also performed (FIGS. 22A and 22B). A forward and reverse sweep from 0 V to 20 V, and 20 V to 0 V was also recorded and shows little hysteresis between forward and reverse measurements (FIG. 22C).

REFERENCES

Each of the following references is hereby incorporated by reference in its entirety:
1. Pant, D. et al. Bioelectrochemical systems (BES) for sustainable energy production and product recovery from organic wastes and industrial wastewaters. *RSC Adv.* 2, 1248-1263 (2012).

2. Erable, B., Duteanu, N. M., Ghangrekar, M. M., Dumas, C. & Scott, K. Application of electroactive biofilms. *Biofouling* 26, 57-71 (2010).
3. Michener, J. K., Thodey, K., Liang, J. C. & Smolke, C. D. Applications of genetically-encoded biosensors for the construction and control of biosynthetic pathways. *Metabolic Engineering* 14, 212-222 (2012).
4. Vargas, M. et al. Aromatic Amino Acids Required for Pili Conductivity and Long-Range Extracellular Electron Transport in *Geobacter sulfurreducens. mBio* 4, e00105-13-e00105-13 (2013).
5. Pirbadian, S. et al. *Shewanella oneidensis* MR-1 nanowires are outer membrane and periplasmic extensions of the extracellular electron transport components. *Proceedings of the National Academy of Sciences* 111, 12883-12888 (2014).
6. Cherny, I. & Gazit, E. Amyloids: Not Only Pathological Agents but Also Ordered Nanomaterials. *Angew Chem Int Edit* 47, 4062-4069 (2008).
7. Culver, J. N. et al. Plant virus directed fabrication of nanoscale materials and devices. *Virology* 479-480, 200-212 (2015).
8. Fischlechner, M. & Donath, E. Viruses as Building Blocks for Materials and Devices. *Angew Chem Int Edit* 46, 3184-3193 (2007).
9. Ulijn, R. V. & Woolfson, D. N. Peptide and protein based materials in 2010: from design and structure to function and application. *Chem. Soc. Rev.* 39, 3349 (2010).
10. Rodríguez-Ropero, F., Zanuy, D., Assfeld, X. & Alemán, C. Modeling an Electronic Conductor Based on Natural Peptide Sequences. *Biomacromolecules* 10, 2338-2343 (2009).
11. Hamley, I. W. et al. Self-Assembly of a Designed Amyloid Peptide Containing the Functional Thienylalanine Unit. *J. Phys. Chem. B* 114, 10674-10683 (2010).
12. Barnhart, M. M. & Chapman, M. R. Curli Biogenesis and Function. *Annu. Rev. Microbiol.* 60, 131-147 (2006).
13. Malvankar, N. S., Tuominen, M. T. & Lovley, D. R. Comment on 'On electrical conductivity of microbial nanowires and biofilms' by S. M. Strycharz-Glaven, R. M. Snider, A. Guiseppi-Elie and L. M. Tender, Energy Environ. Sci., 2011, 4, 4366. *Energy Environ. Sci.* 5, 6247 (2012).
14. Strycharz-Glaven, S. M. & Tender, L. M. Reply to the 'Comment on "On electrical conductivity of microbial nanowires and biofilms"' by N. S. Malvankar, M. T. Tuominen and D. R. Lovley, Energy Environ. Sci., 2012, 5, DOI: 10.1039/c2ee02613a. *Energy Environ. Sci.* 5, 6250 (2012).
15. Strycharz-Glaven, S. M., Snider, R. M., Guiseppi-Elie, A. & Tender, L. M. On the electrical conductivity of microbial nanowires and biofilms. *Energy Environ. Sci.* 4, 4366 (2011).
16. Botyanszki, Z., Tay, P. K. R., Nguyen, P. Q., Nussbaumer, M. G. & Joshi, N. S. Engineered catalytic biofilms: Site-specific enzyme immobilization onto *E. coli* curli nanofibers. *Biotechnol. Bioeng.* n/a-n/a (2015).
17. Nguyen, P. Q., Botyanszki, Z., Tay, P. K. R. & Joshi, N. S. Programmable biofilm-based materials from engineered curli nanofibres. *Nature Communications* 5, 1-10 (1AD).
18. Zhong, C. et al. Strong underwater adhesives made by self-assembling multi-protein nanofibres. *Nature Nanotech* 1-9 (2014).
19. Van Gerven, N. et al. Secretion and functional display of fusion proteins through the curli biogenesis pathway. *Molecular Microbiology* 91, 1022-1035 (2014).
20. Chen, A. Y. et al. Synthesis and patterning of tunable multiscale materials with engineered cells. *Nat Mater* (2014).
21. Xiao, H. et al. Genetic Incorporation of Histidine Derivatives Using an Engineered PyrrolysyltRNA Synthetase. *ACS Chemical Biology* 9, 1092-1096 (2014).
22. Lajoie, M. J., Rovner, A. J., Goodman, D. B. & Aerni, H. R. Genomically recoded organisms expand biological functions. *Science* (2013).
23. Mottishaw, J. D. & Sun, H. Effects of Aromatic Trifluoromethylation, Fluorination, and Methylation on Intermolecular π-π Interactions. *J. Phys. Chem. A* 117, 7970-7979 (2013).
24. Amit, M., Cheng, G., Hamley, I. W. & Ashkenasy, N. Conductance of amyloid β based peptide filaments: structure-function relations. *Soft Matter* 8, 8690 (2012).
25. Del Mercato, L. L. et al. Charge transport and intrinsic fluorescence in amyloid-like fibrils. *Proceedings of the National Academy of Sciences* 104, 18019-18024 (2007).
26. Amdursky, N. Enhanced solid-state electron transport via tryptophan containing peptide networks. *Phys. Chem. Chem. Phys.* 15, 13479 (2013).
27. Tian, P. et al. Structure of a Functional Amyloid Protein Subunit Computed Using Sequence Variation. *J Am Chem Soc* 137, 22-25 (2015).
28. Wang, X. & Chapman, M. R. Sequence Determinants of Bacterial Amyloid Formation. *J Mol Biol* 380, 570-580 (2008).
29. Jensen, H. M. et al. Engineering of a synthetic electron conduit in living cells. *Proc Natl Acad Sci USA* 107, 19213-19218 (2010).

The invention claimed is:

1. A method of producing a genetically modified bacterium comprising genetically altering a bacterium to include a nucleic acid sequence encoding a mutant amyloid polypeptide having a series of aligned aromatic groups, wherein the aligned aromatic groups form a pi-pi stack, and wherein the nucleic acid sequence is under the control of a promoter to express the mutant amyloid polypeptide.

2. The method of claim 1, wherein the amyloid polypeptide is selected from the group consisting of CsgA, CspA, a beta-lactoglobulin, a lysozyme, Sup35, and an amyloid-beta peptide.

3. The method of claim 1, wherein the aromatic group is present on a standard amino acid or a nonstandard amino acid.

4. The method of claim 1, wherein the aromatic group is present on a standard amino acid selected from the group consisting of phenylalanine, tryptophan, tyrosine and histidine, or wherein the aromatic group is present on a nonstandard amino acid selected from the group consisting of 2-thienylalanine, 3-thienylalanine, acetylphenylalanine and azidophenylalanine.

5. The method of claim 1, wherein the mutant amyloid polypeptide further comprises a redox active domain.

6. The method of claim 1, further comprising genetically altering the bacterium to include second nucleic acid sequence encoding a fusion protein comprising an amyloid polypeptide fused to a redox active domain.

7. The method of claim 1, wherein the bacterium is *E. coli*.

8. The method of claim 1, wherein the bacterium is non-pathogenic.

9. The method of claim 1, wherein the aligned aromatic groups form a pi-pi stack aligned in a geometric configuration selected from the group consisting of sandwich-type pi-stacks, t-shaped pi-stacks, and parallel-displaced pi-stacks.

10. The method of claim 1, wherein the nucleic acid sequence encoding the mutant amyloid polypeptide having a series of aligned aromatic groups comprises a sequence selected from the group consisting of SEQ ID NOs. 3-12 and 62-65.

11. The method of claim 5, wherein the amyloid polypeptide is selected from the group consisting of CsgA, CspA, a beta-lactoglobulin, a lysozyme, Sup35, and an amyloid-beta peptide.

12. The method of claim 5, wherein the redox active domain is selected from the group consisting of: a metalloprotein, a redox enzyme, a binding domain, and a stimuli-responsive peptide.

13. The method of claim 5, wherein the redox active domain is selected from the group consisting of: plastocyanin, an oxygen-carrier protein, a microperoxidase, a cytochrome, a copper-binding protein, an iron-binding protein, a gold-binding domain, a metalloenzyme, rubredoxin, and a fragment thereof.

14. The method of claim 5, wherein the nucleic acid sequence encoding the mutant amyloid polypeptide having a series of aligned aromatic groups comprises a sequence selected from the group consisting of SEQ ID NOs. 3-12 and 62-65.

15. The method of claim 6, wherein the amyloid polypeptide is selected from the group consisting of CsgA, CspA, a beta-lactoglobulin, a lysozyme, Sup35, and an amyloid-beta peptide.

16. The method of claim 6, wherein the redox active domain is selected from the group consisting of: a metalloprotein, a redox enzyme, a binding domain, and a stimuli-responsive peptide.

17. The method of claim 6, wherein the redox active domain is selected from the group consisting of: plastocyanin, an oxygen-carrier protein, a microperoxidase, a cytochrome, a copper-binding protein, an iron-binding protein, a gold-binding domain, a metalloenzyme, rubredoxin, and a fragment thereof.

* * * * *